(12) United States Patent
Peter et al.

US012281310B2

(10) Patent No.: US 12,281,310 B2
(45) Date of Patent: Apr. 22, 2025

(54) USE OF TRINUCLEOTIDE REPEAT RNAs TO TREAT CANCER

(71) Applicant: Northwestern University, Evanston, IL (US)

(72) Inventors: Marcus E. Peter, Chicago, IL (US); Andrea E. Murmann, Chicago, IL (US)

(73) Assignee: Northwestern University, Evanston, IL (US)

( * ) Notice: Subject to any disclaimer, the term of this patent is extended or adjusted under 35 U.S.C. 154(b) by 956 days.

(21) Appl. No.: 17/159,586

(22) Filed: Jan. 27, 2021

(65) Prior Publication Data

US 2021/0147853 A1    May 20, 2021

Related U.S. Application Data

(63) Continuation of application No. 15/899,974, filed on Feb. 20, 2018, now Pat. No. 10,934,547.

(60) Provisional application No. 62/596,457, filed on Dec. 8, 2017, provisional application No. 62/531,991, filed on Jul. 13, 2017, provisional application No. 62/461,042, filed on Feb. 20, 2017.

(51) Int. Cl.
| | |
|---|---|
| *C12N 15/113* | (2010.01) |
| *A61K 31/713* | (2006.01) |
| *A61K 47/64* | (2017.01) |
| *A61K 47/69* | (2017.01) |
| *A61P 35/00* | (2006.01) |
| *C12N 15/11* | (2006.01) |

(52) U.S. Cl.
CPC ........ *C12N 15/1138* (2013.01); *A61K 31/713* (2013.01); *A61K 47/64* (2017.08); *A61K 47/6931* (2017.08); *A61P 35/00* (2018.01); *C12N 15/11* (2013.01); *C12N 15/111* (2013.01); *C12N 15/113* (2013.01); *C12N 2310/122* (2013.01); *C12N 2310/14* (2013.01); *C12N 2310/141* (2013.01); *C12N 2310/531* (2013.01); *C12N 2320/10* (2013.01); *C12N 2320/52* (2013.01)

(58) Field of Classification Search
CPC ....... A61K 31/713; A61P 35/00; C12N 15/11; C12N 15/113; C12N 2310/14
See application file for complete search history.

(56) References Cited

U.S. PATENT DOCUMENTS

| | | | |
|---|---|---|---|
| 7,056,704 B2 * | 6/2006 | Tuschl ................. | C12N 15/113 435/6.16 |
| 10,934,547 B2 * | 3/2021 | Peter ...................... | C12N 15/11 |

| | | | |
|---|---|---|---|
| 2007/0123484 A1 * | 5/2007 | Bhat ..................... | C12N 15/111 514/81 |
| 2015/0344887 A1 | 12/2015 | Song | |
| 2016/0053254 A1 | 2/2016 | De Kimpe et al. | |

FOREIGN PATENT DOCUMENTS

| | | |
|---|---|---|
| EP | 3128008 | 2/2017 |
| WO | 2005121370 A2 | 12/2005 |

OTHER PUBLICATIONS

De Mezer et al (Nucleic Acids Research 39(9): 3852-3863, 2011) (Year: 2011).*
Barton et al (Mol Cancer Ther; 14(3): 769-778, Mar. 2015) (Year: 2015).*
Eder, I.E., et al, "Inhibition of LNCaP Prostate Tumor Growth in vivo by an Antisense Oligonucleotide directed against the Human Androgen Receptors", Cancer Gene Therapy, 2002, vol. 9, pp. 117-125.
Liu, W., et al., "Specific Inhibition of Huntington's Disease Gene Expression by siRNAs in Cultured Cells", Proc. Japan Acad., 2003, vol. 79, pp. 293-298.
International Search Report and Written Opinion for PCT/US2018/018798 dated Jun. 14, 2018.
Banez-Coronel M, Porta S, Kagerbauer B, Mateu-Huertas E, Pantano L, Ferrer I, Guzman M, Estivill X, Marti E (2012) A pathogenic mechanism in Huntington's disease involves small CAG-repeated RNAs with neurotoxic activity. PLoS Genet 8: e1002481.
Bilen J, Liu N, Burnett BG, Pittman RN, Bonini NM (2006) MicroRNA pathways modulate polyglutamine-induced neurodegeneration. Mol Cell 24: 157-63.
Blomen VA, Majek P, Jae LT, Bigenzahn JW, Nieuwenhuis J, Staring J, Sacco R, van Diemen FR, Olk N, Stukalov A, et al. (2015) Gene essentiality and synthetic lethality in haploid human cells. Science 350: 1092-6.
Ceppi P, Hadji A, Kohlhapp F, Pattanayak A, Hau A, Xia L, Liu H, Murmann AE, Peter ME. (2014). CD95 and CD95L promote and protect cancer stem cells. Nature Commun. 5:5238.
Clark RM, Dalgliesh GL, Endres D, Gomez M, Taylor J, Bidichandani SI (2004) Expansion of GAA triplet repeats in the human genome: unique origin of the FRDA mutation at the center of an Alu. Genomics 83: 373-83.

(Continued)

*Primary Examiner* — Richard A Schnizer
(74) *Attorney, Agent, or Firm* — Quarles & Brady LLP

(57) ABSTRACT

Disclosed are compositions and methods related to RNA interference (RNAi) and the use of RNAi active sequence for treating diseases and disorders. Particular disclosed are toxic RNAi active sequences such as siRNA and shRNA for killing cancer cells. The disclosed toxic RNAi active sequences typically include trinucleotide repeats and preferentially target the expression of multiple essential genes for cell survival and/or growth.

18 Claims, 33 Drawing Sheets

Specification includes a Sequence Listing.

(56) References Cited

OTHER PUBLICATIONS

Cleary JD, Ranum LP (2017) New developments in RAN translation: insights from multiple diseases. Curr Opin Genet Dev 44: 125-134.

Coarelli G, Diallo A, Thion MS, Rinaldi D, Calvas F, Boukbiza OL, Tataru A, Charles P, Tranchant C, Marelli C, et al. (2017) Low cancer prevalence in polyglutamine expansion diseases. Neurology 88: 1114-1119.

Gatchel JR, Zoghbi HY (2005) Diseases of unstable repeat expansion: mechanisms and common principles. Nat Rev Genet 6: 743-55.

Giovannucci E, Stampfer MJ, Krithivas K, Brown M, Dahl D, Brufsky A, Talcott J, Hennekens CH, Kantoff PW (1997) The CAG repeat within the androgen receptor gene and its relationship to prostate cancer. Proc Natl Acad Sci U S A 94: 3320-3.

Gu M, Dong X, Zhang X, Niu W (2012) The CAG repeat polymorphism of androgen receptor gene and prostate cancer: a meta-analysis. Molecular biology reports 39: 2615-24.

Hadji A, Ceppi P, Murmann AE, Brockway S, Pattanayak A, Bhinder B, Hau A, De Chant S, Parimi V, Kolesza P, et al. (2014) Death induced by CD95 or CD95 ligand elimination. Cell Reports 10: 208-222.

Hakimi JM, Schoenberg MP, Rondinelli RH, Piantadosi S, Barrack ER (1997) Androgen receptor variants with short glutamine or glycine repeats may identify unique subpopulations of men with prostate cancer. Clin Cancer Res 3: 1599-608.

Ho TH, Savkur RS, Poulos MG, Mancini MA, Swanson MS, Cooper TA (2005) Colocalization of muscleblind with RNA foci is separable from mis-regulation of alternative splicing in myotonic dystrophy. J Cell Sci 118: 2923-33.

Hsu RJ, Hsiao KM, Lin MJ, Li CY, Wang LC, Chen LK, Pan H (2011) Long tract of untranslated CAG repeats is deleterious in transgenic mice. PLoS One 6: e16417.

Irvine RA, Yu MC, Ross RK, Coetzee GA (1995) The CAG and GGC microsatellites of the androgen receptor gene are in linkage disequilibrium in men with prostate cancer. Cancer Res 55: 1937-40.

Ingles SA, Ross RK, Yu MC, Irvine RA, La Pera G, Haile RW, Coetzee GA (1997) Association of prostate cancer risk with genetic polymorphisms in vitamin D receptor and androgen receptor. J Natl Cancer Inst 89: 166-70.

Jiang F, Ye X, Liu X, Fincher L, McKearin D, Liu Q (2005) Dicer-1 and R3D1-L catalyze microRNA maturation in *Drosophila*. Genes Dev 19: 1674-9.

Ji J, Sundquist K, Sundquist J (2012) Cancer incidence in patients with polyglutamine diseases: a population-based study in Sweden. Lancet Oncol 13: 642-8.

Kim YK, Kim B, Kim VN (2016) Re-evaluation of the roles of DROSHA, Export in 5, and DICER in microRNA biogenesis. Proc Natl Acad Sci U S A 113: E1881-9.

Kozlowski P, de Mezer M, Krzyzosiak WJ (2010) Trinucleotide repeats in human genome and exome. Nucleic Acids Res 38: 4027-39.

Krol J, Fiszer A, Mykowska A, Sobczak K, de Mezer M, Krzyzosiak WJ (2007) Ribonuclease dicer cleaves triplet repeat hairpins into shorter repeats that silence specific targets. Mol Cell 25: 575-86.

La Spada AR, Wilson EM, Lubahn DB, Harding AE, Fischbeck KH (1991) Androgen receptor gene mutations in X-linked spinal and bulbar muscular atrophy. Nature 352: 77-9.

Lawlor KT, O'Keefe LV, Samaraweera SE, van Eyk CL, McLeod CJ, Maloney CA, Dang TH, Suter CM, Richards RI (2011) Double-stranded RNA is pathogenic in *Drosophila* models of expanded repeat neurodegenerative diseases. Hum Mol Genet 20: 3757-68.

Lee JM, Galkina EI, Levantovsky RM, Fossale E, Anne Anderson M, Gillis T, Srinidhi Mysore J, Coser KR, Shioda T, Zhang B, et al. (2013) Dominant effects of the Huntington's disease HTT CAG repeat length are captured in gene-expression data sets by a continuous analysis mathematical modeling strategy. Hum Mol Genet 22: 3227-38.

Li LB, Yu Z, Teng X, Bonini NM (2008) RNA toxicity is a component of ataxin-3 degeneration in *Drosophila*. Nature 453: 1107-11.

Lin L, Park JW, Ramachandran S, Zhang Y, Tseng YT, Shen S, Waldvogel HJ, Curtis MA, Faull RL, Troncoso JC, et al. (2016) Transcriptome sequencing reveals aberrant alternative splicing in Huntington's disease. Hum Mol Genet 25: 3454-3466.

Liu Y, Wilson SH (2012) DNA base excision repair: a mechanism of trinucleotide repeat expansion. Trends Biochem Sci 37: 162-72.

McMahon KM, Plebanek MP, Thaxton CS (2016) Properties of native high-density lipoproteins inspire synthesis of actively targeted in vivo siRNA delivery vehicles. Adv Funct Mater 26: 7824-7835.

Moseley ML, Zu T, Ikeda Y, Gao W, Mosemiller AK, Daughters RS, Chen G, Weatherspoon MR, Clark HB, Ebner TJ, et al. (2006) Bidirectional expression of CUG and CAG expansion transcripts and intranuclear polyglutamine inclusions in spinocerebellar ataxia type 8. Nat Genet 38: 758-69.

Murmann AE, McMahon KM, Halluck-Kangas A, Ravindran N, Patel M, Law C, Brockway S, Wei JJ, Thaxton CS, Peter ME (2017) Induction of DISE in ovarian cancer cells in vivo. Oncotarget 8: 84643-84658.

Nalavade R, Griesche N, Ryan DP, Hildebrand S, Krauss S (2013) Mechanisms of RNA-induced toxicity in CAG repeat disorders. Cell Death Dis 4: e752.

Napierala M, Krzyzosiak WJ (1997) CUG repeats present in myotonin kinase RNA form metastable "slippery" hairpins. J Biol Chem 272: 31079-85.

Orr HT, Zoghbi HY (2007) Trinucleotide repeat disorders. Annu Rev Neurosci 30: 575-621.

Patel M, Peter ME (2017) Identification of DISE-inducing shRNAs by monitoring cellular responses. Cell Cycle: doi: 10.1080/15384101. 2017.1383576.

Putzbach W, Gao QQ, Patel M, van Dongen S, Haluck-Kangas A, Sarshad AA, Bartom E, Kim KY, Scholtens DM, Hafner M, et al. (2017) Many si/shRNAs can kill cancer cells by targeting multiple survival genes through an off-target mechanism. eLife 6: e29702.

Ross CA (2002) Polyglutamine pathogenesis: emergence of unifying mechanisms for Huntington's disease and related disorders. Neuron 35: 819-22.

Rue L, Banez-Coronel M, Creus-Muncunill J, Giralt A, Alcala-Vida R, Mentxaka G, Kagerbauer B, Zomeno-Abellan MT, Aranda Z, Venturi V, et al. (2016) Targeting CAG repeat RNAs reduces Huntington's disease phenotype independently of huntingtin levels. J Clin Invest 126: 4319-4330.

Sharp AH, Loev SJ, Schilling G, Li SH, Li XJ, Bao J, Wagster MV, Kotzuk JA, Steiner JP, Lo A, et al. (1995) Widespread expression of Huntington's disease gene (IT15) protein product. Neuron 14: 1065-74.

Sorensen SA, Fenger K, Olsen JH (1999) Significantly lower incidence of cancer among patients with Huntington disease: An apoptotic effect of an expanded polyglutamine tract? Cancer 86: 1342-6.

Tsujimoto Y, Takakuwa T, Takayama H, Nishimura K, Okuyama A, Aozasa K, Nonomura N (2004) In situ shortening of CAG repeat length within the androgen receptor gene in prostatic cancer and its possible precursors. Prostate 58: 283-90.

Turner MR, Goldacre R, Goldacre MJ (2013) Reduced cancer incidence in Huntington's disease: record linkage study clue to an evolutionary trade-off? Clin Genet 83: 588-90.

Van Dongen S, Abreu-Goodger C, Enright AJ (2008) Detecting microRNA binding and siRNA off-target effects from expression data. Nat Methods 5: 1023-5.

Vonsattel JP, DiFiglia M (1998) Huntington disease. J Neuropathol Exp Neurol 57: 369-84.

Wang T, Birsoy K, Hughes NW, Krupczak KM, Post Y, Wei JJ, Lander ES, Sabatini DM (2015) Identification and characterization of essential genes in the human genome. Science 350: 1096-101.

Wojciechowska M, Krzyzosiak WJ (2011) Cellular toxicity of expanded RNA repeats: focus on RNA foci. Hum Mol Genet 20: 3811-21.

(56) References Cited

OTHER PUBLICATIONS

Yu Z, Teng X, Bonini NM (2011) Triplet repeat-derived siRNAs enhance RNA-mediated toxicity in a *Drosophila* model for myotonic dystrophy. PLoS Genet 7: e1001340.
Zamudio JR, Kelly TJ, Sharp PA (2014) Argonaute-bound small RNAs from promoter-proximal RNA polymerase II. Cell 156: 920-34.
Agostini M, et al. (2014). miR-34: from bench to bedside. Oncotargel. 5:872-81.
Baek D, et al. (2008). The impact of microRNAs on protein output. Nature. 455:64-71.
Balatti, V., et al. "miR deregulation in CLL." Advances in Chronic Lymphocytic Leukemia (2013): 309-325.
Beg, M. S., et al. "Phase I study of MRX34, a liposomal miR-34a mimic, administered twice weekly in patients with advanced solid tumors." Investigational new drugs 35.2 (2017): 180-188.
Bernstein, E., et al. "Role for a bidentate ribonuclease in the initiation step of RNA interference." Nature 409.6818 (2001): 363-366.
Birmingham, A., et al. "3' UTR seed matches, but not overall identity, are associated with RNAi off-targets." Nature methods 3.3 (2006): 199-204.
Bramsen, J. B., et al. "A large-scale chemical modification screen identifies design rules to generate siRNAs with high activity, high stability and low toxicity." Nucleic acids research 37.9 (2009): 2867-2881.
Cao, W., et al. "miR-34a regulates cisplatin-induce gastric cancer cell death by modulating PI3K/AKT/survivin pathway." Tumor Biology 35.2 (2014): 1287-1295.
Chandradoss, S. D., et al. "A dynamic search process underlies microRNA targeting." Cell 162.1 (2015): 96-107.
Chang, B.-D., et al. "A senescence-like phenotype distinguishes tumor cells that undergo terminal proliferation arrest after exposure to anticancer agents." Cancer research 59.15 (1999): 3761-3767.
Concepcion, C. P., et al. "The miR-17-92 family of microRNA clusters in development and disease." Cancer journal (Sudbury, Mass.) 18.3 (2012): 262.
Concepcion, C. P., et al. "Intact p53-dependent responses in miR-34-deficient mice." PLoS genetics 8.7 (2012):e1002797.
Di Martino, M. T., et al. "Synthetic miR-34a mimics as a novel therapeutic agent for multiple myeloma: in vitro and in vivo evidence." Clinical cancer research 18.22 (2012): 6260-6270.
Elkayam, E., et al. "Multivalent recruitment of human argonaute by GW182." Molecular cell 67.4 (2017): 646-658.
Eom, Y.-W., et al. "Two distinct modes of cell death induced by doxorubicin: apoptosis and cell death through mitotic catastrophe accompanied by senescence-like phenotype." Oncogene 24.30 (2005): 4765-4777.
Esquela-Kerscher, A., et al. "Oncomirs—microRNAs with a role in cancer." Nature reviews cancer 6.4 (2006): 259-269.
Eulalio, A., et al. "GW182 interaction with Argonaute is essential for miRNA-mediated translational repression and mRNA decay." Nature structural & molecular biology 15.4 (2008): 346-353.
Fedorov, Y., et al. "Off-target effects by siRNA can induce toxic phenotype." Rna 12.7 (2006): 1188-1196.
Friedman, R. C., et al. "Most mammalian mRNAs are conserved targets of microRNAs." Genome research 19.1 (2009): 92-105.
Grimson, A., et al. "MicroRNA targeting specificity in mammals: determinants beyond seed pairing." Molecular cell 27.1 (2007): 91-105.
Gu, S., et al. "Weak base pairing in both seed and 3' regions reduces RNAi off-targets and enhances si/shRNA designs." Nucleic acids research 42.19 (2014): 12169-12176.
Han, J., et al. "The Drosha-DGCR8 complex in primary microRNA processing." Genes & development 18.24 (2004): 3016-3027.
Hau, A., et al. "CD95 is part of a let-7/p53/miR-34 regulatory network." PLoS one 7.11 (2012): e49636.
Hauptmann, J., et al. "Biochemical isolation of Argonaute protein complexes by Ago-APP." Proceedings of the National Academy of Sciences 112.38 (2015): 11841-11845.

He, X., et al. "The guardian's little helper: microRNAs in the p53 tumor suppressor network." Cancer research 67.23 (2007): 11099-11101.
Hermeking, H. J. C. D. "The miR-34 family in cancer and apoptosis." Cell Death & Differentiation 17.2 (2010): 193-199.
Hua, Y., et al. "miRConnect 2.0: identification of oncogenic, antagonistic miRNA families in three human cancers." BMC Genomics 14 (2013): 179-179.
Hutvágner, G., et al. "A cellular function for the RNA-interference enzyme Dicer in the maturation of the let-7 small temporal RNA." Science 293.5531 (2001): 834-838.
International Search Report and Written Opinion for PCT/US2018/018801 dated Jun. 7, 2018.
Jackson, A. L., et al. "Expression profiling reveals off-target gene regulation by RNAi." Nature biotechnology 21.6 (2003): 635-637.
Kamola, P.J., et al., "The siRNA non-seed region and its target sequences are auxiliary determinants of off-target effects", PloS Comput Biol., 2015, vol. 11, No. 12, pp. 1-17.
Karlas, A., et al. "A human genome-wide loss-of-function screen identifies effective chikungunya antiviral drugs." Nature Communications 7.11320: 1.
Kozomara, A., et al. "miRBase: annotating high confidence microRNAs using deep sequencing data." Nucleic acids research 42.D1 (2014): D68-D73.
Kumar, M. S., et al. "Impaired microRNA processing enhances cellular transformation and tumorigenesis." Nature genetics 39.5 (2007): 673-677.
Kwon, H.-K., et al. "Etoposide induces necrosis through p53-mediated antiapoptosis in human kidney proximal tubule cells." Toxicological Sciences 148.1 (2015): 204-219.
Lawrence, M. S., et al. "Mutational heterogeneity in cancer and the search for new cancer-associated genes." Nature 499.7457 (2013): 214-218.
Lee, Y., et al. "MicroRNA genes are transcribed by RNA polymerase II." The EMBO journal 23.20 (2004): 4051-4060.
Lenkala, D., et al. "The impact of microRNA expression on cellular proliferation." Human genetics 133.7 (2014): 931-938.
Leuschner, P. JF, et al. "Cleavage of the siRNA passenger strand during RISC assembly in human cells." EMBO reports 7.3 (2006): 314-320.
Lewis, B. P., et al. "Conserved seed pairing, often flanked by adenosines, indicates that thousands of human genes are microRNA targets." cell 120.1 (2005): 15-20.
Louie, E., et al. "Nucleotide frequency variation across human genes." Genome research 13.12 (2003): 2594-2601.
Meijer, H. A., et al. "Regulation of miRNA strand selection: follow the leader?." Biochemical Society Transactions 42.4 (2014): 1135-1140.
Meredith, A.-M., et al. "Increasing role of the cancer chemotherapeutic doxorubicin in cellular metabolism." Journal of Pharmacy and Pharmacology 68.6 (2016): 729-741.
Mignone F, et al. (2002). Untranslated regions of mRNAs. Genome Biol. 3:REVIEWS0004.
Mohr, S. E., et al. "RNAi screening comes of age: improved techniques and complementary approaches." Nature reviews Molecular cell biology 15.9 (2014): 591-600.
Murmann, A. E., et al. "Small interfering RNAs based on huntingtin trinucleotide repeats are highly toxic to cancer cells." EMBO reports 19.3 (2018): e45336.
Narendrula R, et al. (2016). RNA disruption is associated with response to multiple classes of chemotherapy drugs in tumor cell lines. BMC Cancer. 16:146.
Navarro, F., et al. "miR-34 and p53: new insights into a complex functional relationship." PLoS one 10.7 (2015): e0132767.
Park SM, et al. (2008). The miR-200 family determines the epithelial phenotype of cancer cells by targeting the E-cadherin repressors, ZEB1 and ZEB2. Genes Dev. 22:894-907.
Park SM, et al. (2007). Let-7 Prevents Early Cancer Progression by Suppressing Expression of the Embryonic Gene HMGA2. Cell Cycle. 6:2585-90.
Patel VD, et al. (2017). Ancient human miRNAs are more likely to have broad functions and disease associations than young miRNAs. BMC Genomics. 18:672.

(56) References Cited

OTHER PUBLICATIONS

Peter ME. (2009). Let-7 and miR-200 microRNAs: guardians against pluripotency and cancer progression. Cell Cycle. 8:843-52.
Petri S, et al. (2013). siRNA design principles and off-target effects. Methods Mol Biol. 986:59-71.
Petri, S., et al., "Increased siRNA duplex stability correlates with reduced off-target and elevated on-target effects", RNA, 2011, vol. 17, No. 4, pp. 737-749.
Putzbach W, et al. (2017). DISE—A Seed Dependent RNAi Off-Target Effect that Kills Cancer Cells. Trends in Cancer. In press.
Schickel R, et al. (2008). MicroRNAs: key players in the immune system, differentiation, tumorigenesis and cell death. Oncogene. 27:5959-74.
Schirle NT, et al. (2012). The crystal structure of human Argonaute2. Science (New York, NY). 336:1037-40.
Selbach M, et al. (2008). Widespread changes in protein synthesis induced by microRNAs. Nature. 455:58-63.
Slabakova E, et al. (2017). Alternative mechanisms of miR-34a regulation in cancer. Cell Death Dis. 8:e3100.
Stark A, et al. (2005). Animal MicroRNAs confer robustness to gene expression and have a significant impact on 3'UTR evolution. Cell. 123:1133-46.
Ji-Tei K, et al. (2004). Guidelines for the selection of highly effective siRNA sequences for mammalian and chick RNA interference. Nucleic Acids Res. 32:936-48.
Walz AL, et al. (2015). Recurrent DGCR8, DROSHA, and SIX homeodomain mutations in favorable histology Wilms tumors. Cancer Cell. 27:286-97.
Wang D, et al. (2005). Cellular processing of platinum anticancer drugs. Nat Rev Drug Discov. 4:307-20.
Wang Y, et al. (2008). Structure of the guide-strand-containing argonaute silencing complex. Nature. 456:209-13.
Whitehurst AW, et al. (2007). Synthetic lethal screen identification of chemosensitizer loci in cancer cells. Nature. 446:815-9.
Yang J, et al. (2013). MiR-34 modulates Caenorhabditis elegans lifespan via repressing the autophagy gene atg9. Age. 35:11-22.
Yeung TK, et al. (1999). The mode of action of taxol: apoptosis at low concentration and necrosis at high concentration. Biochem Biophys Res Commun. 263:398-404.
Yi R, et al. (2003). Exportin-5 mediates the nuclear export of pre-microRNAs and short hairpin RNAs. Genes Dev. 17:3011-6.
Yoo SH, et al. (2012). Etoposide induces a mixed type of programmed cell death and overcomes the resistance conferred by Bcl-2 in Hep3B hepatoma cells. Int J Oncol. 41:1443-54.
Zare H, et al. (2014). An evolutionarily biased distribution of miRNA sites toward regulatory genes with high promoter-driven intrinsic transcriptional noise. BMC Evol Biol. 14:74.

\* cited by examiner

Fam. 5

| Triplet | Rev.com. | AA |
|---|---|---|
| ACG | CGU | Arg |
| CGU | ACG | Thr |
| CGA | UCG | Ser |
| UCG | CGA | Arg |
| GAC | GUC | Val |
| GUC | GAC | Asp |

Fam. 7

| Triplet | Rev.com. | AA |
|---|---|---|
| CAG | CUG | Leu |
| CUG | CAG | Gln |
| AGC | GCU | Ala |
| GCU | AGC | Ser |
| GCA | UGC | Cys |
| UGC | GCA | Ala |

Figure 4B siCAG/CUG (SEQ ID NO:8)   5'—GCUGCUGCUGCUGCUGCUGUT—3'
                       |||||||||||||||||||
(SEQ ID NO:7)   3'—dAdACGACGACGACGACGACGAC—5' siAGC/GCU (SEQ ID NO:23)  5'—UGCUGCUGCUGCUGCUGCUTT—3'
                       |||||||||||||||||||
(SEQ ID NO:22)  3'—dAdAACGACGACGACGACGACGA—5' siGCA/UGC (SEQ ID NO:25)  5'—CUGCUGCUGCUGCUGCUGCTT—3'
                       |||||||||||||||||||
(SEQ ID NO:24)  3'—dAdAGACGACGACGACGACGACG—5'

Figure 15C

| Assay | Units | sINT-TLP 01 1889 | sINT-TLP 02 1890 | siCAG/CUG-TLP 03 1893 | siCAG/CUG-TLP 04 1904 |
|---|---|---|---|---|---|
| CHOL | mg/dL | 85 [2] | 91 [2] | 77 | 96 |
| TRIG | mg/dL | 47 [2] | 37 [2] | 34 | 44 |
| ALT | U/L | 44 | 37 | 26 | 202 |
| AST | U/L | 248 | 247 | 172 | 343 |
| GGT | U/L | 1 [1] | 1 [1] | 1 [1] | 1 [1] |
| ALP | U/L | 20 | 17 | 11 | 49 |
| GLU | mg/dL | 101 | 80 | 79 | 76 |
| PHOS | mg/dL | 5.6 | 7.8 | 6.8 | 5.9 |
| Ca | mg/dL | 8.6 [2] | 8.7 [2] | 9.1 [2] | 9.2 [2] |
| TP | g/dL | 4.6 [2] | 4.8 [2] | 4.2 [2] | 4.9 [2] |
| ALB | g/dL | 2 [2] | 2.2 [2] | 2 [2] | 2.4 [2] |
| GLOB | g/dL | - [3] | - [3] | - [3] | - [3] |
| A/G | - | - [3] | - [3] | - [3] | - [3] |
| BUN | mg/dL | 14 | 36 | 23 | 21 |
| CREAT | mg/dL | 0.1 [1] | 0.1 [1] | 0.1 [1] | 0.1 [1] |
| B/C | - | - [3] | - [3] | - [3] | - [3] |
| TBIL | mg/dL | 0.49 | 0.67 | 0.30 | 0.46 |
| Na | mEq/L | 25 [1] | 25 [1] | 71 | 25 [1] |
| K | mEq/L | 1.6 | 2.7 | 4.1 | 2.5 |
| Na/K | - | - [3] | - [3] | 17.32 | - [3] |

```
                        SEQUENCE LISTING

<160> NUMBER OF SEQ ID NOS: 27

<210> SEQ ID NO 1
<211> LENGTH: 19
<212> TYPE: RNA
<213> ORGANISM: Artificial
<220> FEATURE:
<223> OTHER INFORMATION: Artificial siRNA designed to include a seed
      sequence that is non-targeting in mammalian cells

<400> SEQUENCE: 1
ugguuuacau guuguguga                                                  19

<210> SEQ ID NO 2
<211> LENGTH: 19
<212> TYPE: RNA
<213> ORGANISM: Artificial
<220> FEATURE:
<223> OTHER INFORMATION: Artificial siRNA designed to include a seed
      sequence that is non-targeting in mammalian cells

<400> SEQUENCE: 2
ugguuuacau gucgacuaa                                                  19

<210> SEQ ID NO 3
<211> LENGTH: 19
<212> TYPE: RNA
<213> ORGANISM: Homo sapiens

<400> SEQUENCE: 3
gcccuucaau uacccauau                                                  19

<210> SEQ ID NO 4
<211> LENGTH: 19
<212> TYPE: RNA
<213> ORGANISM: Artificial
<220> FEATURE:
<223> OTHER INFORMATION: Artificial siRNA designed to include seed
      sequence for human CD95L exon 1

<400> SEQUENCE: 4
ugguuuacau gucccauaa                                                  19

<210> SEQ ID NO 5
<211> LENGTH: 19
```

```
<212> TYPE: RNA
<213> ORGANISM: Artificial
<220> FEATURE:
<223> OTHER INFORMATION: Artificial siRNA designed to include a seed
      sequence that is non-targeting in mammalian cells

<400> SEQUENCE: 5
ugguaaacua guugucuga                                                      19

<210> SEQ ID NO 6
<211> LENGTH: 19
<212> TYPE: RNA
<213> ORGANISM: Artificial
<220> FEATURE:
<223> OTHER INFORMATION: Artificial siRNA designed to include seed
      sequence for human CD95L exon 1

<400> SEQUENCE: 6
ugguaaacua gucccauaa                                                      19

<210> SEQ ID NO 7
<211> LENGTH: 21
<212> TYPE: DNA
<213> ORGANISM: Artificial
<220> FEATURE:
<223> OTHER INFORMATION: Artificial siRNA designed to include CAG
      triplet repeat and terminal dideoxynucleotide adenines

<400> SEQUENCE: 7
cagcagcagc agcagcagca a                                                   21

<210> SEQ ID NO 8
<211> LENGTH: 21
<212> TYPE: DNA
<213> ORGANISM: Artificial
<220> FEATURE:
<223> OTHER INFORMATION: Artificial siRNA designed to include antisense
      sequence for siRNA containing CAG repeats and include
      dideoxynucleotide thymidines

<400> SEQUENCE: 8
gcugcugcug cugcugcugt t                                                   21

<210> SEQ ID NO 9
<211> LENGTH: 10
<212> TYPE: DNA
<213> ORGANISM: Homo sapien

<400> SEQUENCE: 9
ctgctgctgc                                                                10

<210> SEQ ID NO 10
<211> LENGTH: 10
<212> TYPE: DNA
<213> ORGANISM: Homo sapien

<400> SEQUENCE: 10
tctgagacca                                                                10

<210> SEQ ID NO 11
<211> LENGTH: 10
<212> TYPE: DNA
<213> ORGANISM: Homo sapien

<400> SEQUENCE: 11
tgctgctgct                                                                10
```

```
<210> SEQ ID NO 12
<211> LENGTH: 10
<212> TYPE: DNA
<213> ORGANISM: Homo sapien

<400> SEQUENCE: 12
gggggtgggg                                                            10

<210> SEQ ID NO 13
<211> LENGTH: 10
<212> TYPE: DNA
<213> ORGANISM: Homo sapien

<400> SEQUENCE: 13
cctccctccc                                                            10

<210> SEQ ID NO 14
<211> LENGTH: 10
<212> TYPE: DNA
<213> ORGANISM: Homo sapien

<400> SEQUENCE: 14
ccccgccccc                                                            10

<210> SEQ ID NO 15
<211> LENGTH: 10
<212> TYPE: DNA
<213> ORGANISM: Homo sapien

<400> SEQUENCE: 15
ggccctggcc                                                            10

<210> SEQ ID NO 16
<211> LENGTH: 10
<212> TYPE: DNA
<213> ORGANISM: Homo sapien

<400> SEQUENCE: 16
cactccccac                                                            10

<210> SEQ ID NO 17
<211> LENGTH: 10
<212> TYPE: DNA
<213> ORGANISM: Homo sapien

<400> SEQUENCE: 17
ggcagggtg                                                             10

<210> SEQ ID NO 18
<211> LENGTH: 10
<212> TYPE: DNA
<213> ORGANISM: Homo sapien

<400> SEQUENCE: 18
gggggtgggg                                                            10

<210> SEQ ID NO 19
<211> LENGTH: 10
<212> TYPE: DNA
<213> ORGANISM: Homo sapien

<400> SEQUENCE: 19
```

```
cctccctccc                                                          10

<210> SEQ ID NO 20
<211> LENGTH: 10
<212> TYPE: DNA
<213> ORGANISM: Homo sapien

<400> SEQUENCE: 20
ccccgccccc                                                          10

<210> SEQ ID NO 21
<211> LENGTH: 19
<212> TYPE: DNA
<213> ORGANISM: Homo sapien

<400> SEQUENCE: 21
gctgctgctg ctgctgctg                                                19

<210> SEQ ID NO 22
<211> LENGTH: 21
<212> TYPE: DNA
<213> ORGANISM: Artificial
<220> FEATURE:
<223> OTHER INFORMATION: Artificial siRNA designed to include CAG
      triplet repeat and terminal dideoxynucleotide adenines

<400> SEQUENCE: 22
agcagcagca gcagcagcaa a                                             21

<210> SEQ ID NO 23
<211> LENGTH: 21
<212> TYPE: DNA
<213> ORGANISM: Artificial
<220> FEATURE:
<223> OTHER INFORMATION: Artificial siRNA designed to include antisense
      sequence for siRNA containing CAG repeats and include
      dideoxynucleotide thymidines

<400> SEQUENCE: 23
ugcugcugcu gcugcugcut t                                             21

<210> SEQ ID NO 24
<211> LENGTH: 21
<212> TYPE: DNA
<213> ORGANISM: Artificial
<220> FEATURE:
<223> OTHER INFORMATION: Artificial siRNA designed to include CAG
      triplet repeat and terminal dideoxynucleotide adenines

<400> SEQUENCE: 24
gcagcagcag cagcagcaga a                                             21

<210> SEQ ID NO 25
<211> LENGTH: 21
<212> TYPE: DNA
<213> ORGANISM: Artificial
<220> FEATURE:
<223> OTHER INFORMATION: Artificial siRNA designed to include antisense
      sequence for siRNA containing CAG repeats and include
      dideoxynucleotide thymidines

<400> SEQUENCE: 25
cugcugcugc ugcugcugct t                                             21

<210> SEQ ID NO 26
<211> LENGTH: 21
```

```
<212> TYPE: DNA
<213> ORGANISM: Artificial
<220> FEATURE:
<223> OTHER INFORMATION: Artificial non-toxic scaffold sequence for
      guide strand of artificial siRNA including dideoxynucleotide
      adenines
<220> FEATURE:
<221> NAME/KEY: misc_feature
<222> LOCATION: (2)..(7)
<223> OTHER INFORMATION: n is a, c, g, t or u

<400> SEQUENCE: 26
unnnnnnaca uguaaagcca a                                              21

<210> SEQ ID NO 27
<211> LENGTH: 21
<212> TYPE: DNA
<213> ORGANISM: Artificial
<220> FEATURE:
<223> OTHER INFORMATION: Artificial non-toxic scaffold sequence for
      passenger strand of artificial siRNA including dideoxynucleotide
      thymidines
<220> FEATURE:
<221> NAME/KEY: misc_feature
<222> LOCATION: (13)..(18)
<223> OTHER INFORMATION: n is a, c, g, t or u

<400> SEQUENCE: 27
cgguuuacau gunnnnnnat t                                              21
```

USE OF TRINUCLEOTIDE REPEAT RNAs TO TREAT CANCER

CROSS-REFERENCE TO RELATED PATENT APPLICATIONS

This application is a continuation of U.S. application Ser. No. 15/899,974 filed Feb. 20, 2018 which claims the benefit of priority under 35 U.S.C. § 119(e) to U.S. Provisional Application No. 62/596,457, filed on Dec. 8, 2017, to U.S. Provisional Application No. 62/531,991, filed on Jul. 13, 2017, and to U.S. Provisional Application No. 62/461,042, filed on Feb. 20, 2017, the contents of which are incorporated herein by reference in their entireties.

STATEMENT REGARDING FEDERALLY SPONSORED RESEARCH OR DEVELOPMENT

This invention was made with government support under R35 CA197450 awarded by the National Institutes of Health. The government has certain rights in the invention.

BACKGROUND

The field of the invention relates to RNA interference (RNAi) and the use of RNAi active sequences for treating diseases and disorders. In particular, the field of the invention relates to the use of toxic RNAi active sequences for killing cancer cells.

Cancer therapy is only marginally effective and not curative because tumor cells will often develop resistance and metastasize. This resistance is driven by the enhanced mutagenesis rate cancer cells experience and is particularly effective in circumventing drugs designed to target a single molecule or pathway.

We recently reported that siRNAs and shRNAs derived from CD95, CD95L (17) and other genes in the human genome (47) kill cancer cells through RNAi by targeting a network of critical survival genes (15,17). DISE ("death induced by survival gene elimination") was found to involve simultaneous activation of multiple cell death pathways and cancer cells have a hard time developing resistance to this form of cell death (16). DISE was found to preferentially affect transformed cells (16) and among them cancer stem cells (44). We can artificially induce DISE in cancer cells by introducing si/shRNAs that correspond to certain gene transcript sequences and by using artificially designed siRNAs that do not exist in nature optimized to induce DISE in cancer cells (15). In fact, treating tumor bearing mice with nanoparticle coupled DISE-inducing siRNAs resulted in reduced tumor growth with no toxicity to the mice. We hypothesized that DISE is part of a natural anticancer mechanism (15). We therefore wondered whether this mechanism could be accidentally triggered resulting in human pathology. Diseases that could be caused by overactive DISE would have to result in loss of various tissues and an RNA component would have to be involved in the disease pathology.

Here, we report that certain repeat sequences (CAG/CUG repeats) that are found to cause tissue loss in a number of degenerative diseases (i.e., Huntington's disease), are highly toxic to cancer cells by targeting multiple survival genes containing complementary trinucleotide repeat sequences. The significance of this discovery is that cancer cells would need to develop multiple concurring mutations to become resistant to this form of DISE because multiple death pathways are activated at once (17). Indeed, we have not found a single compound or knockdown of any gene that can rescue cancer cells from DISE and this DISE-like cell death preferentially affects cancer cells (17,44). Here we describe an entirely new way to kill cancer cells in vivo by introducing trinucleotide repeat derived siRNAs that preferentially target a large number of genes that are critical for the survival of cancer cells.

SUMMARY

Disclosed are polynucleotides, compositions, and methods related to RNA interference (RNAi). The disclosed polynucleotides, compositions, and methods may be utilized for treating diseases and disorders through RNAi.

Particularly disclosed are toxic RNAi active seed sequences and methods of using toxic RNAi active seed sequences for killing cancer cells. The disclosed toxic RNAi active seed sequences typically include trinucleotide RNA nucleotide repeats and preferentially target and inhibit the expression of multiple essential genes for cell survival and/or growth. The disclosed toxic RNAi active seed may be presented or administered in siRNAs, shRNAs, and/or vectors that express siRNAs and/or shRNAs.

BRIEF DESCRIPTION OF THE FIGURES

FIG. 1A. Sequence of the siCAG/CUG duplex. dA, deoxyadenosine.

FIG. 1B and FIG. 1C. Confluences over time of human (B) and mouse (C) cell lines transfected with 10 nM of either siNT, siL3, or siCAG/CUG. M565, 3LL and B 16F10 cells were reverse transfected. Values are mean−/+SEM. The 13 cell lines were tested between 1 and 6 times in each case with between 3 and 6 technical replicates.

FIG. 1D. Confluence over time of HCT116 cells transfected with either siNT or siCAG/CUG at 0.1 or 0.01 nM. Values are mean−/+SEM. n=2 biological replicates, 6 technical replicates each.

FIG. 1E. Viability (ATP content) of HeyA8 cells transfected with different concentrations of siNT, siL3 or siCAG/CUG. Values are mean−/+SD. n=3 biological replicates, 3 technical replicates each.

FIG. 2A. Confluence over time of HeyA8 (top) or A549 (bottom) cells transfected with 1 nM of either siNT or the four trinucleotide repeat (TNR) based siRNAs, siCAG/CUG, siCGG/CCG, siGAA/UUC and siCGA/UCG. Values are mean−/+SEM. n=3/2 biological replicates (HeyA8/A549), 8 technical replicates.

FIG. 2B. Results of toxicity screens of 60 TNR-based siRNAs in human HeyA8 (top) and mouse M565 (bottom) cells. Cells were reverse transfected in triplicate in 384 well plates with 1 nM of each siRNA. In all cases, the complementary (sense) strand was inactivated by a 2'-OMe modification in positions 1 and 2. Trinucleotide repeats were characterized as effecting: (i) no or less than 50% loss in viability; (ii) >50% loss in viability; or (iii) >75% loss in viability. Family 7 is the only family in which all 6 duplexes were super toxic. The six members of Family 5 have the same GC content and the same nucleotide composition as the members of family 7. Each family contains three TNRs in the forward frame (for) and three TNRs that are the reverse complement (rev) of these TNRs. Values are mean−/+SD. 3 technical replicates.

FIG. 2C. Correlation between the average of two viability screens performed in HeyA8 and two performed in M565 cells. The data points for the 6 members of TNR family 5 and family 7 are labeled. Pearson correlation and p-value is given.

FIG. 2D. Results of toxicity screen of 60 TNR-based 6 mer seeds in a nontoxic backbone siRNA (see FIG. 10B) in HeyA8 cells. Values are mean−/+SD. n=3 technical replicates.

FIG. 2E. Correlation between the average of two viability screens performed in HeyA8 with the 60 TNR based siRNAs and the screen performed with the 60 TNR based seeds. The data points for the 6 members of TNR family 7 and family 10 are labeled. Each member of family 7 effected <~20% viability and no member of family 10 effected <~75% viability. Pearson correlation and p-value is given.

FIG. 3A. Western blot analysis of HeyA8 and A549 cells treated with a control SmartPool (siCtr) or an AGO2 siRNA SmartPool for 48 hrs.

FIG. 3B. Confluence over time of HeyA8 and A549 cells after transfection with 1 nM siNT or siCAG/CUG. Cells were first transfected with either 25 nM of a Ctr SmartPool or the AGO2 SmartPool and then after 24 hrs transfected with siNT or siCAG/CUG. Values are mean−/+SEM. n=3 biological replicates, 3 technical replicates each.

FIG. 3C. Left: Sequences with positions of the 2'-O-methylation labeled in either the passenger/sense (S), the guide/antisense (AS) or both (A/AS) strands of siCAG/CUG. Right: Confluence over time of HeyA8 cells transfected with 10 nM of the four duplexes depicted on the left and two similarly modified duplexes derived from siNT. siCAG/CUG and siCAG (5-OMe) effected a significant reduction in % confluence. Values are mean−/+SEM. n=2 biological replicates, 4-6 technical replicates each.

FIG. 3D. Venn diagrams showing the overlap between 1185 survival genes (genes identified as critical survival genes in two genome-wide lethality screens [45, 46], blue) and genes significantly downregulated (red) in cells transfected with either siCAG/CUG (top) or siCGA/UCG (bottom) when compared to siNT.

FIG. 3E. Venn diagram comparing the 3466 genes downregulated in the siCAG/CUG treated HeyA8 cells (>1.5 fold adj. p<0.05) as determined by RNA-Seq (siCAG/CUG down) (see FIG. 3D) and the 1236 genes expression of which inversely correlate with the length of CAG repeats recently reported in HD patients (CAGnome down) [24].

FIGS. 4A and 4B. The toxicity of the TNR-based siRNAs correlates with the presence of long complementary repeats in the ORFs of genes.

FIG. 4A. Correlation between the average of the two viability screens performed in HeyA8 (top panels) or M565 (bottom panels) cells with the percentage of TNRs that are part of 6 mer or higher longer repeat sequences in either the ORF (left panels) or 3'UTR (right panel) of the genes. The data points for the 6 members of TNR family 5 are labeled in blue and those of family 7 are labeled in red. Pearson correlations and p-values are given.

FIG. 4B. The amino acids that are coded by the targeted trinucleotide repeats in families 5 and 7.

FIG. 5A. Left: Confluency over time of HeyA8 (Nuc-Red) cells treated with 10 nM of either siNT-TLP siL3-TLP, or siCAG/CUG-TLP. Right: Phase and red fluorescence image of HeyA8 (Nuc-Red) cells 90 hrs after transfection with 15 nM of TLPs. Values are mean−/+SEM. n=3 technical replicates.

FIG. 5B. Confluency over time of different human and mouse cancer cell lines treated with either 10 nM (OVCAR3, HepG2, M565) or 20 nM (A549, T98G) of TLPs. Values are mean−/+SEM. n=2 biological replicates, 6 technical replicates each.

FIG. 5C. Percent cell death (Trypan blue counting) of GIC-20 neurospheres derived from a patient with glioblastoma six days after adding the TLPs (30 nM). Values are mean−/+SD. n=3 technical replicates. **p<0.01.

FIG. 5D. Treatment scheme.

FIG. 5E. Tumor growth over time based on small animal imaging of $10^5$ HeyA8-Nuc-red-Luc-neo cells injected i.p. into NSG mice treated with either siNT-TLPs or siCAG/CUG-TLPs. Treatment group 1 received 18 injections over four weeks and treatment group 2 10 injections over three weeks. The bioluminescence signal of IVIS #4 and #5 for individual mice is shown (right panel). The experiment represents one of two similar experiments. Values are mean−/+SD. *p<0.05; p<0.01; *p<0.0001, NS, not significant.

FIG. 5F and FIG. 5G. Change in red object count (growth) of tumor cells from 3 mice of the siNT-TLP and the siCAG/CUG-TLP treatment group 1 either after transfection with 1 nM siNT or siCAG/CUG (F) or after incubation with 7.5 nM siNT-TLP or siCAG/CUG-TLP (G). 1000 cells per well were plated. Values are mean−/+SEM. n=3-8 technical replicates.

FIG. 6A. Left: DNA fragmentation in HeyA8 and A549 cells 120/72 hours after transfection with indicated siRNAs. n=3-4 technical replicates. Right: Viability of human and mouse cell lines 96 hours after transfection with the indicated siRNAs. Values are mean−/+SD. n=2 biological replicates, 3 technical replicates each.

FIG. 6B. Human and mouse cell lines transfected with either siNT or siCAG/CUG. Time points after transfection of picture taking is given. Size bar=100 μm.

FIG. 10A. Left: Scheme showing the different mutant siNT and siL3 duplexes used. The four light blue boxes indicate the four positions that in the nontargeting siRNA (siNT) were identical to the same positions in siL3. In siL3 the seed sequence is shown as a green box, and the siNT seed sequence is shown as a grey box. siNT/siL3 is a chimeric duplex comprised of the seed sequence of siL3 and the rest of siNT. In the siL3 seed duplex, the four siL3 positions in siNT were replaced with the complementary nucleotides (i.e. an G:C was changed to a C:G). Right: Confluence over time of HeyA8 cells transfected with 10 nM of the five duplexes depicted on the left. Values are mean−/+SEM. n=6 technical replicates.

FIG. 10B. Schematic showing the design of the seed siRNAs tested in FIG. 2D. Y and Z indicate the Watson-Crick complementary nucleotides of the 6 mer seed. The two red Xs indicate the position of the 2'O-methylation in the passenger strand.

FIG. 12A. Sensitivity of mouse embryonic stem cells to siCAG/CUG lacking expression of all four AGO proteins with the same cells in which we rendered the RISC functional by re-expression of human AGO2. Western blot analysis of Ago1-4 k.o. mouse embryonic stem cells expressing a Tet inducible AGO2 protein. Lanes are as follows: 1: Low Dox; 2: 4 days without Dox; 3: 3 days without Dox—1 day with high Dox; 4: 3 days without Dox—1 day with high Dox—1 day without Dox; 5: 3 days without Dox—1 day with high Dox—2 days without Dox; 6: 3 days without Dox—1 day with high Dox—3 days without Dox; 7: 3 days without Dox—1 day with high Dox—4 days without Dox; 8: 3 days without Dox—1 day with high Dox—7 days without Dox. Low Dox=0.1 µg/ml; high Dox=2.5 µg/ml. n=2 biological replicates.

FIG. 12B. Confluence over time of Ago1-4 k.o. cells with induced AGO2 with high Dox (left) or without Dox (right) after transfection with 5 nM siNT or siCAG/CUG. Two-way ANOVA is given. Equal transfection efficiency was established by transfecting cells with 5 nM of either siNT or 5'Cy5 labeled siNT followed by FACS analysis (inserts). Values are mean−/+SEM. n=3 biological replicates, 4 technical replicates each. AGO2 expressing Ago1-4 k.o. ESCs over-expressing human AGO2 showed a very low but reproducible susceptibility to siCAG/CUG. In contrast, Ago1-4 k.o. cells were completely resistant to this form of toxicity, despite similar transfection efficiencies (see inserts) between Ago1-4 k.o. cells and those expressing AGO2. The low sensitivity of the Ago1-4 k.o./AGO2 cells could either be due to normal cells being less sensitive to this form of cell death or could point at a functional role of Ago family members other than Ago2 in this process.

FIG. 14A. Venn diagram of human and mouse ORFs and 3'UTRs containing the CAG (left) or CGA (right) trinucleotide repeats.

FIG. 14B. Venn diagram of human and mouse ORFs and 3'UTRs containing the 19 mer sequences completely complementary to the CAG (left) or CGA (right) based 19 mer.

FIGS. 15A-C. No adverse effects in mice treated with siCAG/CUG-TLPs.

FIG. 15A. Weight of the ten mice in treatment group 1 (see FIG. 5D) over the course of the treatment. Values are mean−/+SD. NS, unpaired p-value not significant.

FIG. 15B. H&E stained liver sections of two of the mice that were treated with either siNT-TLP or siCAG/CUG-TLP on day 27 in the experiment shown in FIG. 5E).

FIG. 15C. Serum analysis of the same two mice per treatment group. 1=Sample assay value is less than the dynamic range. For most assays, the dynamic range low limit is reported. 2=Sample was diluted for testing. Assay value for sample was below dynamic range, but results have been corrected for dilution. 3=Assay is a calculated value. Either or both assay values used in the calculation were below the dynamic range of the assay, therefore no result is reported.

DETAILED DESCRIPTION

Figure 1A:
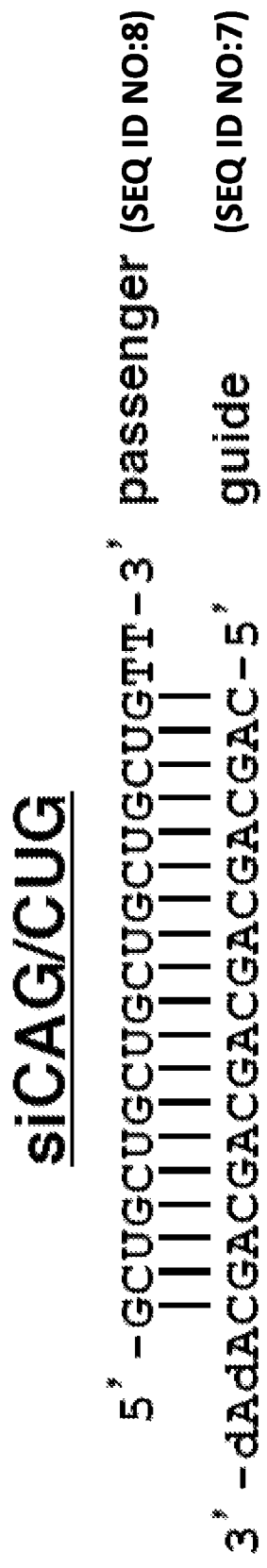
FIGS. 1A-E. An siRNA duplex comprised of CAG and CUG repeats is super toxic to various cancer cell lines of human and mouse origin.

The present invention is described herein using several definitions, as set forth below and throughout the application.

Unless defined otherwise, all technical and scientific terms used herein have the same meaning as commonly understood by one of skill in the art to which the invention pertains. All definitions, as defined and used herein, should be understood to control over dictionary definitions, definitions in documents incorporated by reference, and/or ordinary meanings of the defined terms.

Unless otherwise specified or indicated by context, the terms "a", "an", and "the" should be interpreted to mean "one or more." For example, "an shRNA" or "an siRNA" should be interpreted to mean "one or more shRNA's" and "one or more siRNA's," respectively As used herein, "about," "approximately," "substantially," and "significantly" will be understood by persons of ordinary skill in the art and will vary to some extent on the context in which they are used. If there are uses of these terms which are not clear to persons of ordinary skill in the art given the context in which they are used, "about" and "approximately" should be interpreted to mean plus or minus ≤10% of the particular term and "substantially" and "significantly" should be interpreted to mean plus or minus >10% of the particular term.

As used herein, the terms "include" and "including" should be interpreted to have the same meaning as the terms "comprise" and "comprising" in that these latter terms are "open" transitional terms that do not limit claims only to the recited elements succeeding these transitional terms. The term "consisting of," while encompassed by the term "comprising," should be interpreted as a "closed" transitional term that limits claims only to the recited elements succeeding this transitional term. The term "consisting essentially of," while encompassed by the term "comprising," should be interpreted as a "partially closed" transitional term which permits additional elements succeeding this transitional term, but only if those additional elements do not materially affect the basic and novel characteristics of the claim.

A range includes each individual member. Thus, for example, a group having 1-3 members refers to groups having 1, 2, or 3 members.

It should also be understood that, unless clearly indicated to the contrary, in any methods claimed herein that include more than one step or act, the order of the steps or acts of the method is not necessarily limited to the order in which the steps or acts of the method are recited.

The modal verb "may" refers to the preferred use or selection of one or more options or choices among the several described embodiments or features contained within the same. Where no options or choices are disclosed regarding a particular embodiment or feature contained in the same, the modal verb "may" refers to an affirmative act regarding how to make or use an aspect of a described embodiment or feature contained in the same, or a definitive decision to use a specific skill regarding a described embodiment or feature contained in the same. In this latter context, the modal verb "may" has the same meaning and connotation as the auxiliary verb "can."

As used herein, a "subject" may be interchangeable with "patient" or "individual" and means an animal, which may be a human or non-human animal, in need of treatment.

A "subject in need of treatment" may include a subject having a disease, disorder, or condition that can be treated by administering to the subject one or more therapeutic RNAs as disclosed herein. A subject in need thereof may include a subject having or at risk for developing a cell proliferative disease or disorder such as cancer. A subject in need thereof may include, but is not limited to, a subject having or at risk for developing any of adenocarcinoma, leukemia, lymphoma, melanoma, myeloma, sarcoma, and teratocarcinoma, (including cancers of the adrenal gland, bladder, bone, bone marrow, brain, breast, cervix, gall bladder, ganglia, gastrointestinal tract, heart, kidney, liver, lung, muscle, ovary, pancreas, parathyroid, prostate, skin, testis, thymus, and uterus). As such, methods of treating cancers are contemplated herein, including methods of treating cancers selected from, but not limited to any of adenocarcinoma, leukemia, lymphoma, melanoma, myeloma, sarcoma, and teratocarcinoma, (including cancers of the adrenal gland, bladder, bone, bone marrow, brain, breast, cervix, gall bladder, ganglia, gastrointestinal tract, heart, kidney, liver, lung, muscle, ovary, pancreas, parathyroid, prostate, skin, testis, thymus, and uterus).

The disclosed technology relates to nucleic acid and the use of nucleic acid for treated diseases and disorders. The terms "nucleic acid" and "oligonucleotide," as used herein, refer to polydeoxyribonucleotides (containing 2-deoxy-ribose), polyribonucleotides (containing ribose), and to any other type of polynucleotide that is an N glycoside of a purine or pyrimidine base. As used herein, the terms "A," "T," "C", "G" and "U" refer to adenine, thymine, cytosine, guanine, uracil as a nucleotide base, respectively. There is no intended distinction in length between the terms "nucleic acid," "oligonucleotide," and "polynucleotide," and these terms will be used interchangeably. These terms refer only to the primary structure of the molecule. Thus, these terms include double- and single-stranded DNA, as well as double- and single-stranded RNA. For use in the present invention, an oligonucleotide also can comprise nucleotide analogs in which the base, sugar or phosphate backbone is modified as well as non-purine or non-pyrimidine nucleotide analogs.

A "fragment" of a polynucleotide is a portion of a polynucleotide sequence which is identical in sequence to but shorter in length than a reference sequence. A fragment may comprise up to the entire length of the reference sequence, minus at least one nucleotide. For example, a fragment may comprise from 5 to 1000 contiguous nucleotides of a reference polynucleotide. In some embodiments, a fragment may comprise at least 5, 10, 15, 20, 25, 30, 40, 50, 60, 70, 80, 90, 100, 150, 250, or 500 contiguous nucleotides of a reference polynucleotide; in other embodiments a fragment may comprise no more than 5, 10, 15, 20, 25, 30, 40, 50, 60, 70, 80, 90, 100, 150, 250, or 500 contiguous nucleotides of a reference polynucleotide; in further embodiments a fragment may comprise a range of contiguous nucleotides of a reference polynucleotide bounded by any of the foregoing values (e.g. a fragment comprising 20-50 contiguous nucleotides of a reference polynucleotide). Fragments may be preferentially selected from certain regions of a molecule. The term "at least a fragment" encompasses the full length polynucleotide. A "variant," "mutant," or "derivative" of a reference polynucleotide sequence may include a fragment of the reference polynucleotide sequence.

Regarding polynucleotide sequences, percent identity may be measured over the length of an entire defined polynucleotide sequence, for example, as defined by a particular SEQ ID number, or may be measured over a shorter length, for example, over the length of a fragment taken from a larger, defined sequence, for instance, a fragment of at least 20, at least 30, at least 40, at least 50, at least 70, at least 100, or at least 200 contiguous nucleotides. Such lengths are exemplary only, and it is understood that any fragment length supported by the sequences shown herein, in the tables, figures, or Sequence Listing, may be used to describe a length over which percentage identity may be measured.

Regarding polynucleotide sequences, "variant," "mutant," or "derivative" may be defined as a nucleic acid sequence having at least 50% sequence identity to the particular nucleic acid sequence over a certain length of one of the nucleic acid sequences using blastn with the "BLAST 2 Sequences" tool available at the National Center for Biotechnology Information's website. (See Tatiana A. Tatusova, Thomas L. Madden (1999), "Blast 2 sequences—a new tool for comparing protein and nucleotide sequences", FEMS Microbiol Lett. 174:247-250). Such a pair of nucleic acids may show, for example, at least 20%, at least 30%, at least 40%, at least 50%, at least 60%, at least 70%, at least 80%, at least 85%, at least 90%, at least 91%, at least 92%, at least 93%, at least 94%, at least 95%, at least 96%, at least 97%, at least 98%, or at least 99% or greater sequence identity over a certain defined length.

A "recombinant nucleic acid" is a sequence that is not naturally occurring or has a sequence that is made by an artificial combination of two or more otherwise separated segments of sequence. This artificial combination is often accomplished by chemical synthesis or, more commonly, by the artificial manipulation of isolated segments of nucleic acids, e.g., by genetic engineering techniques known in the art. The term recombinant includes nucleic acids that have been altered solely by addition, substitution, or deletion of a portion of the nucleic acid. Frequently, a recombinant nucleic acid may include a nucleic acid sequence operably linked to a promoter sequence. Such a recombinant nucleic acid may be part of a vector that is used, for example, to transform a cell.

The nucleic acids disclosed herein may be "substantially isolated or purified." The term "substantially isolated or purified" refers to a nucleic acid that is removed from its natural environment, and is at least 60% free, preferably at least 75% free, and more preferably at least 90% free, even more preferably at least 95% free from other components with which it is naturally associated.

Oligonucleotides can be prepared by any suitable method, including direct chemical synthesis by a method such as the phosphotriester method of Narang et al., 1979, Meth. Enzymol. 68:90-99; the phosphodiester method of Brown et al., 1979, Meth. Enzymol. 68:109-151; the diethylphosphoramidite method of Beaucage et al., 1981, Tetrahedron Letters 22:1859-1862; and the solid support method of U.S. Pat. No. 4,458,066, each incorporated herein by reference. A review of synthesis methods of conjugates of oligonucleotides and modified nucleotides is provided in Goodchild, 1990, Bioconjugate Chemistry 1(3): 165-187, incorporated herein by reference.

The term "promoter" as used herein refers to a cis-acting DNA sequence that directs RNA polymerase and other trans-acting transcription factors to initiate RNA transcription from the DNA template that includes the cis-acting DNA sequence.

As used herein, the term "complementary" in reference to a first polynucleotide sequence and a second polynucleotide sequence means that the first polynucleotide sequence will base-pair exactly with the second polynucleotide sequence throughout a stretch of nucleotides without mismatch. The term "cognate" may in reference to a first polynucleotide sequence and a second polynucleotide sequence means that the first polynucleotide sequence will base-pair with the second polynucleotide sequence throughout a stretch of nucleotides but may include one or more mismatches within the stretch of nucleotides. As used herein, the term "complementary" may refer to the ability of a first polynucleotide to hybridize with a second polynucleotide due to base-pair interactions between the nucleotide pairs of the first polynucleotide and the second polynucleotide (e.g., A:T, A:U, C:G, G:C, G:U, T:A, U:A, and U:G).

As used herein, the term "complementarity" may refers to a sequence region on an anti-sense strand that is substantially complementary to a target sequence but not fully complementary to a target sequence. Where the anti-sense strand is not fully complementary to the target sequence, mismatches may be optionally present in the terminal regions of the anti-sense strand or elsewhere in the anti-sense strand. If mismatches are present, optionally the mismatches may be present in terminal region or regions of the anti-sense strand (e.g., within 6, 5, 4, 3, or 2 nucleotides of the 5' and/or 3' terminus of the anti-sense strand).

The term "hybridization," as used herein, refers to the formation of a duplex structure by two single-stranded nucleic acids due to complementary base pairing. Hybridization can occur between fully complementary nucleic acid strands or between "substantially complementary" nucleic acid strands that contain minor regions of mismatch. Conditions under which hybridization of fully complementary nucleic acid strands is strongly preferred are referred to as "stringent hybridization conditions" or "sequence-specific hybridization conditions." Stable duplexes of substantially complementary sequences can be achieved under less stringent hybridization conditions; the degree of mismatch tolerated can be controlled by suitable adjustment of the hybridization conditions. Those skilled in the art of nucleic acid technology can determine duplex stability empirically considering a number of variables including, for example, the length and base pair composition of the oligonucleotides, ionic strength, and incidence of mismatched base pairs, following the guidance provided by the art (see, e.g., Sambrook et al., 1989, Molecular Cloning—A Laboratory Manual, Cold Spring Harbor Laboratory, Cold Spring Harbor, New York; Wetmur, 1991, Critical Review in Biochem. and Mol. Biol. 26(3/4):227-259; and Owczarzy et al., 2008, Biochemistry, 47: 5336-5353, which are incorporated herein by reference).

As used herein, the term "double-stranded RNA" ("dsRNA") refers to a complex of ribonucleic acid molecules having a duplex structure comprising two anti-parallel and substantially complementary nucleic acid strands.

As used herein, the term "nucleotide overhang" refers to an unpaired nucleotide or nucleotides that extend from the 5'-end or 3'-end of a duplex structure of a dsRNA when a 5'-end of one strand of the dsRNA extends beyond the 3'-end of the other strand, or when a 3'-end of one strand of the dsRNA extends beyond the 5'-end of the other strand.

As used herein, the term "blunt" refers to a dsRNA in which there are no unpaired nucleotides at the 5'-end and/or the 3'-end of the dsRNA (i.e., no nucleotide overhang at the 5'-end or the 3'-end). A "blunt ended" dsRNA is a dsRNA that has no nucleotide overhang at the 5'-end or the 3'-end of the dsRNA molecule.

As used herein, the term "anti-sense strand" refers to a strand of a dsRNA which includes a region that is substantially complementary to a target sequence (i.e., where the target sequence has a sequence corresponding to the sense strand).

As used herein, the term "sense strand," refers to the strand of a dsRNA that includes a region that is substantially complementary to a region of the anti-sense strand and that includes a region that substantially corresponds to a region of the target sequence.

As used herein, RNAi active sequences may include "siRNA" and "shRNA" and dsRNA that is processed by nucleases to provide siRNA and/or shRNA. The term "siRNA" refers to a "small interfering RNA" and the term "shRNA" refers to "short hairpin RNA." RNA interference (RNAi) refers to the process of sequence-specific post-transcriptional gene silencing in a cell or an animal mediated by siRNA and/or shRNA.

As used herein, the term "siRNA targeted against mRNA" refers to siRNA specifically promote degradation of the targeted mRNA via sequence-specific complementary multiple base pairings (e.g., at least 6 contiguous base-pairs between the siRNA and the target mRNA at optionally at least 7, 8, 9, 10, 11, 12, 13, 14, 15, 16, 17, 18, 19, 20, 21, 22, or 23 contiguous base-pairs between the siRNA and the target mRNA).

The terms "target, "target sequence", "target region", and "target nucleic acid," as used herein, are synonymous and refer to a region or sequence of a nucleic acid which may be selected as a sequence to which the anti-sense strand of siRNA or shRNA is substantially complementary to and hybridizes to as discussed herein. A target sequence may refer to a contiguous portion of a nucleotide sequence of an mRNA molecule of a particular gene, including but not limited to, genes that are essential for survival and/or growth of cells and in particular cancer cells. The target sequence of a siRNA refers to a mRNA sequence of a gene that is targeted by the siRNA due to complementarity between the anti-sense strand of the siRNA and the mRNA sequence and to which the anti-sense strand of the siRNA hybridizes when brought into contact with the mRNA sequence.

As used herein, the term "transfecting" means "introducing into a cell" a molecule, which may include a polynucleotide molecule such as dsRNA. When referring to a dsRNA, transfecting means facilitating uptake or absorption into the cell, as is understood by the skilled person. Absorption or uptake of dsRNA can occur or may be facilitated through passive diffusive or active cellular processes, or through the use of auxiliary agents or devices. Transfection into a cell includes methods known in the art such as electroporation and lipofection. However, the meaning of the term "transfection" is not limited to introducing molecules into cells in vitro. As contemplated herein, a dsRNA also may be "introduced into a cell," where the cell is part of a living organism. For example, for in vivo delivery, a dsRNA may be injected into a tissue site or may be administered systemically.

As used herein, the terms "silencing" and "inhibiting the expression of" refer to at least partial suppression of the expression of a target gene, for example, as manifested by a reduction of mRNA associated with the target gene.

As used herein, the phrase "effective amount" shall mean that drug dosage that provides the specific pharmacological response for which the drug is administered in a significant number of patients in need of such treatment. An effective amount of a drug that is administered to a particular patient in a particular instance will not always be effective in treating the conditions/diseases described herein, even though such dosage is deemed to be a therapeutically effective amount by those of skill in the art.

As used herein, the term "pharmaceutical composition" may include be defined as a composition that includes a pharmacologically effective amount of a dsRNA and a pharmaceutically acceptable carrier for delivering the dsRNA to target cells or target tissue. As used herein, the term "pharmaceutically acceptable carrier" refers to a carrier for administration of a therapeutic agent which facilitates the delivery of the therapeutic agent (e.g., dsRNA) to target cells or target tissue. As used herein, the term "therapeutically effective amount" refers to that amount of a therapeutic agent that provides a therapeutic benefit in the treatment, prevention, or management of a disease or disorder (e.g., a cell proliferation disease or disorder such as cancer).

In one aspect, the present inventors disclose an isolated double stranded short interfering ribonucleic acid (siRNA) molecule or small hairpin ribonucleotide acid (shRNA) molecule that silences expression of one or more mRNA's of essential genes that are required for survival and growth of cells such as cancer cells. Preferably, the disclosed siRNA molecules or shRNA molecules silence the expression of multiple mRNA's of essential genes that are required for survival and growth of cells such as cancer cells through a process similar to the process called "death-induced by survival gene elimination" or "DISE."

The mechanism of action of siRNA and shRNA is understood by the skilled person. Interfering RNA (RNAi) generally refers to a single-stranded RNA (ssRNA) or double-stranded RNA (dsRNA). The dsRNA is capable of targeting specific messenger RNA (mRNA) and silencing (i.e., inhibiting) the expression of a target gene. During this process, dsRNA (which may include shRNA) is enzymatically processed into short-interfering RNA (siRNA) duplexes of ~21-23 nucleotides in length. The anti-sense strand of the siRNA duplex is then incorporated into a cytoplasmic complex of proteins (RNA-induced silencing complex or RISC). The RISC complex containing the anti-sense siRNA strand also binds mRNA which has a sequence complementary to the anti-sense strand-allowing complementary base-pairing between the anti-sense siRNA strand and the sense mRNA molecule. The mRNA molecule is then specifically cleaved by an enzyme (RNase) associated with RISC resulting in specific gene silencing. For gene silencing or knock down (i.e., mRNA cleavage) to occur, anti-sense RNA (e.g., siRNA) has to become incorporated into the RISC. This represents an efficient process that occurs in nucleated cells during regulation of gene expression.

As such, siRNA-mediated RNA interference may be considered to involve two-steps: (i) an initiation step, and (ii) an effector step. In the first step, input siRNA is processed into small fragments, such as ~21-23-nucleotide 'guide sequences.' The guide RNAs can be incorporated into the protein-RNA RISC complex which is capable of degrading mRNA. As such, the RISC complex acts in the second effector step to destroy mRNAs that are recognized by the guide RNAs through base-pairing interactions. RNA interference via use of siRNA may be considered to involve the introduction by any means of double stranded RNA into a cell which triggers events that cause the degradation of a target RNA, and as such siRNA may be considered to be a form of post-transcriptional gene silencing. The skilled person understands how to prepare and utilize siRNA molecules. (See, e.g., Hammond et al., Nature Rev Gen 2: 110-119 (2001); and Sharp, Genes Dev 15: 485-490 (2001), the contents of which are incorporate herein by reference in their entireties).

For purposes of this application, the anti-sense strand of the disclosed RNA molecules (e.g., siRNA molecules) may comprise a contiguous nucleotide sequence, where the base sequence of the anti-sense strand has substantial or complete sequence complementarity to the base sequence of a contiguous nucleotide sequence of corresponding length contained in an mRNA sequence of the targeted mRNA (e.g., in a non-coding 3'-end of an mRNA sequence). Substantial complementary permits some nucleotide mismatches (i.e., non-pairing nucleotides) and as such, the anti-sense strand of the siRNA need not have full complementarity.

In some embodiments, at least a portion of an anti-sense strand of the disclosed RNA molecules (e.g., siRNA molecules) comprises or consists of a sequence that is 100% complementary to a target sequence or a portion thereof. In another embodiment, at least a portion of an anti-sense strand of an siRNA molecule comprises or consists of a sequence that is at least about 90%, 95%, or 99% complementary to a target sequence or a portion thereof. For purposes of this application, the anti-sense strand of the disclosed RNA molecules (e.g., siRNA molecules) preferably comprises or consists of a sequence that specifically hybridizes to a target sequence or a portion thereof so as to inhibit expression of the target mRNA.

In some embodiments, the disclosed RNAs, including siRNAs administered in RNAi therapy, may include repeat sequences. For example, in some embodiments, the disclosed RNAs may include trinucleotide repeats such as any of: $(AAA)_n$, $(AAC)_n$, $(AAG)_n$, $(AAU)_n$, $(ACA)_n$, $(ACC)_n$, $(ACG)_n$, $(ACU)_n$, $(AGA)_n$, $(AGC)_n$, $(AGG)_n$, $(AGU)_n$, $(AUA)_n$, $(AUC)_n$, $(AUG)_n$, $(AUU)_n$, $(CAA)_n$, $(CAC)_n$, $(CAG)_n$, $(CAU)_n$, $(CCA)_n$, $(CCC)_n$, $(CCG)_n$, $(CCU)_n$, $(CGA)_n$, $(CGC)_n$, $(CGG)_n$, $(CGU)_n$, $(CUA)_n$, $(CUC)_n$, $(CUG)_n$, $(CUU)_n$, $(GAA)_n$, $(GAC)_n$, $(GAG)_n$, $(GAU)_n$, $(GCA)_n$, $(GCC)_n$, $(GCG)_n$, $(GCU)_n$, $(GGA)_n$, $(GGC)_n$, $(GGG)_n$, $(GGU)_n$, $(GUA)_n$, $(GUC)_n$, $(GUG)_n$, $(GUU)_n$, $(UAA)_n$, $(UAC)_n$, $(UAG)_n$, $(UAU)_n$, $(UCA)_n$, $(UCC)_n$, $(UCG)_n$, $(UCU)_n$, $(UGA)_n$, $(UGC)_n$, $(UGG)_n$, $(UGU)_n$, $(UUA)_n$, $(UUC)_n$, $(UUG)_n$, and $(UUU)_n$, where n is an integer, typically selected from 3, 4, 5, 6, 7, 8, 9, 10, 11, 12, 13, 14, 15, to about 100 or higher. Preferably, the disclosed RNAs may include trinucleotide repeats such as any of: $(AGC)_n$, $(CAG)_n$, $(CUG)_n$, $(GCA)_n$, $(GGU)_n$, and $(UGC)_n$, where n is an integer, typically selected from 3, 4, 5, 6, 7, 8, 9, 10, 11, 12, 13, 14, 15, to about 100 or higher.

Methods for preparing and isolating siRNA also are known in the art. (See, e.g., Sambrook et al., Molecular Cloning, A Laboratory Manual (2.sup.nd Ed., 1989), the content of which is incorporated herein by reference in its entirety). The disclosed siRNA may be chemically synthesized, using any of a variety of techniques known in the art. The disclosed siRNA may include modifications, for example, modifications that stabilize the siRNA and/or protect the siRNA from degradation via endonucleases and/or exonucleases. In some embodiments, the disclosed siRNA may include nucleic acid protecting and coupling groups, such as dimethoxytrityl at the 5'-end and/or phosphoramidites at the 3'-end.

In one embodiment, the disclosed RNAs comprise a double stranded region of about 15 to about 30 nucleotides in length. Preferably, the disclosed RNAs are about 20-25 nucleotides in length. The disclosed RNAs of the present invention are capable of silencing the expression of a target sequence in vitro and in vivo.

In one embodiment, the dsRNA disclosed herein comprises a hairpin loop structure and may be referred to as shRNA which may be processed to a siRNA. In another embodiment, the dsRNA or siRNA has an overhang on its 3' or 5' ends relative to the target RNA which is to be cleaved. The overhang may be 2-10 nucleotides long. In one embodiment, the dsRNA or siRNA does not have an overhang (i.e., the dsRNA or siRNA has blunt ends).

In another embodiment, the disclosed RNA molecules (e.g., siRNA molecules) may contain one or more modified nucleotides, including one or more modified nucleotides at the 5' and/or 3' terminus of the RNA molecules. In yet another embodiment, the disclosed RNA molecules may comprise one, two, three four or more modified nucleotides in the double-stranded region. Exemplary modified nucleotides may include but are not limited to, modified nucleotides such as 2'-O-methyl (2'OMe) nucleotides, 2'-deoxy-2'-fluoro (2'F) nucleotides, 2'-deoxy nucleotides, 2'-O-(2-methoxyethyl) (MOE) nucleotides, and the like. The preparation of modified siRNA is known by one skilled in the art. In some embodiments, the disclosed dsRNA molecules include one or more modified nucleotides at the 5'-terminus of the passenger strand of the dsRNA that prevent incorporation of the passenger strand into RISC. (See, e.g., Walton et al., Minireview: "Designing highly active siRNAs for therapeutic applications," the FEBS Journal, 277 (2010) 4806-4813).

In some embodiments, the disclosed RNA molecules are capable of silencing one or more target mRNAs and may reduce expression of the one or more target mRNAs by at least about 20%, 30%, 40%, 50%, 60%, 70%, 80%, 90%, or 100% relative to a control RNA molecule (e.g., a molecule not exhibiting substantial complementarity with the target mRNA). As such, in some embodiments, the presently disclosed RNA molecules targeting the mRNA of essential genes may be used to down-regulate or inhibit the expression of essential genes (e.g., by at least about 20%, 30%, 40%, 50%, 60%, 70%, 80%, 90%, or 100% relative to a control RNA molecule).

The disclosed RNA molecules may conveniently be delivered to a target cell or a target tissue through a number of delivery systems. For example, RNA may be delivered via electroporation, lipofection, calcium phosphate precipitation, plasmids, viral vectors that express the RNA, viral nucleic acids, phage nucleic acids, phages, cosmids, nanoparticles, or via transfer of genetic material in cells or carriers such as cationic liposomes. In one embodiment, transfection of RNA may employ viral vectors, chemical transfectants, or physico-mechanical methods such as electroporation and direct diffusion of DNA.

Also disclosed herein are pharmaceutical compositions (e.g., pharmaceutical compositions comprising therapeutic RNA) and methods of administering pharmaceutical compositions for treating diseases and disorders (e.g., cell proliferative diseases and disorders such as cancer). The pharmaceutical composition may comprise one or more RNAs as therapeutic agents for inhibiting the gene activity of one or more essential genes and a pharmaceutical acceptable carrier. Pharmaceutically acceptable carriers include, but are not limited to, excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Pharmaceutical compositions containing RNA may be administered to a mammal in vivo to treat cancer. In one embodiment, the pharmaceutical formulation includes a dosage suitable for oral administration. In another embodiment, the pharmaceutical formulation is designed to suit various means for RNA administration. Exemplary means include uptake of naked RNA, liposome fusion, intramuscular injection via a gene gun, endocytosis and the like.

Toxic RNAi Active Sequence for Killing Cancer Cells

Disclosed herein are polynucleotide sequences that may be utilized in therapeutic methods of killing cancer cells in a subject in need thereof. The disclosed polynucleotide sequences may be referred to as "toxic RNAi active sequences." Particularly disclosed are toxic RNAi active sequences such as siRNA and shRNA and methods of using toxic RNAi active sequence for killing cancer cells. The disclosed toxic RNAi active sequences typically include trinucleotide repeats and preferentially target and inhibit the expression of multiple essential genes for cell survival and/or growth through a process similar to the process called "death-induced by survival gene elimination" or "DISE."

In some embodiments, the disclosed polynucleotide sequences include nucleotide trinucleotide repeats such as any of: $(AAA)_n$, $(AAC)_n$, $(AAG)_n$, $(AAU)_n$, $(ACA)_n$, $(ACC)_n$, $(ACG)_n$, $(ACU)_n$, $(AGA)_n$, $(AGC)_n$, $(AGG)_n$, $(AGU)_n$, $(AUA)_n$, $(AUC)_n$, $(AUG)_n$, $(AUU)_n$, $(CAA)_n$, $(CAC)_n$, $(CAG)_n$, $(CAU)_n$, $(CCA)_n$, $(CCC)_n$, $(CCG)_n$, $(CCU)_n$, $(CGA)_n$, $(CGC)_n$, $(CGG)_n$, $(CGU)_n$, $(CUA)_n$, $(CUC)_n$, $(CUG)_n$, $(CUU)_n$, $(GAA)_n$, $(GAC)_n$, $(GAG)_n$, $(GAU)_n$, $(GCA)_n$, $(GCC)_n$, $(GCG)_n$, $(GCU)_n$, $(GGA)_n$, $(GGC)_n$, $(GGG)_n$, $(GGU)_n$, $(GUA)_n$, $(GUC)_n$, $(GUG)_n$, $(GUU)_n$, $(UAA)_n$, $(UAC)_n$, $(UAG)_n$, $(UAU)_n$, $(UCA)_n$, $(UCC)_n$, $(UCG)_n$, $(UCU)_n$, $(UGA)_n$, $(UGC)_n$, $(UGG)_n$, $(UGU)_n$, $(UUA)_n$, $(UUC)_n$, $(UUG)_n$, $(UUU)_n$, where n is an integer, typically selected from 3, 4, 5, 6, 7, 8, 9, 10, 11, 12, 13, 14, 15, to about 100 or higher. Preferably, the disclosed toxic RNAi active sequences may include trinucleotide repeats such as any of: $(AGC)_n$, $(CAG)_n$, $(CUG)_n$, $(GCA)_n$, $(GGU)_n$, and $(UGC)_n$, where n is an integer, typically selected from 3, 4, 5, 6, 7, 8, 9, 10, 11, 12, 13, 14, 15, to about 100 or higher. For example, the disclosed toxic RNAi active sequences may include the nucleotide repeat $(CAG)_n$ or $(CUG)_n$, where n is 3, 4, 5, 6, 7, 8, 9, 10, 11, 12, 13, 14, 15, to about 100 or higher.

In some embodiments, the disclosed polynucleotide sequences comprise a passenger strand and a guide strand, and may include siRNAs and/or shRNAs. The disclosed polynucleotide sequences also optionally and preferably comprise: (i) an RNA nucleotide trinucleotide repeat sequence $(X_1X_2X_3)_n$, wherein $X_1$, $X_2$, and $X_3$ independently are selected from any ribonucleotide A, C, G, and U, and n is an integer from 3-10; and where optionally and preferably (ii) one or more modified nucleotides at the 5'-terminus of the passenger strand that prevents loading of the passenger strand into the RNA-induced silencing complex (RISC). Preferably, the RNA trinucleotide repeat sequence has a GC content of at least 66%.

In some embodiments, the trinucleotide repeat sequence of the disclosed polynucleotide sequences is selected from the group consisting of $(ACC)_n$, $(ACG)_n$, $(AGC)_n$, $(AGG)_n$, $(CAC)_n$, $(CAG)_n$, $(CCA)_n$, $(CCC)_n$, $(CCG)_n$, $(CCU)_n$, $(CGA)_n$, $(CGC)_n$, $(CGG)_n$, $(CGU)_n$, $(CUC)_n$, $(CUG)_n$, $(GAC)_n$, $(GAG)_n$, $(GCA)_n$, $(GCC)_n$, $(GCG)_n$, $(GCU)_n$, $(GGA)_n$, $(GGC)_n$, $(GGG)_n$, $(GGU)_n$, $(GUC)_n$, $(GUG)_n$, $(UCC)_n$, $(UCG)_n$, $(UGC)_n$, and $(UGG)_n$. Preferably, the trinucleotide repeat sequence of the disclosed polynucleotide sequences is selected from the group consisting of $(AGC)_n$, $(CAG)_n$, $(CUG)_n$, $(GCA)_n$, $(GGU)_n$, and $(UGC)_n$, where n is an integer, typically selected from 3, 4, 5, 6, 7, 8, 9, 10, 11, 12, 13, 14, 15, to about 100 or higher. Particularly, in some embodiments, the trinucleotide repeat sequence of the disclosed polynucleotide sequences is CAG or CUG and is present in the guide strand.

Typically, the disclosed polynucleotide sequences comprise one or more modified nucleotides at the 5'-terminus of the passenger strand that prevents loading of the passenger strand into the RNA-induced silencing complex (RISC). In particular, the passenger strand may comprise at least two modified nucleotides at its 5'-terminus that prevents loading of the passenger strand into the RNA-induced silencing complex (RISC). Suitable modified nucleotides may include, but are not limited to 2'-O-methyl (2'OMe) nucleotides, 2'-deoxy-2'-fluoro (2'F) nucleotides, 2'-deoxy nucleotides, and 2'-O-(2-methoxyethyl) (MOE) nucleotides.

The disclosed polynucleotide sequences may include a 3' overhang of one or more nucleotides at the passenger strand, the guide strand, or both strands of the double-stranded polynucleotide. In some embodiments, the double-stranded polynucleotide comprises a 3' overhang of one or two deoxyribonucleotide residues (A, C, G, or T) in the passenger strand (optionally one or two thymidine residues) and/or the double-stranded polynucleotide comprises a 3' overhang of one or two deoxyribonucleotide residues (A, C, G, or T) in the guide strand (optionally one or two adenosine residues).

The identified polynucleotides that exhibit toxicity to cancer cells may be formulated as pharmaceutical compositions, for example, as pharmaceutical compositions for treating cell proliferative diseases and disorders such as cancer. The disclosed pharmaceutical compositions may be administered to a subject in need thereof, for example, a subject having a cell proliferative disease or disorder such as cancer.

ILLUSTRATIVE EMBODIMENTS

The following Embodiments are illustrative and should not be interpreted to limit the scope of the claimed subject matter.

Embodiment 1. A double-stranded polynucleotide comprising a passenger strand and a guide strand, the double-stranded polynucleotide optionally comprising: (i) a trinucleotide repeat sequence $(X_1X_2X_3)_n$, wherein $X_1$, $X_2$, and $X_3$ independently are selected from any ribonucleotide A, C, G, and U, and n is an integer from 3-10; and optionally where (ii) one or more modified nucleotides at the 5'-terminus of the passenger strand that prevents loading of the passenger strand into the RNA-induced silencing complex (RISC).

Embodiment 2. The double-stranded polynucleotide of embodiment 1, wherein the RNA is an siRNA or an shRNA.

Embodiment 3. The double-stranded polynucleotide of embodiment 1 or 2, wherein the trinucleotide repeat sequence has a GC content of at least 33%.

Embodiment 4. The double-stranded polynucleotide of any of the foregoing embodiments, wherein the trinucleotide repeat sequence has a GC content of at least 66%.

Embodiment 5. The double-stranded polynucleotide of any of the foregoing embodiments, wherein the trinucleotide repeat sequence is selected from the group consisting of $(ACC)_n$, $(ACG)_n$, $(AGC)_n$, $(AGG)_n$, $(CAC)_n$, $(CAG)_n$, $(CCA)_n$, $(CCC)_n$, $(CCG)_n$, $(CCU)_n$, $(CGA)_n$, $(CGC)_n$, $(CGG)_n$, $(CGU)_n$, $(CUC)_n$, $(CUG)_n$, $(GAC)_n$, $(GAG)_n$, $(GCA)_n$, $(GCC)_n$, $(GCG)_n$, $(GCU)_n$, $(GGA)_n$, $(GGC)_n$, $(GGG)_n$, $(GGU)_n$, $(GUC)_n$, $(GUG)_n$, $(UCC)_n$, $(UCG)_n$, $(UGC)_n$, and $(UGG)_n$, preferably wherein the trinucleotide is selected from the group consisting of $(AGC)_n$, $(CAG)_n$, $(CUG)_n$, $(GCA)_n$, $(GGU)_n$, and $(UGC)_n$, where n is an integer, typically selected from 3, 4, 5, 6, 7, 8, 9, 10, 11, 12, 13, 14, 15, to about 100 or higher.

Embodiment 6. The double-stranded polynucleotide of any of the foregoing embodiments, wherein the trinucleotide repeat sequence is CAG or CUG and the trinucleotide repeat sequence is present in the guide strand.

Embodiment 7. The double-stranded polynucleotide of any of the foregoing embodiments, wherein the passenger strand comprises at least two modified nucleotides at its 5'-terminus.

Embodiment 8. The double-stranded polynucleotide of any of the foregoing embodiments, wherein the one or more modified nucleotides at the 5'-terminus of the passenger strand are selected from the group consisting of 2'-O-methyl (2'OMe) nucleotides, 2'-deoxy-2'-fluoro (2'F) nucleotides, 2'-deoxy nucleotides, and 2'-O-(2-methoxyethyl) (MOE) nucleotides.

Embodiment 9. The double-stranded polynucleotide of any of the foregoing embodiments, wherein the double-stranded polynucleotide comprises a 3' overhang of one or more nucleotides at the passenger strand, the guide strand, or both strands of the double-stranded polynucleotide.

Embodiment 10. The double-stranded polynucleotide of any of the foregoing embodiments, comprising a 3' overhang of one or two deoxyribonucleotide residues (A, C, G, or T) in the passenger strand, optionally wherein the one or two deoxyribonucleotide residues are thymidine residues.

Embodiment 11. The double-stranded polynucleotide of any of the foregoing embodiments, comprising a 3' overhang of one or two deoxyribonucleotide residues (A, C, G, or T) in the guide strand, optionally wherein the one or two deoxyribonucleotide residues are adenosine residues.

Embodiment 12. An expression vector that expresses the polynucleotide of any of the foregoing embodiments or a single-stranded portion thereof.

Embodiment 13. The expression vector of embodiment 12 comprising a eukaryotic promoter operably linked to DNA encoding the polynucleotide or a single-stranded portion thereof.

Embodiment 14. The expression vector of embodiment 12 or 13, wherein the expression vector is a plasmid or a viral expression vector.

Embodiment 15. A pharmaceutical composition comprising: (i) the double-stranded polynucleotide of any of the foregoing embodiments or a single-stranded portion thereof, or a vector for expressing the double-stranded polynucleotide of any of the foregoing embodiments or a single-stranded portion thereof; and (ii) a pharmaceutically acceptable excipient.

Embodiment 16. A method for treating a disease or disorder in a subject in need thereof, the method comprising administering to the subject the pharmaceutical composition of embodiment 12.

Embodiment 17. The method of embodiment 13, wherein the disease or disorder is a cell proliferative disease or disorder such as cancer.

Embodiment 18. A method of inhibiting the growth of a cell or killing a cell, the method comprising introducing into the cell the double-stranded polynucleotide of any of embodiments 1-11 into the cell or a single-stranded portion thereof, or introducing a vector that expresses the double-stranded polynucleotide of any of embodiments 1-11 or a single-stranded portion thereof.

Embodiment 19. A nanoparticle comprising the polynucleotide of any of embodiments 1-11 or a single-stranded portion thereof.

Embodiment 20. The nanoparticle of embodiment 19, wherein the nanoparticle is a nanoparticle formed from lipoproteins and/or phospholipids (e.g., wherein the nanoparticle is a liposome or a micelle).

Embodiment 21. The nanoparticle of embodiment 19 or 20, wherein the polynucleotide is a siRNA and the siRNA is coupled to a lipoprotein of the nanoparticle.

Embodiment 22. An expression vector that expresses the polynucleotide of any of the foregoing embodiments or a single-stranded portion thereof.

Embodiment 23. The expression vector of embodiment 22 comprising a eukaryotic promoter operably linked to DNA encoding the polynucleotide or a single-stranded portion thereof.

Embodiment 24. The expression vector of embodiment 22 or 23, wherein the expression vector is a plasmid or a viral expression vector.

EXAMPLES

The following Examples are illustrative and are illustrative and should not be interpreted to limit the scope of the claimed subject matter.

Title—Small Interfering RNAs Based on Huntingtin Trinucleotide Repeats are Highly Toxic to Cancer Cells Reference is made to Murmann et al. "Small interfering RNAs based on huntingtin trinucleotide repeats are highly toxic to cancer cells," (2018), the content of which is incorporate herein by reference in its entirety.

Abstract

Trinucleotide repeat (TNR) expansions in the genome cause a number of degenerative diseases. A prominent TNR expansion involves the trinucleotide repeat CAG in the huntingtin (HTT) gene responsible for Huntington's disease (HD). Pathology is caused by protein and RNA generated from the TNR regions including small siRNA-sized repeat fragments. An inverse correlation between the length of the repeats in HTT and cancer incidence has been reported for HD patients. We now show that siRNAs based on the CAG TNR are toxic to cancer cells by targeting genes that contain long reverse complimentary TNRs in their open reading frames. Of the 60 siRNAs based on the different TNRs, the 6 members in the CAG/CUG family of related TNRs are the most toxic to both human and mouse cancer cells. siCAG/CUG TNR-based siRNAs induce cell death in vitro in all tested cancer cell lines and slow down tumor growth in a preclinical mouse model of ovarian cancer with no signs of toxicity to the mice. We propose to explore TNR-based siRNAs as a novel form of anti-cancer reagents.

Introduction

Trinucleotide repeat (TNR) expansions are the cause of a large number of degenerative disease syndromes characterized by amplification of DNA triplet motifs [1]. They include spinocerebellar ataxias (SCAs), spinobulbar muscular atrophy (SBMA), myotonic dystrophy type 1 (DM1), and Huntington's disease (HD) [1, 2]. HD is a dominantly inherited neurodegenerative disorder caused by expansion of CAG repeats in the huntingtin (HTT) gene. It has been shown that the resulting glutamine expansions (polyQ) in HTT are toxic to cells [3, 4] and that the length of the CAG amplifications determines severity and onset of the disease [2, 4]. In addition to polyQ toxicity, repeat-associated, non-ATG translation (RAN translation) was discovered as another translation-level pathogenic mechanism of CAG repeat-containing mRNAs [5]. More recent evidence however, also points toward RNA playing a role in affecting cell viability by poly-triplet repeats [1, 6]. Indeed, many of the repeats in several TNR diseases are not located in open reading frames (ORFs) but in introns or untranslated regions (UTRs) [4]. DM1 is the best-characterized disease regarding RNA toxicity. The CUG repeats are in the 3'UTR of the dystrophia myotonica protein kinase (DMPK) gene, causing most of their toxicity by forming hairpin structures [7]. These hairpins are believed to recruit a number of RNA-binding proteins to nuclear RNA foci [8]. Another mechanism by which CAG/CUG TNRs could be toxic at the RNA level is by interfering with cellular splicing. This has been shown for CUG in DM1 [9] and CAG in HD [10].

Mounting evidence suggests the CAG TNR expansions are toxic at the RNA level. It was shown in *Drosophila* that the toxicity of the CAG repeat disease gene spinocerebellar ataxia type 3 (SCA3) protein ataxin-3, is in large part caused by the trinucleotide repeat RNA and not the polyQ protein [11]. Replacing some of the glutamine coding CAG repeats with the other codon coding for glutamine, CAA, mitigated the toxicity despite similar polyQ protein expression levels. Direct toxicity of mRNA with extended CAG repeats was also demonstrated in mice [12]. Finally, there is convincing evidence that CAG/CUG repeats can give rise to RNAi-active small RNAs. In human neuronal cells, expression of the CAG expanded exon 1 of HTT (above the threshold for complete penetrance which is >40) [6] caused an increase in small CAG repeat-derived RNAs (sCAG) of about 21 nt in length. Above a certain length, CAG/CUG repeats were found to be cleaved by Dicer, the enzyme that generates mature miRNAs from pre-miRNAs before they are incorporated into the RNA induced silencing complex (RISC) [13]. The CAG repeat derived fragments could bind to complementary transcripts and downregulate their expression via an RNAi-based mechanism. In a mouse model of HD treatment of the mice with a locked nucleic acid-modified 20 mer antisense oligonucleotide complementary to the CAG TNR (LNA-CTG) which reduced the expression of sCAGs but not of HTT mRNA or protein reversed motor deficits [14]. This study identified sCAG as a disease causing agent. Since sCAGs, isolated from HD human brains, when transfected reduced viability of neurons [6], these sequences might affect cell viability through RNAi by targeting genes that regulate cell survival.

We recently reported that siRNAs and shRNAs derived from CD95, CD95L [15], and other genes in the human genome [16] kill cancer cells through RNAi by targeting a network of critical survival genes [15]. DISE (death induced by survival gene elimination) was found to involve simultaneous activation of multiple cell death pathways, and cancer cells have a hard time developing resistance to this form of cell death [17]. DISE was found to preferentially affect transformed cells [17]. Because the length of the CAG repeats in different CAG repeat diseases has been inversely correlated with cancer incidence in various organs [18-21], we were wondering whether RNAi active CAG based TNRs might be responsible for this phenomenon and whether they could be used to kill cancer cells.

We have now identified an entire family of TNR-based siRNAs—which contains the CAG repeat that causes HD—to be at least 10 times more toxic to cancer cells than any tested DISE-inducing si/shRNA. Our data suggest this super toxicity is caused by targeting multiple complementary TNR expansions present in the open reading frames (ORFs) of multiple genes, rather than in their 3'UTRs. As a proof of concept, we demonstrate that siCAG/CUG can be safely administered to mice to slow down growth of xenografted ovarian cancer cells with no obvious toxicity to the animals. We are proposing to develop super toxic TNR expansion-based siRNAs for cancer treatment.

Figure 1B:
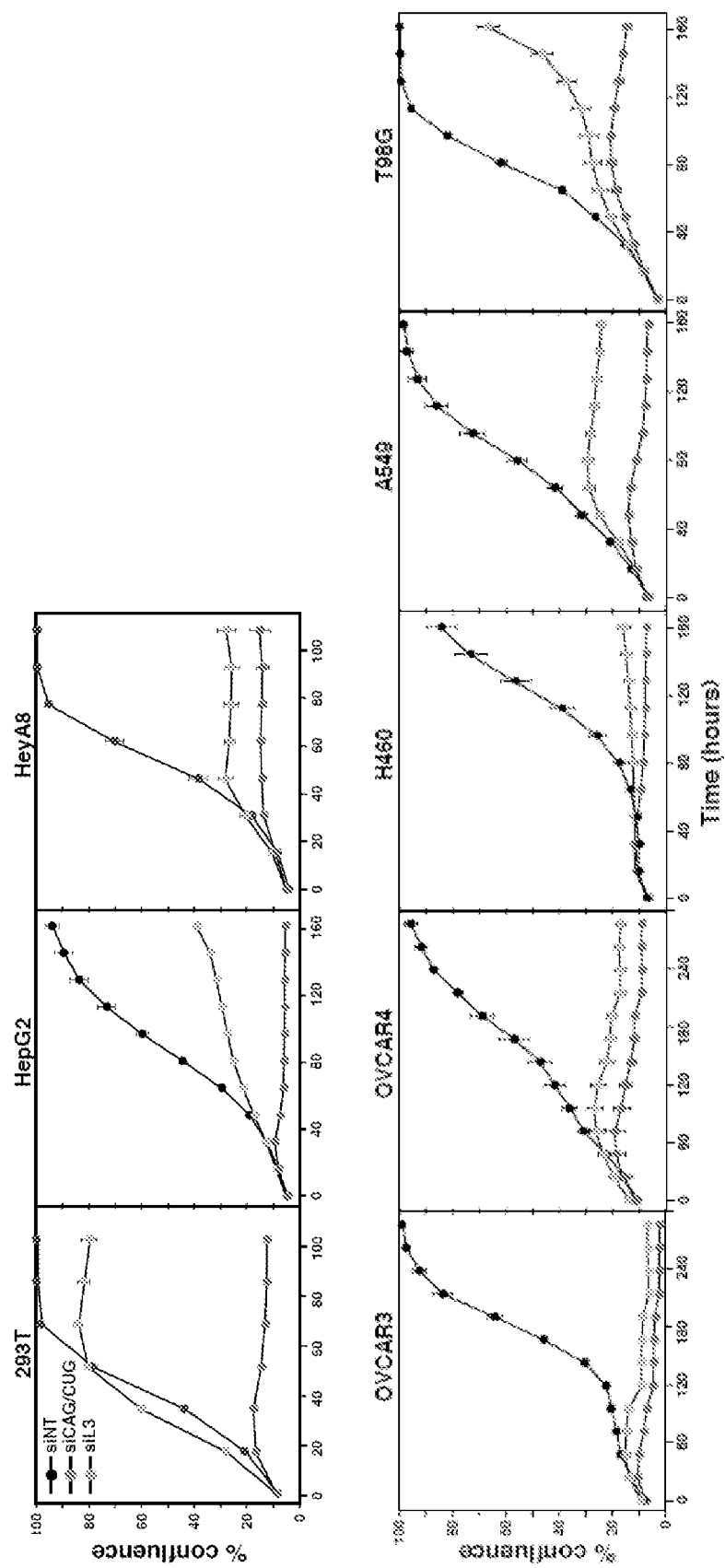
Figure 1C:
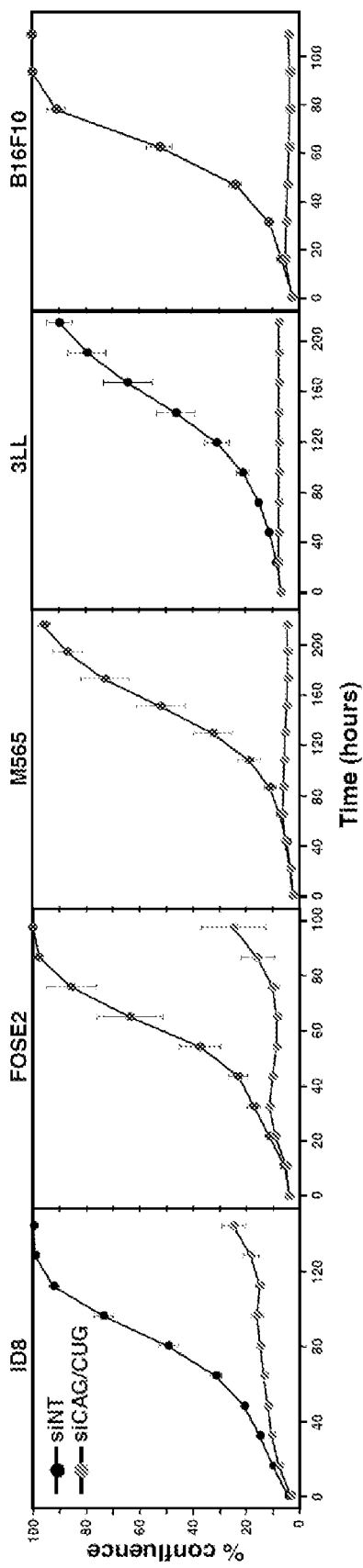
Figure 1E:
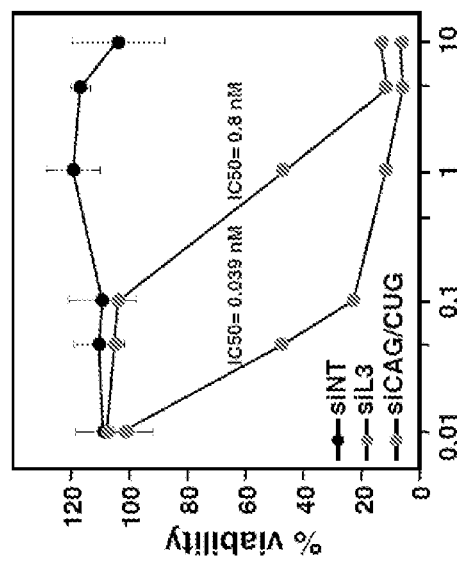
Figure 1D:
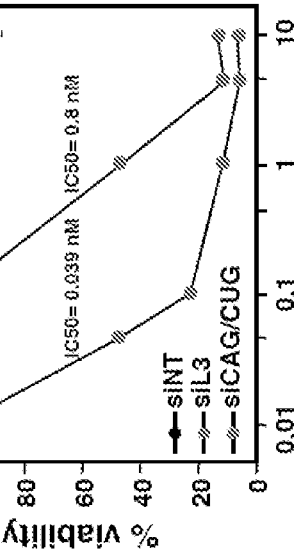
Figure 6A:
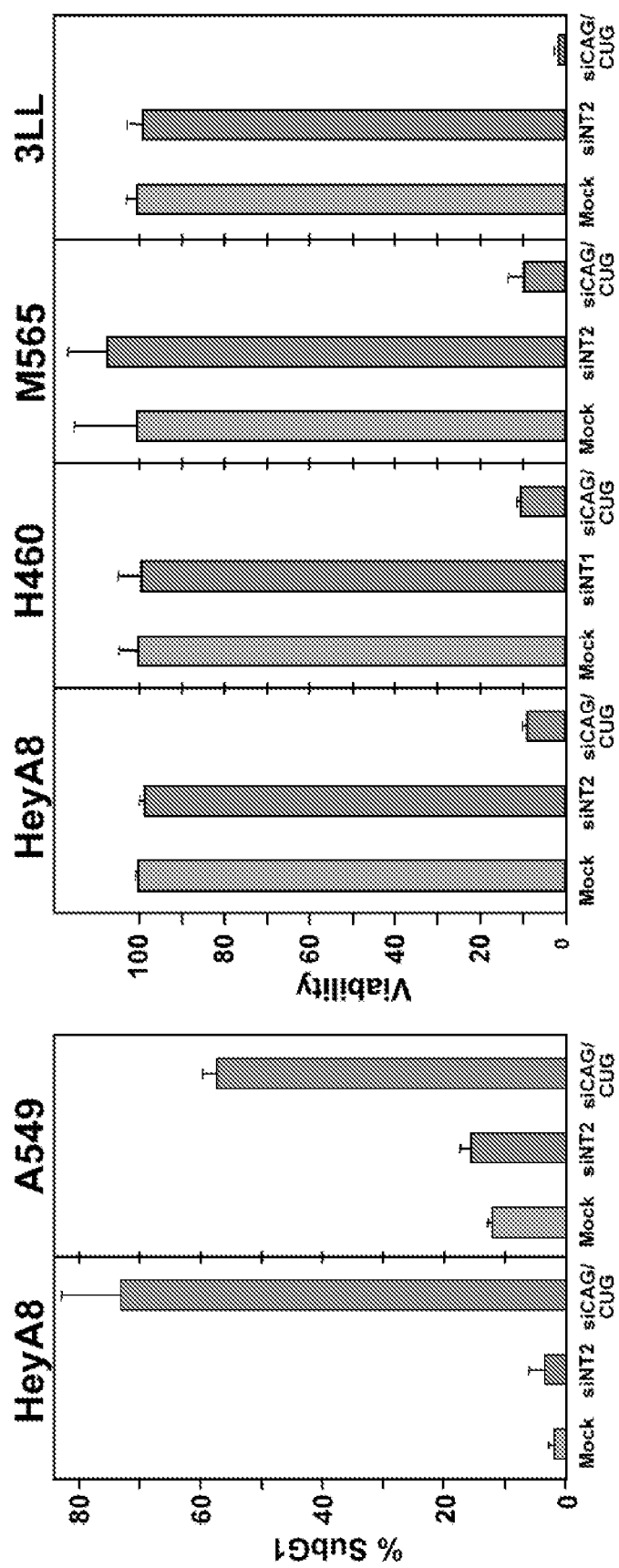
FIGS. 6A and 6B. Morphological changes and cell death in cells transfected with siCAG/CUG.
Figure 6B:
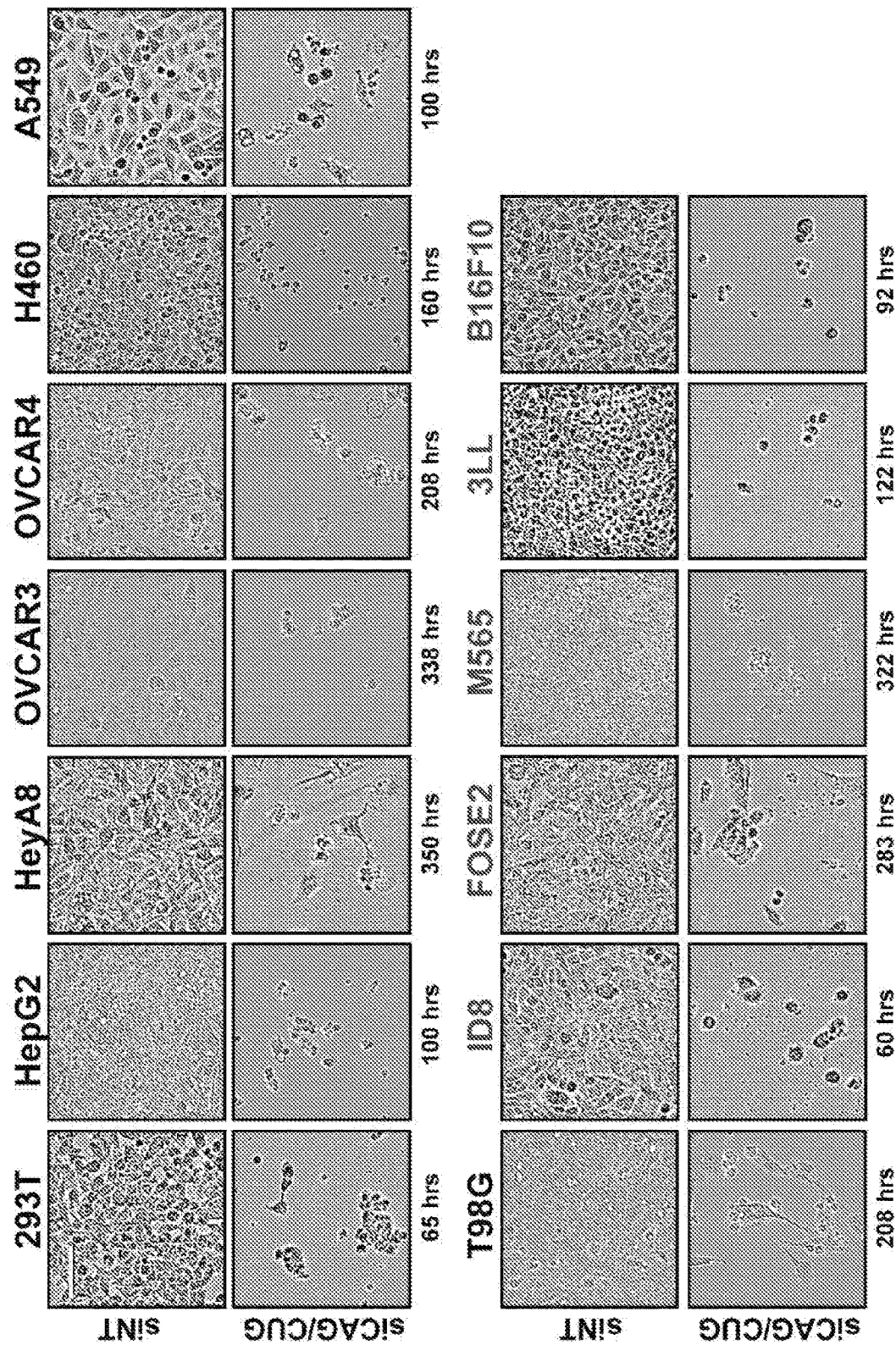

Results siCAG/CUG kills all cancer cells in vitro. CAG repeats are the defining factor in Huntington's disease, and their complement CTG is amplified in myotonic dystrophy type 1 (DM1) [1]. We were interested in determining whether a 19 mer duplex of CAG and CUG repeats (siCAG/CUG) (FIG. 1A) would affect the growth of cancer cells. When transfecting siCAG/CUG into various human (FIG. 1B) and mouse (FIG. 1C) cancer cell lines at 10 nM, all cancer cells stopped growing within hours of transfection and eventually most of the cells died with no outgrowth of recovering cells (FIG. 6A). All cancer cells transfected with siCAG/CUG showed morphological changes similar to the ones we observed in cells undergoing DISE (FIG. 6B, [15, 17]). We found that siCAG/CUG killed HCT116 cells even when transfected at 10 pM (FIG. 1D). Compared to any other si- or shRNA we have tested siCAG/CUG is ~10-100 times more toxic depending on the assay used. When monitoring cell viability (ATP content), the IC50 for siL3, the most toxic DISE inducing siRNA we have used, was determined to be 0.8 nM and for siCAG/CUG was 0.039 nM (FIG. 1E).

Figure 2A:
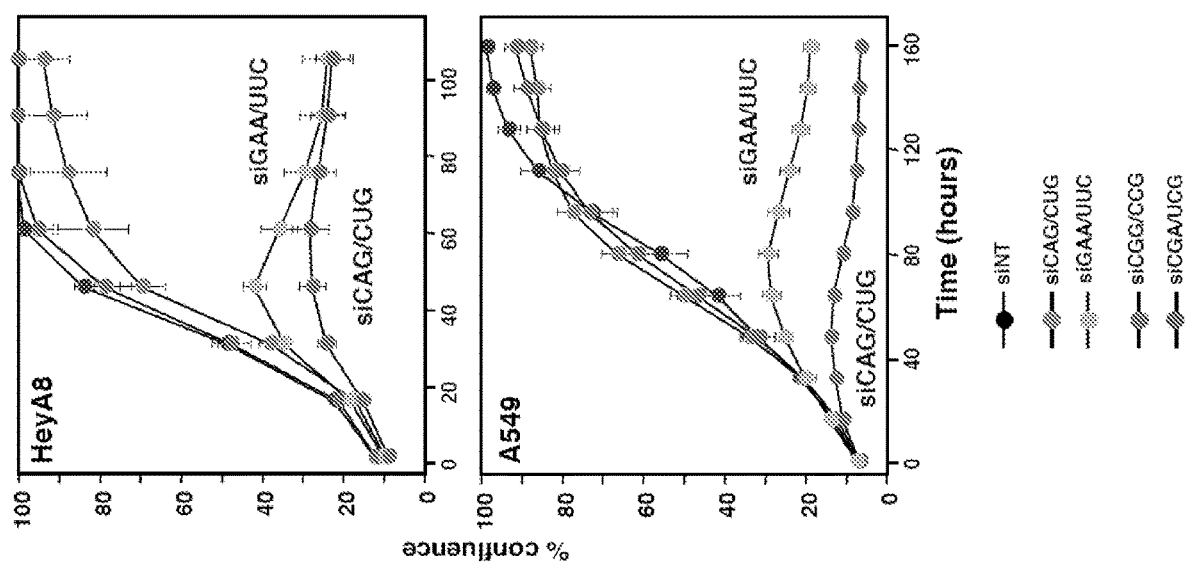
FIGS. 2A-E. Identification of the most toxic TNR-based siRNAs.
Figure 7:
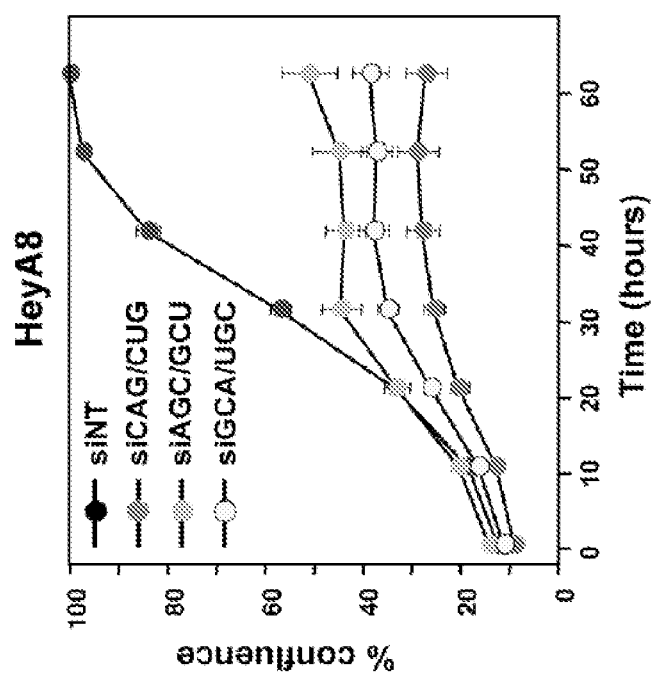
FIG. 7. Properties of toxic TNR based siRNAs. Left: Sequences of the siCAG repeat in three different frames. Right: Confluence over time of HeyA8 cells transfected with 1 nM of either siNT or the three duplexes depicted on the left. Values are mean−/+SEM. n=3 biological replicates, 4-8 technical replicates each.
Figure 7:
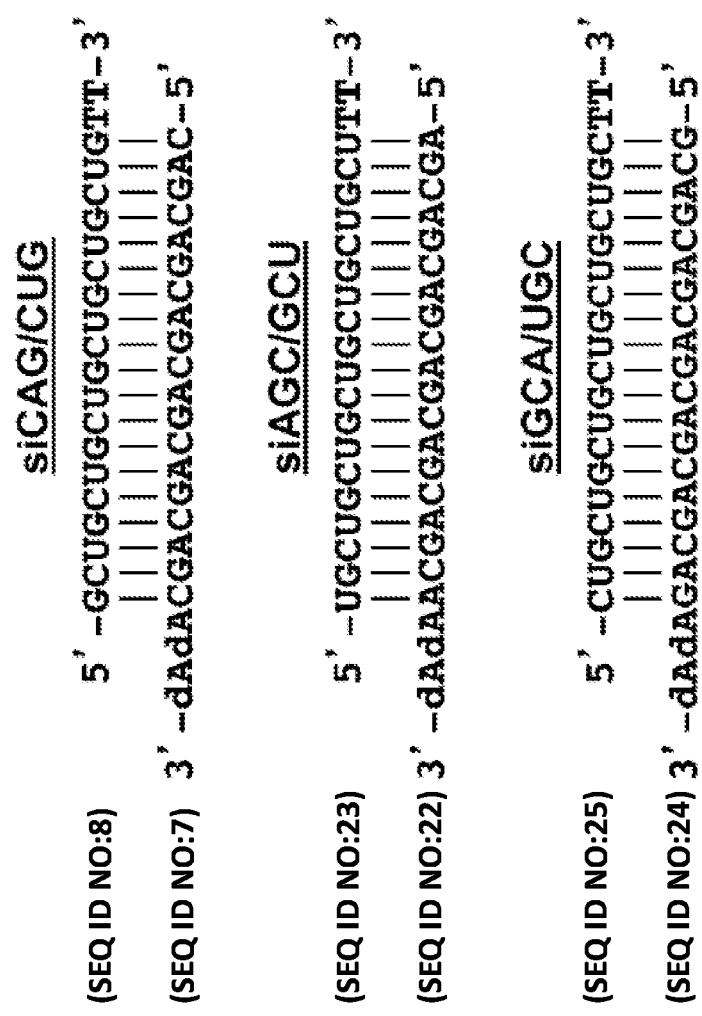

Identification of the most toxic TNR based siRNAs. The siCAG/CUG repeat 19 mer in all three frames showed roughly the same level of toxicity when transfected into HeyA8 cells (FIG. 7). To test whether other TNR disease-derived sequences were toxic to cancer cells when introduced as siRNAs, the repeats siGAA/UUC (GAA is amplified in Friedreich's ataxia [22]), siCGG/CCG (CGG found in fragile X tremor ataxia syndrome [FXTAS] and CCG found in Fragile XE mental retardation [FRAXE] [1]) were transfected into HeyA8 (ovarian) and A549 (lung) cancer cells (FIG. 2A). In addition, siCGA/UCG was tested because it has the same base composition as the super toxic siCAG/CUG TNR. Interestingly, among the four tested TNR siRNA duplexes two were super toxic to both cell lines, and two showed no toxicity. Most remarkable was the observation that siCGA/UCG was among the nontoxic repeats. This finding pointed at a sequence specific mechanism behind this phenomenon rather than a response of the cells to dsRNA of a specific base composition.

Figure 8:
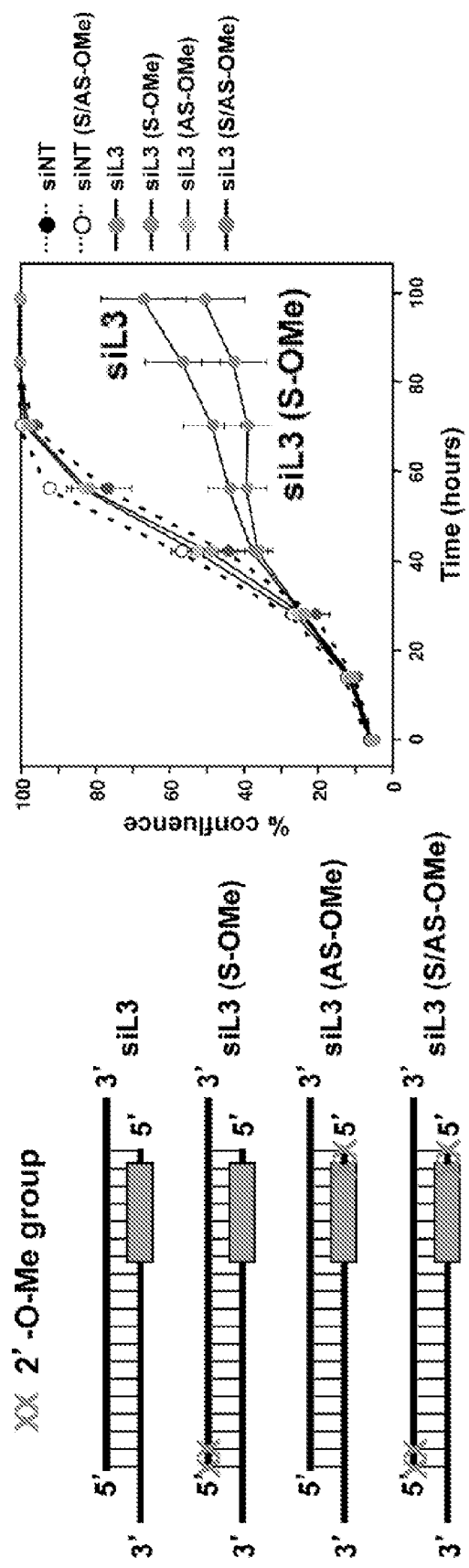
FIG. 8. The toxicity of siL3 is solely based on its guide strand. Left: Scheme showing positions of the 2'O-methylation in either the passenger/sense (S) or the guide/antisense (AS) strand of siL3. The siL3 seed region is shown as a green box. Right: Confluence over time of HeyA8 cells transfected with 10 nM of the four duplexes depicted on the left and two similarly modified duplexes derived from siNT. Values are mean−/+SEM. n=3 technical replicates.

To identify the most toxic TNR sequences in an unbiased screen, we designed a library of 19 mer siRNAs based on the 60 possible TNRs (that contain more than one type of nucleotide). To reduce passenger strand loading and determine the toxicity of each repeat when loaded into the RISC as a guide strand, we replaced positions 1 and 2 of the passenger strand with 2'-O-methylated (OMe) nucleotides. To confirm the effect of the OMe modification, we modified the toxic CD95L-derived siRNA siL3 in this way. While the siL3 duplex modified on the intended passenger strand (S-OMe) was slightly more toxic to cells than unmodified siL3, likely reflecting a low level of passenger strand loading of siL3, neither siL3 modified on the antisense strand (AS-OMe) nor on both strands (S/AS-OMe) showed any toxicity (FIG. 8).

Figure 2B:
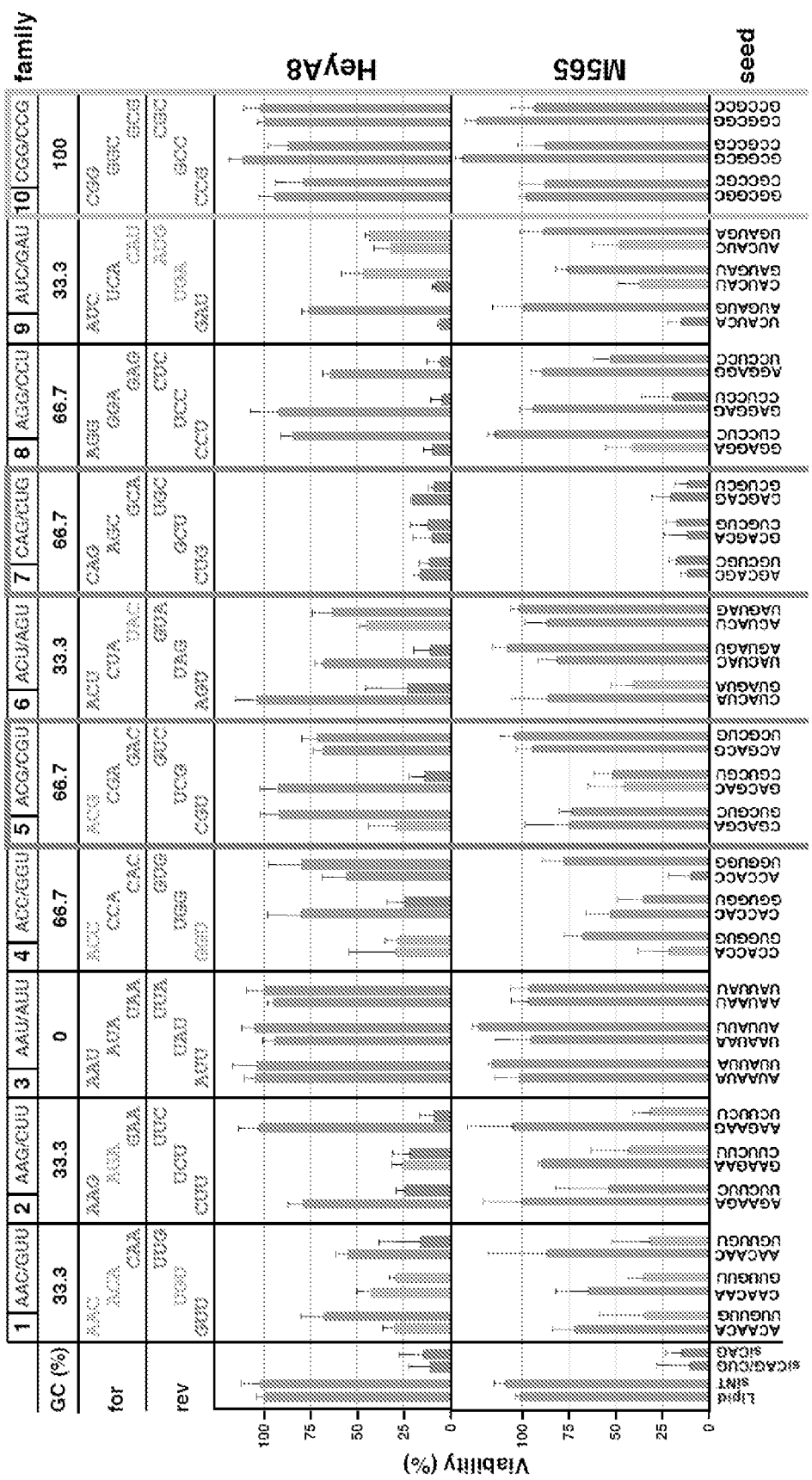

All 60 TNRs were now synthesized with the sense strand carrying the OMe modification in positions 1 and 2, allowing us to determine the toxicity of each of the 60 antisense sequences. HeyA8 cells were transfected with 1 nM of each of the 60 TNRs and viability was quantified 96 hrs after transfection. The 60 TNRs can be grouped into 10 families [23]. Each family is comprised of 3 triplets shifted by one nucleotide plus its three complementary triplets. In total 30 (50%) of the TNRs were not toxic, 11 (18%) were moderately toxic (>50% loss of viability, shown in yellow), and 19 (31.7%) were super toxic (>75% loss of viability, shown in red) to HeyA8 cells (FIG. 2B, top panels). Among the nontoxic TNRs were all 6 members of family 3 (0% GC content) and all 6 members of family 10 (100% GC content). All other TNR families contained nontoxic and toxic TNRs. Interestingly, in some cases just shifting the TNR sequence in the 19 mer by one nucleotide resulted in opposite effects on viability (i.e. AGG and GGA in family 8). In other cases, members of a family showed toxicity of one strand but no toxicity of its complement (i.e. families 1, 2, 4, 5, 6, 8 and 9). This finding suggests a sequence-specific and in some cases frame specific activity of the TNRs consistent with RNAi being involved. Due to the different base composition of targeted RNAs, the comparison of TNR families with the same GC content and base composition is most meaningful. Two families contain a balanced GC content of 66.7% and identical base composition: family 5 and 7. Remarkably, while family 5 contained toxic and nontoxic members, all six TNRs in family 7 were super toxic (boxed in red in FIG. 2B). Family 7 stands out as it contains all permutations of both the CAG and the CUG repeats we identified as killing all cancer cells.

Figure 2C:
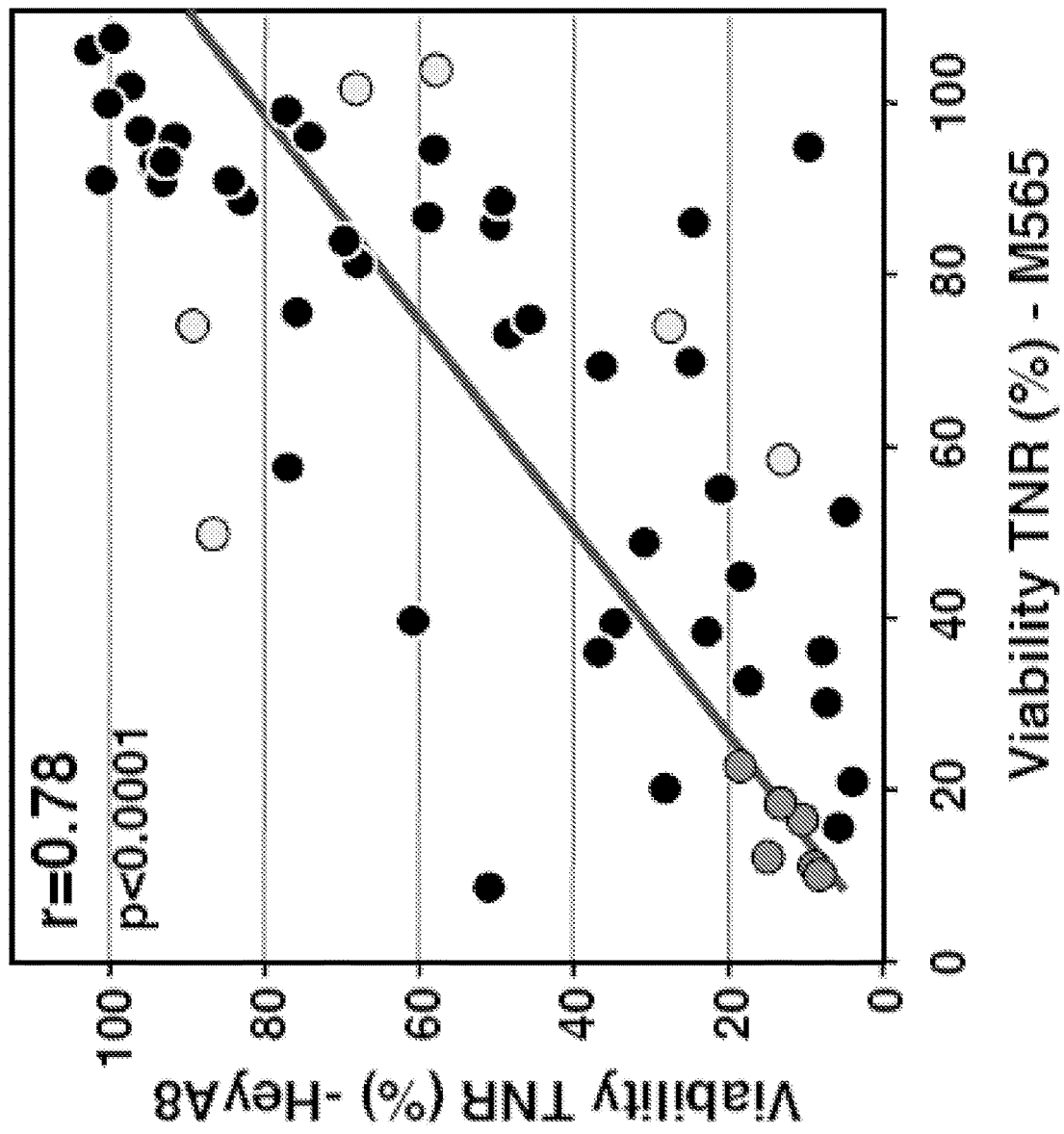
Figure 9:
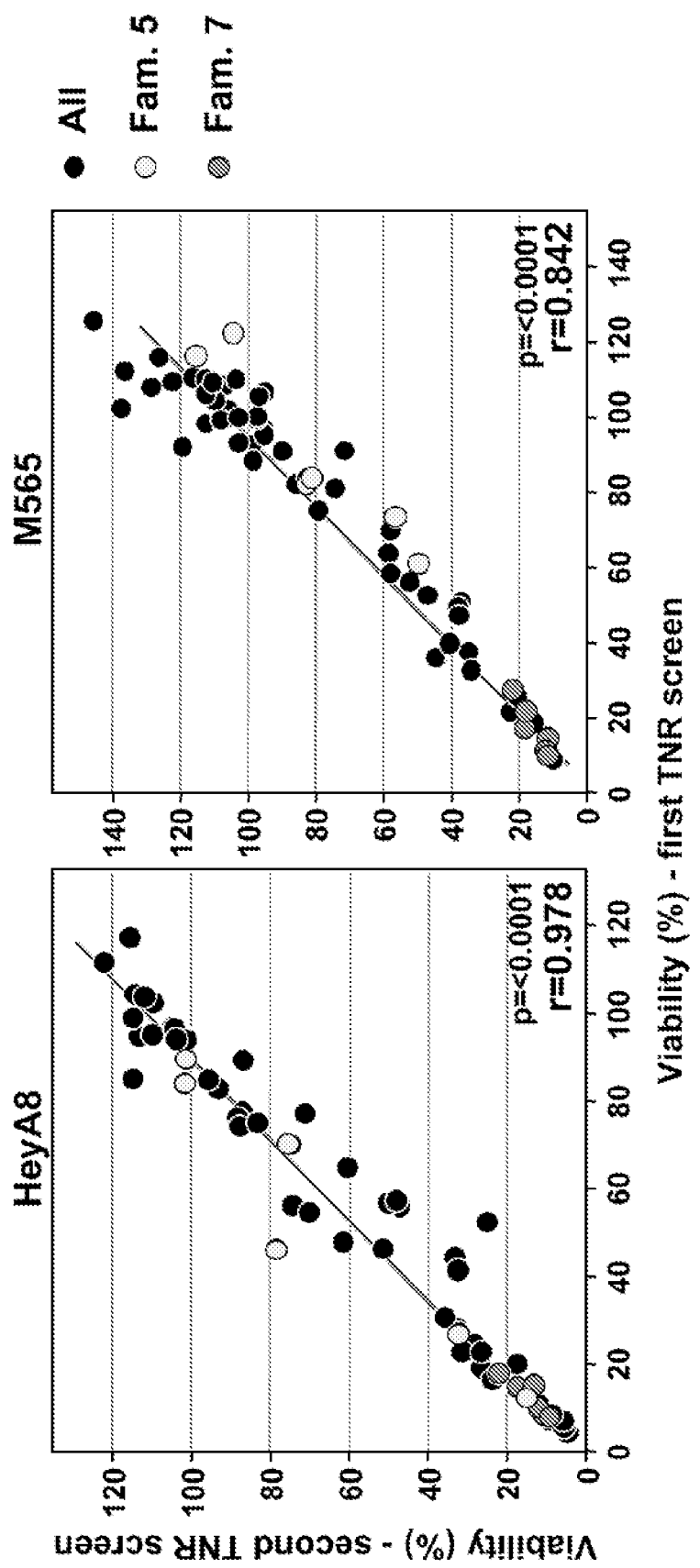
FIG. 9. Reproducibility of the TNR siRNA screens. Variation between the two screens of the 60 TNR based siRNAs in HeyA8 (left) and in M565 (right) cells. The data points for the six members of TNR family 5 are labeled in blue those of family 7 are labeled in red. Pearson correlations and p-values are given.

To determine how much of these activities were conserved between human and mouse cancer cells, the screen was repeated with the mouse liver cancer cell line M565 (FIG. 2B, bottom panels). The results for the siRNAs in TNR families 1, 2, 4, 5, 8, and 9 were somewhat similar to the ones obtained with the human cell line, but also showed clear differences. This could be due to differences in tissue origin, cell line, or species between the two cell lines. Three of the TNR families performed in an identical fashion between the two cell lines. Similar to HeyA8 cells, none of the 12 TNR-derived siRNAs in families 3 or 10 showed any toxicity in M565 cells. Most strikingly however, was the finding that again all 6 members of family 7, which contain both the CAG and the CUG repeat, were super toxic to the mouse cell line. Screens in both HeyA8 and M565 cells were repeated and results showed a high degree of congruence, especially in the results of family 7 (FIG. 9). When the average of the screen in HeyA8 cells was plotted against the averages of the two screens in M565 cells, a significant correlation between the screens was found (FIG. 2C) and again the six TNRs in family 7 were most consistently toxic. The data suggests the toxicity of this TNR family is conserved and it is independent of tissue, cell line and species.

Figure 2D:
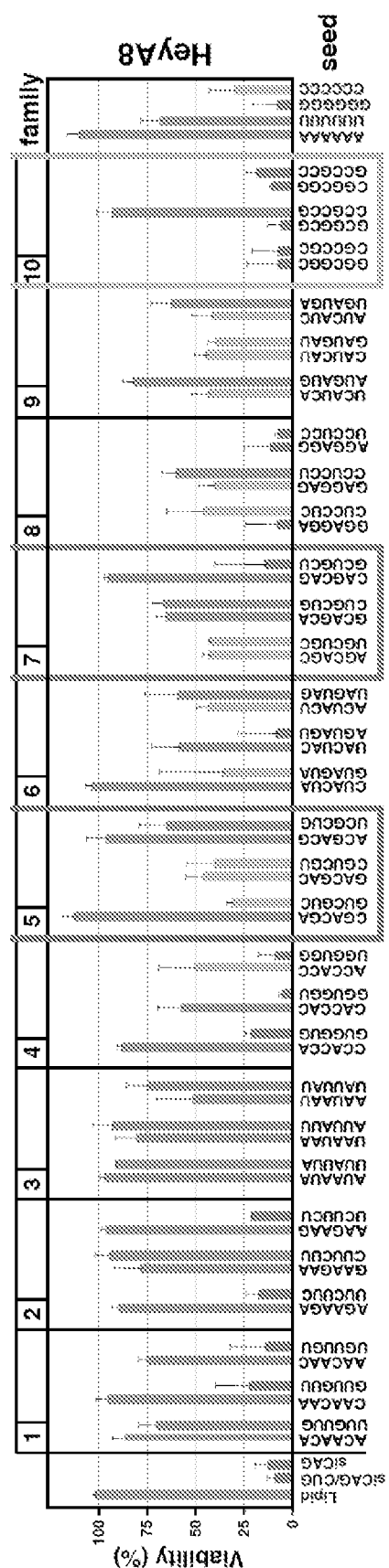
Figure 2E:
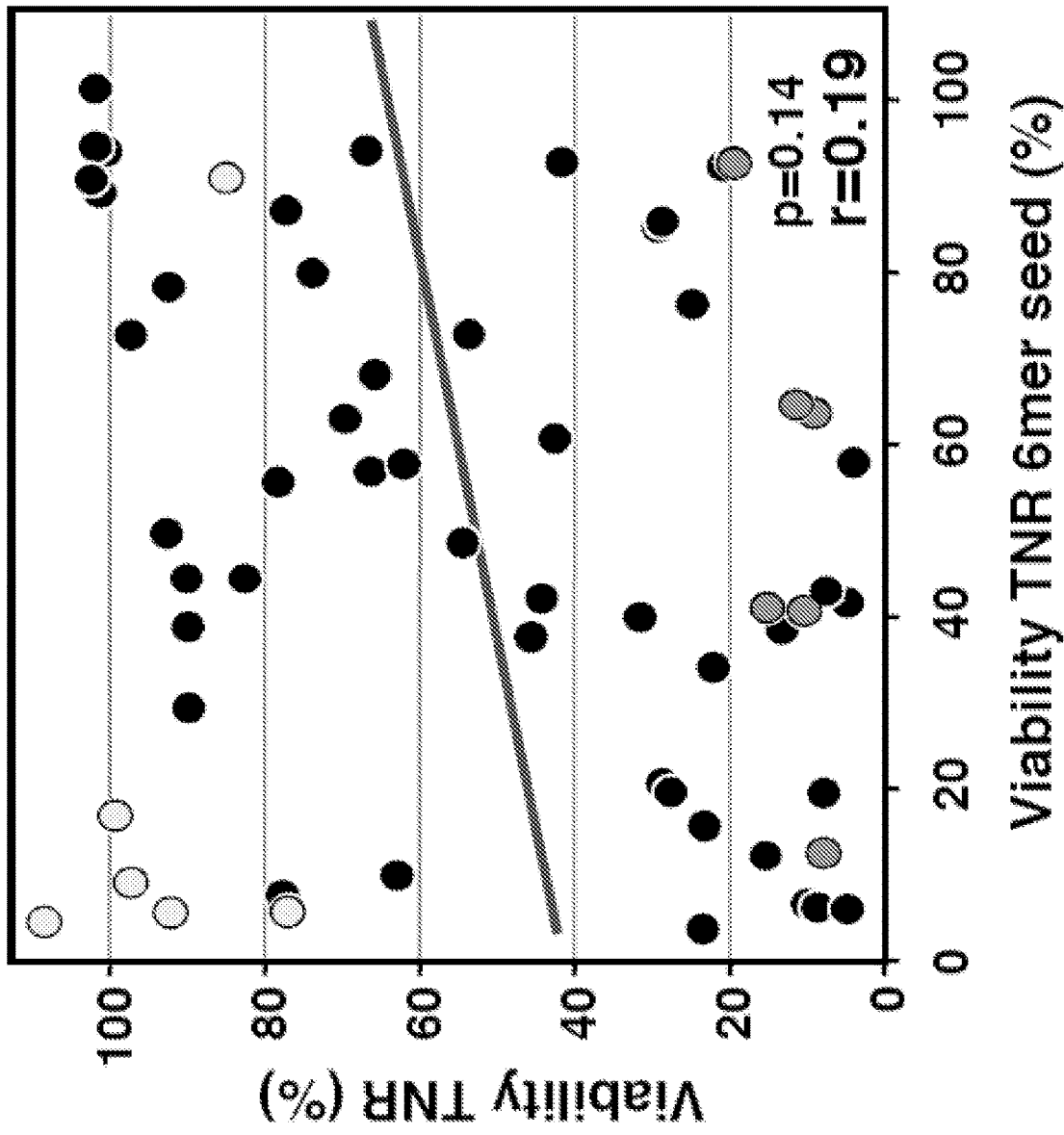
Figures 10A, 10B:
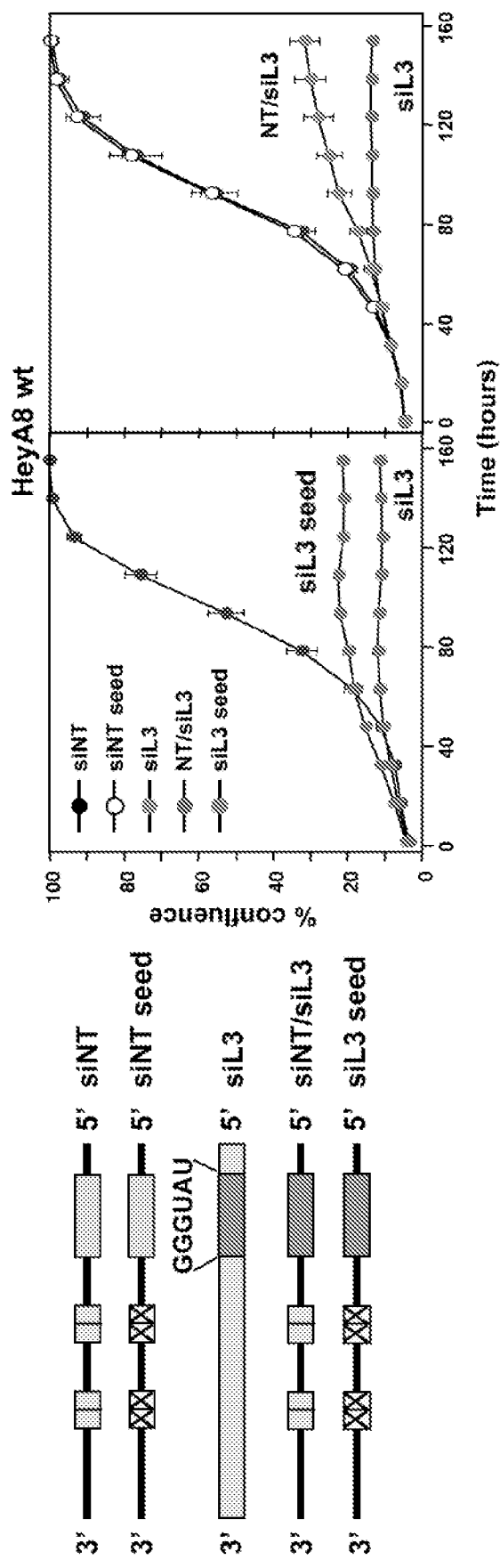
FIGS. 10A and 10B. DISE inducing activity of siL3 is mostly based on its seed sequence.

We recently reported that the 6 mer seed sequence of siL3 was the main determinant of its toxicity [15]. We therefore wondered how much of the toxicity of the super toxic TNRs was due to complete complementarity of the siRNA and how much was dependent on just the 6 mer seed sequence. The data on siL3 were obtained by generating chimeric siRNA duplexes between a nontoxic control siRNA (siNT) and siL3 by replacing siL3 sequences from either end of the duplex with siNT sequences [15]. To generate an artificial nontoxic siRNA backbone in which to test all 60 TNR 6 mer seed sequences, we first replaced 4 positions in the center of siNT still identical to the same position in the siL3 sequence with the complementary nucleotides, thereby removing any identity between siNT and siL3 outside the seed, while maintaining GC content (FIG. 10A). This siL3 seed siRNA (siL3 seed) was almost as toxic to HeyA8 cells as siL3, confirming that the 6 mer seed determined a substantial part of the toxicity of siL3. We therefore used the modified siNT backbone to test all possible TNR-derived 6 mer seed sequences (FIG. 2D, FIG. 10B). While some TNR derived seeds were toxic to HeyA8 cells, there was only a moderate level of congruence between the screen with the entire TNR 19 mers and one just with the 6 mers in the modified siNT backbone (FIG. 2E). Of the 6 super toxic TNRs in family 7 only one was also toxic in the 6 mer screen (FIGS. 2D and 2E). Interestingly, most of the 6 mers in family 10 were toxic although no toxicity was observed in the TNR screen (FIG. 2B). We interpret this as the inability of these 6 TNRs with their 100% GC content to properly enter the RISC. Together these data suggest 19 mer TNR siRNAs are toxic to cancer cells by a mechanism distinct from the process of DISE which relies on just the seed sequences targeting the 3'UTRs of survival genes [15].

Figure 3A:
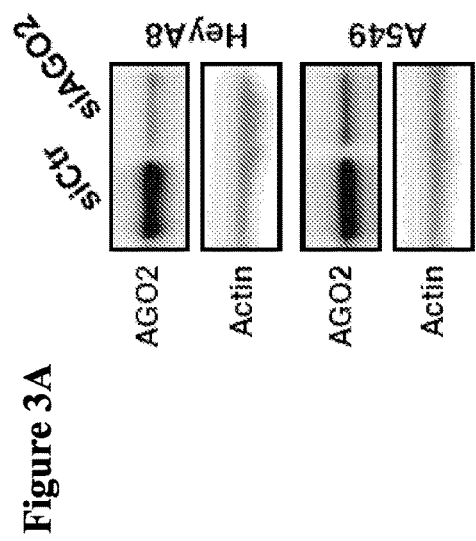
FIGS. 3A-E. siCAG/CUG kills cancer cells through RNAi.
Figure 3B:
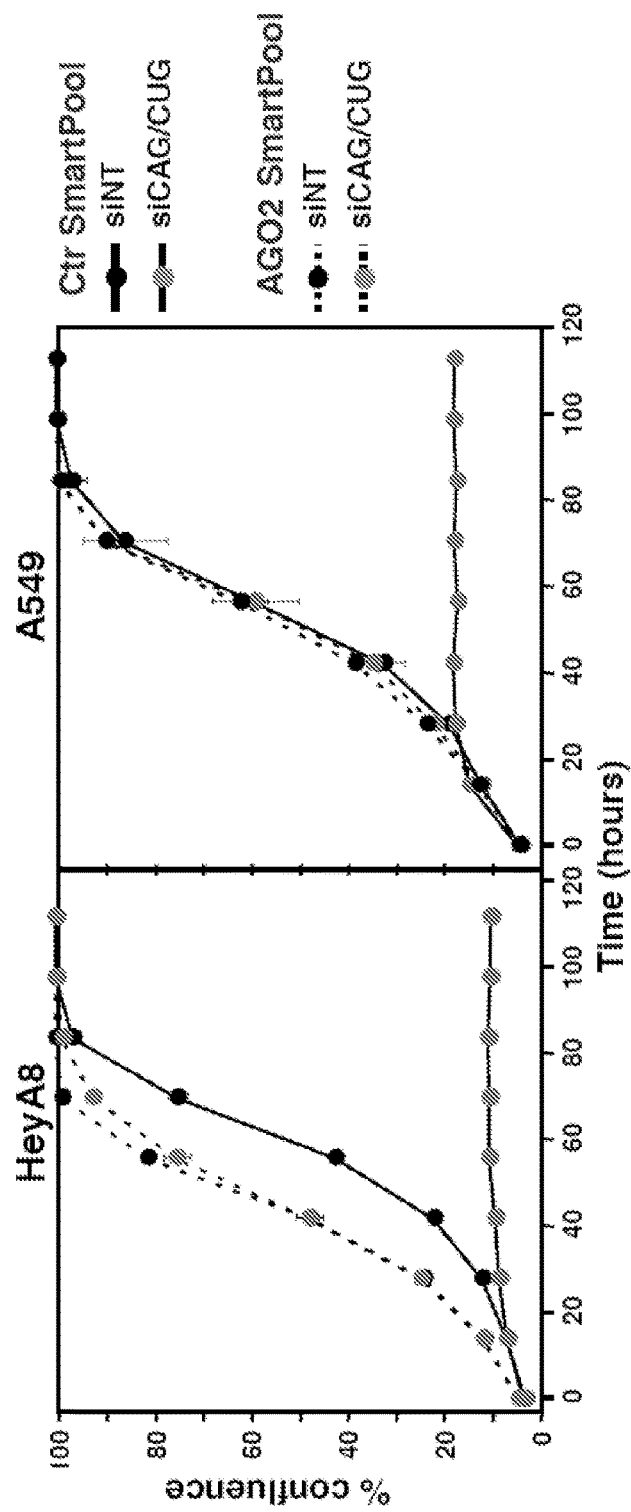
Figure 3C:
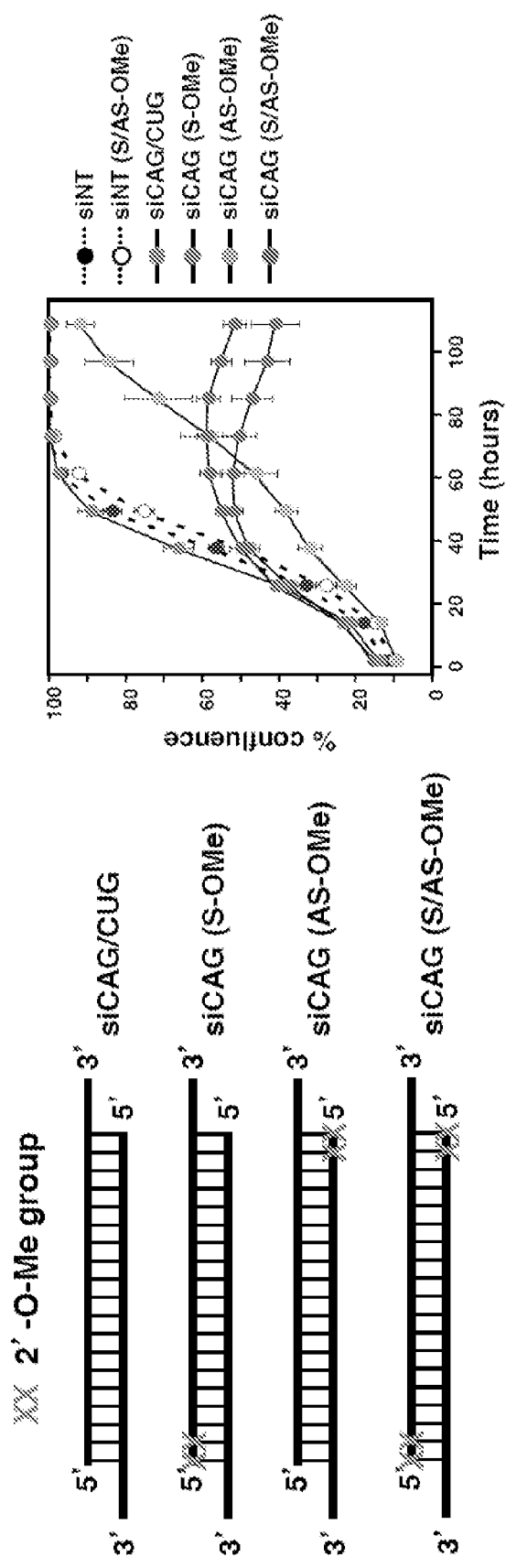
Figure 11:
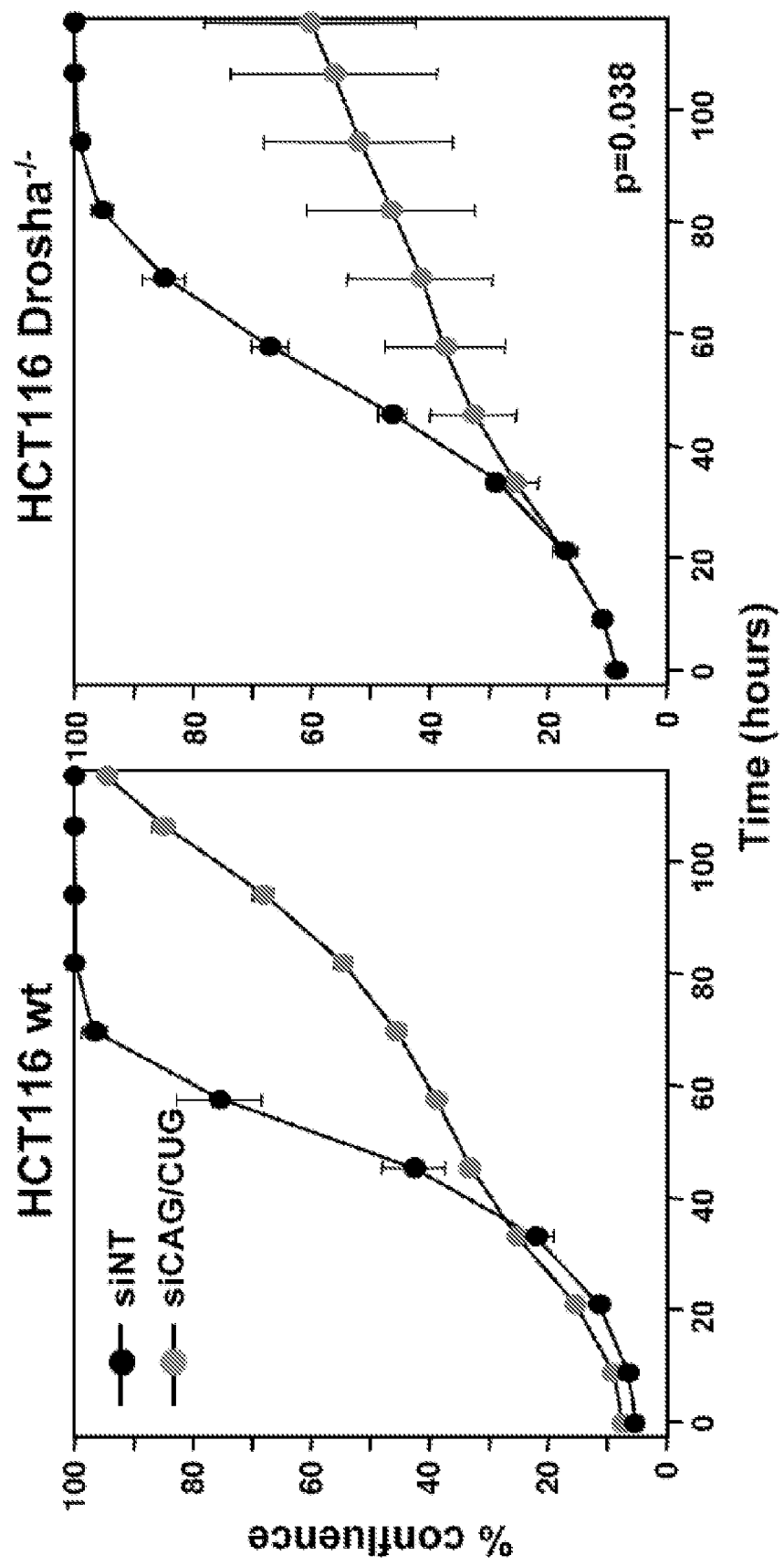
FIG. 11. Increased sensitivity of HCT116 Drosha$^{-/-}$ cells compared to HCT116 wild-type cells. Confluency over time of either HCT116 wt (left) or Drosha$^{-/-}$ (right) cells transfected with 0.1 nM of either siNT or siCAG/CUG. Transfection efficiency of the two cell lines was similar as assessed by uptake of siGLO [1]. p-value according to polynomial distribution is given. Values are mean−/+SEM. n=3 biological replicates, 3-4 technical replicates each.
Figure 12A:
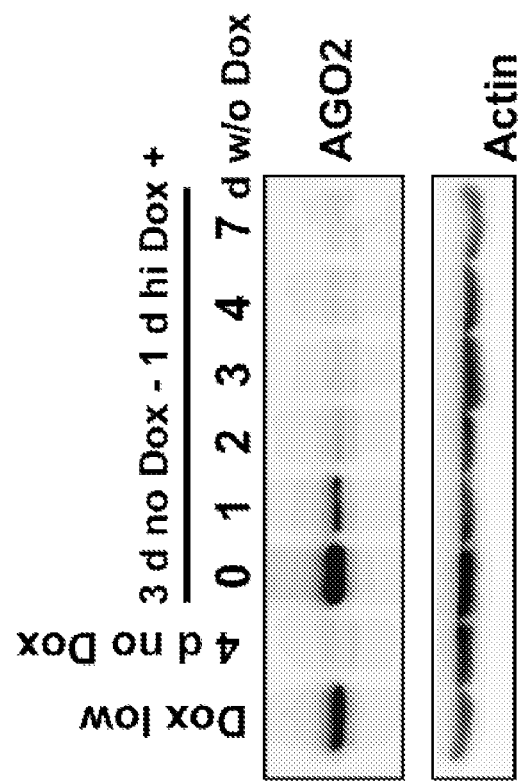
FIGS. 12A and 12B. siCAG/CUG induced growth reduction of mouse embryonic stem cells requires Ago2.
Figure 12B:
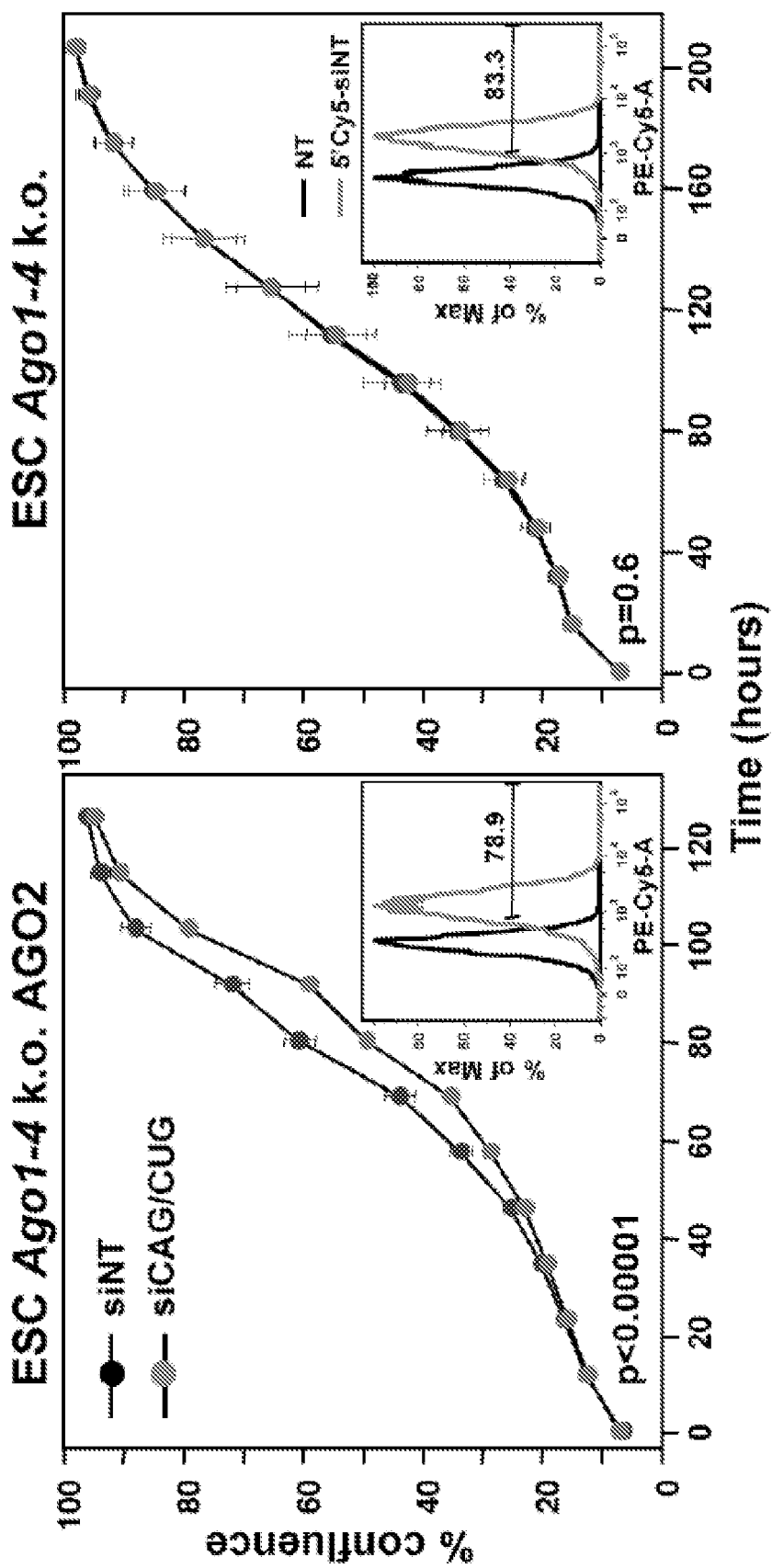

Super toxic TNR-based siRNAs kill cancer cells through RNAi resulting in the loss of survival genes. To address the question whether the super toxic TNR-based siRNAs killed cancer cells through RNAi, we first compared the toxicity of siCAG/CUG in HCT116 wild-type and HCT116 Drosha$^{-/-}$ cells. DISE inducing si- and shRNAs kill Drosha$^{-/-}$ cells more efficiently than wild-type cells [15]. We had interpreted this as the RISC being more available in the absence of most cellular miRNAs, which rely on Drosha for processing. While siCAG/CUG was highly toxic to both cell lines at early time points, Drosha$^{-/-}$ cells were more sensitive to growth reduction induced by siCAG than their wild-type counterparts (FIG. 11, p=0.038, according to polynomial fitting model). To directly test the requirement of AGO2 in the siCAG/CUG induced toxicity we knocked down AGO2 in both HeyA8 and A549 cells (FIG. 3A) and transfected the cells with either siNT or siCAG/CUG (FIG. 3B). Removal of AGO2 from the cells almost completely prevented the toxicity of siCAG/CUG confirming dependence on the RISC. A dependence on Ago2 for siCAG/CUG toxicity was confirmed in Ago1-4 knock-out mouse embryonic fibroblasts with re-expressed AGO2 (FIG. 12). These data indicated that siCAG/CUG was negatively affecting cells through canonical RNAi involving the RISC complex. To confirm this, we modified the siCAG siRNAs with the 2'-O-methylation to selectively block loading of either the siCAG or the siCUG based strand into the RISC (FIG. 3C). When the CAG-based guide strand was modified (siCAG AS-OMe), the toxicity of the siCAG/CUG duplex was severely reduced. It was not affected when the CUG repeat containing strand was 2'-O-methylated (siCAG 5-OMe), confirming that most of the toxicity of the siCAG/CUG repeat comes from the CAG repeat strand. siCAG/CUG did not have any toxicity when both strands were modified indicating most, if not all, of its toxicity requires RISC loading confirming that RNAi was responsible for cell death.

We recently reported that DISE-inducing CD95L derived sh- and siRNAs kill cancer cells by targeting the 3'UTR of critical survival genes through canonical RNAi [15]. To test whether the super toxic siCAG/CUG duplex also killed cancer cells through this mechanism, we transfected HeyA8 cells with siNT, siCAG/CUG or the nontoxic siCGA/UCG, and subjected the RNA 48 hours after transfection to a RNA-Seq analysis. Interestingly, in the cells transfected with siCAG/CUG, 3466 genes were down and 867 genes were upregulated (>1.5 fold, adjusted p value<0.05) (data not shown). A DAVID gene ontology analysis of the upregulated genes did not reveal any evidence of an interferon response by the cells induced by the transfected siRNA (data not shown). In cells transfected with the nontoxic siCGA/UCG, only 194 genes were found to be downregulated and 420 genes upregulated.

Figure 3D:
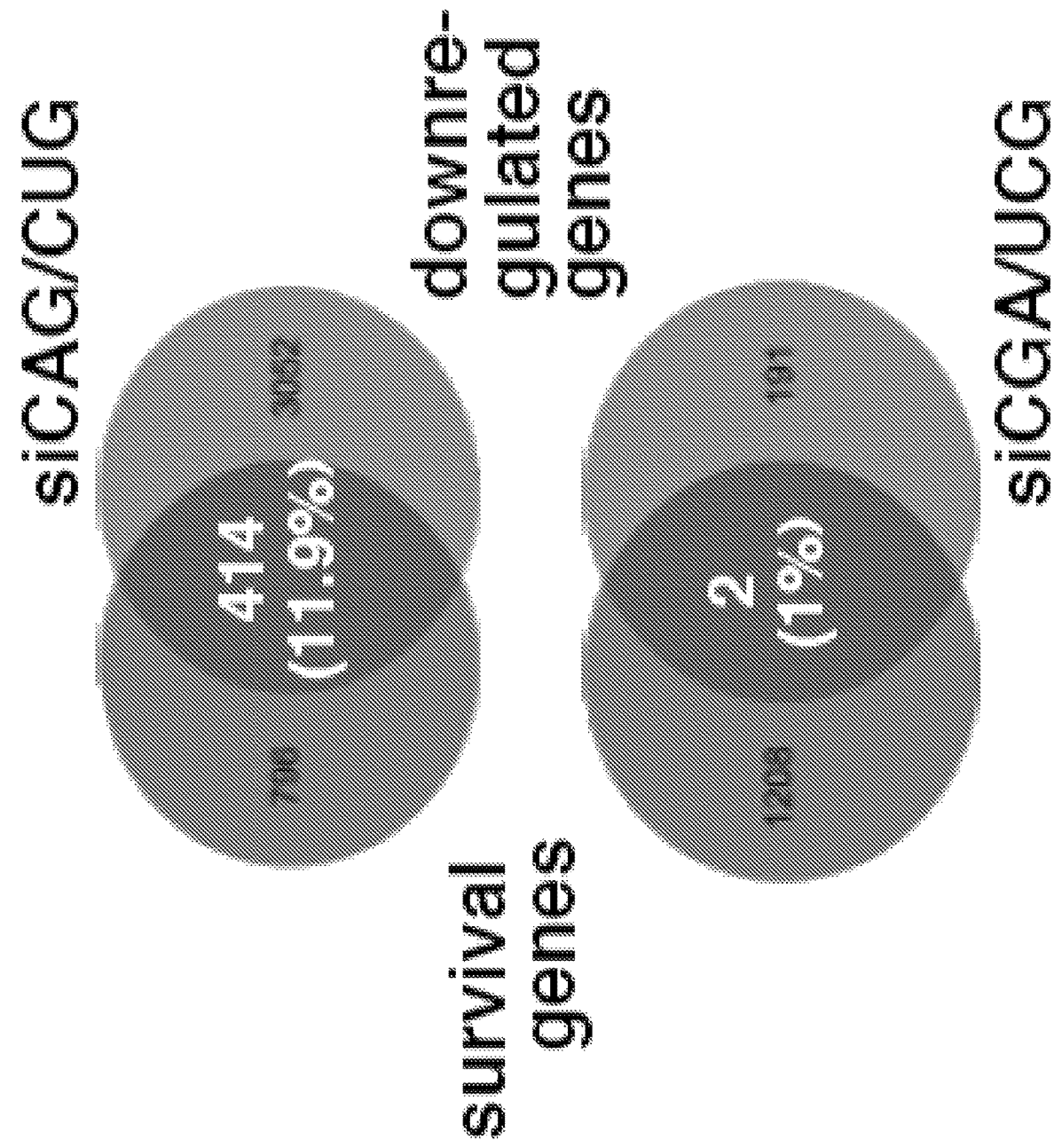

We performed a gene set enrichment analysis for a group of ~1800 survival genes and ~400 nonsurvival genes that were identified in a genome-wide CRISPR lethality screen [45] after transfecting cells with either siCAG/CUG or siCGA/UCG using a. non-targeting siNT served as a control. Similar to cells undergoing DISE, when transfected with siCAG/CUG, the ~1800 critical survival genes but not the ~400 nonsurvival control genes [15] were significantly enriched in the downregulated genes in cells transfected with siCAG/CUG but not in cells transfected with siCGA/UCG (data not shown). In fact, we detected a ~12-fold increased percentage of survival genes compared to the non-survival genes among the downregulated RNAs in the siCAG/CUG treated cells (FIG. 3D)—a higher difference than seen in cells treated with DISE-inducing sh- or siRNAs (data not shown).

We also performed a metascape analysis of 4 RNA-Seq data sets of cells into which were introduced siL3, two CD95L derived shRNAs (shL1 and shL3), a CD95 derived shRNA (shR6) ORF, previously described [15], and the downregulated genes in cells transfected with siCAG/CUG. The Metascape gene ontology analysis comparing the downregulated genes in cells treated with either CD95 or CD95L derived si- or shRNAs with the data from the siCAG/CUG treated cells showed a strong overlap in the GO terms including cell cycle, response to DNA damage, mitosis, and chromatin organization suggesting that cells died through a mechanism similar to DISE (data not shown). When the RNA-Seq data of cells treated with siCGA/UCG was included in the analysis, not a single GO cluster overlapped (data not shown).

Figure 3E:
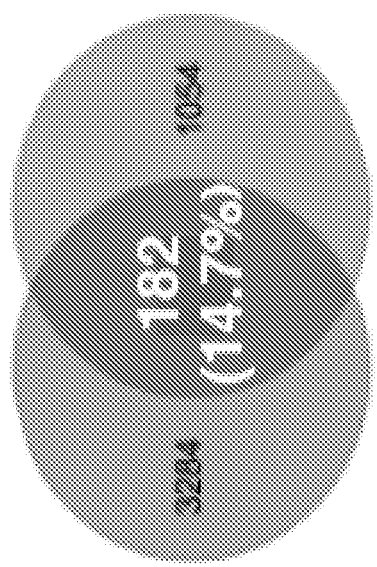

Interestingly, a large genome-wide comparison of lymphoblastoid cell lines from 107 HD patients reported an inverse correlation between CAG repeat length and downregulated genes. Biological pathways that were significantly affected were ribosomal process, energy metabolism and cell death pathways [24] all consistent with reduced cell viability. We compared the genes that were reported to be negatively and significantly correlated with the length of the CAG repeats in these patients (1236 genes, according to Pearson correlation) with the 3466 genes downregulated in the HeyA8 cells transfected with siCAG/CUG. Of the 1236 genes downregulated in the patients 182 (14.7%) were also downregulated in the siCAG/CUG treated HeyA8 cells (FIG. 3E). In a DAVID gene ontology analysis with these 182 genes the two most significantly enriched clusters were consistent with genes playing a role in cell division and mitosis, consistent with a major effect of siCAG/CUG on mitosis (data not shown). In summary, these data suggest that the toxicity of the CAG repeat based siRNA may involve loss of survival genes and that this form of cell death could be related to the TNR activities seen in patients with extended CAG repeats.

Super toxic TNR-derived siRNAs kill cells by targeting TNR sequences present in the ORF of genes complementary to the toxic siRNA guide strand. To determine which genes and what part of the mRNAs could be targeted by toxic TNR-derived siRNAs, we subjected ranked lists of down-regulated genes of cells treated with either siCAG/CUG or siCGA/UCG to a Sylamer analysis [25]. This method detects enrichment of seed matches in mRNAs that are complementary to the seed of the introduced siRNAs. In particular, we performed a 6-nucleotide Sylamer analysis of the ORFs and the 3'UTRs of genes deregulated in HeyA8 cells transfected with either siCAG/CUG or siCGA/UCG and ordered the genes from most down-regulated to most up-regulated.

When the seed length was set to 6 nts, we detected a minor enrichment of the 6 mer TGCTGC in the 3'UTRs of the downregulated genes in the cells treated with siCAG/CUG. TGCTGC is the expected seed match (position 2-7) of the siCAG 19 mer guide strand (data not shown). No significant seed match enrichment was found in cells treated with siCGA/UCG or when the ORFs of these genes were analyzed.

We also performed a 10-nucleotide Sylamer analysis of the ORFs and 3'UTRs of genes deregulated in HeyA8 cells transfected with either siCAG/CUG or siCGA/UCG and ordered the genes from most down-regulated to most up-regulated. The three most highly enriched sequences were as follows:

ORF 10-mers, siCAG/CUG: CTGCTGCTGC (SEQ ID NO:9), TCTGAGACCA (SEQ ID NO:10), TGCTGCTGCT (SEQ ID NO:11)

ORF 10-mers, siCGA/UCG: GGGGGTGGGG (SEQ ID NO:12), CCTCCCTCCC (SEQ ID NO:13), CCCCGCCCCC (SEQ ID NO:14)

3'UTR 10-mers, siCAG/CUG: GGCCCTGGCC (SEQ ID NO:15), CACTCCCCAC (SEQ ID NO:16), GGCAGGGGTG (SEQ ID NO:17)

3'UTR 10-mers, siCGA/UCG: GGGGGTGGGG (SEQ ID NO:18), CCTCCCTCCC (SEQ ID NO:19), CCCCGCCCCC (SEQ ID NO:20)

When we analyzed the ORFs of cells treated with siCAG/CUG when setting the seed length to the maximum of 10 nts, we found a very profound enrichment of two 10 nt sequences (p-value ~$10^{-50}$) that corresponded to positions 1-10 and 2-11, respectively of the targeting siCAG 19 mer, which were CTGCTGCTGC (SEQ ID NO:9) and TGCTGCTGCT (SEQ ID NO:11). No such enrichment was found when the 3'UTRs of the genes were used for the analysis. These data suggest that in contrast to DISE-inducing si/shRNAs, siCAG/CUG killed cancer cells by targeting long repeat sequences located mainly in ORFs. Consistent with this conclusion, genes containing either of the two targeted 10 mers in their ORFs were very strongly enriched among the downregulated genes in siCAG/CUG treated cells, while only a weak enrichment was found when the 3'UTRs were analyzed.

Figure 4A:
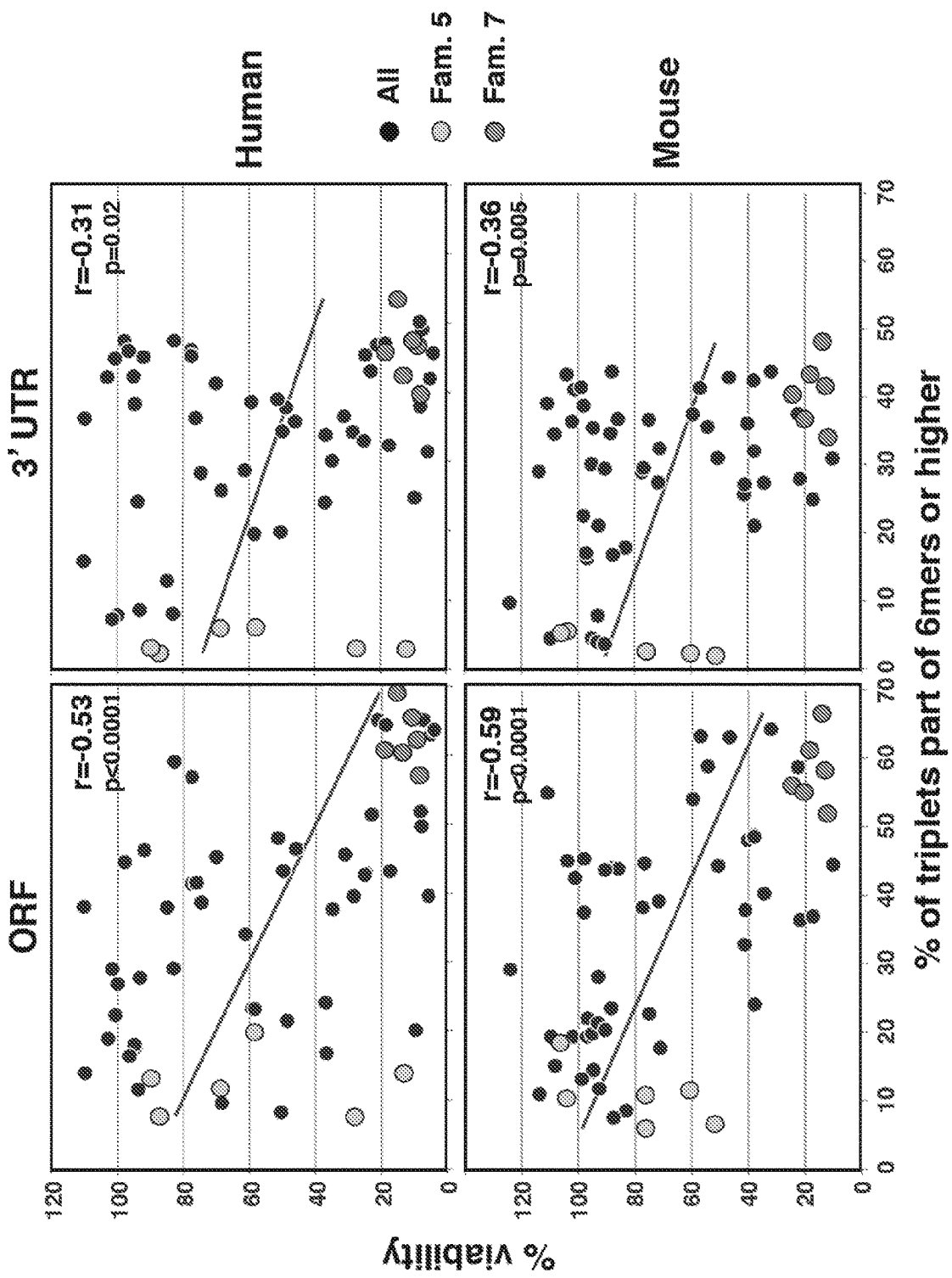
Figure 13:
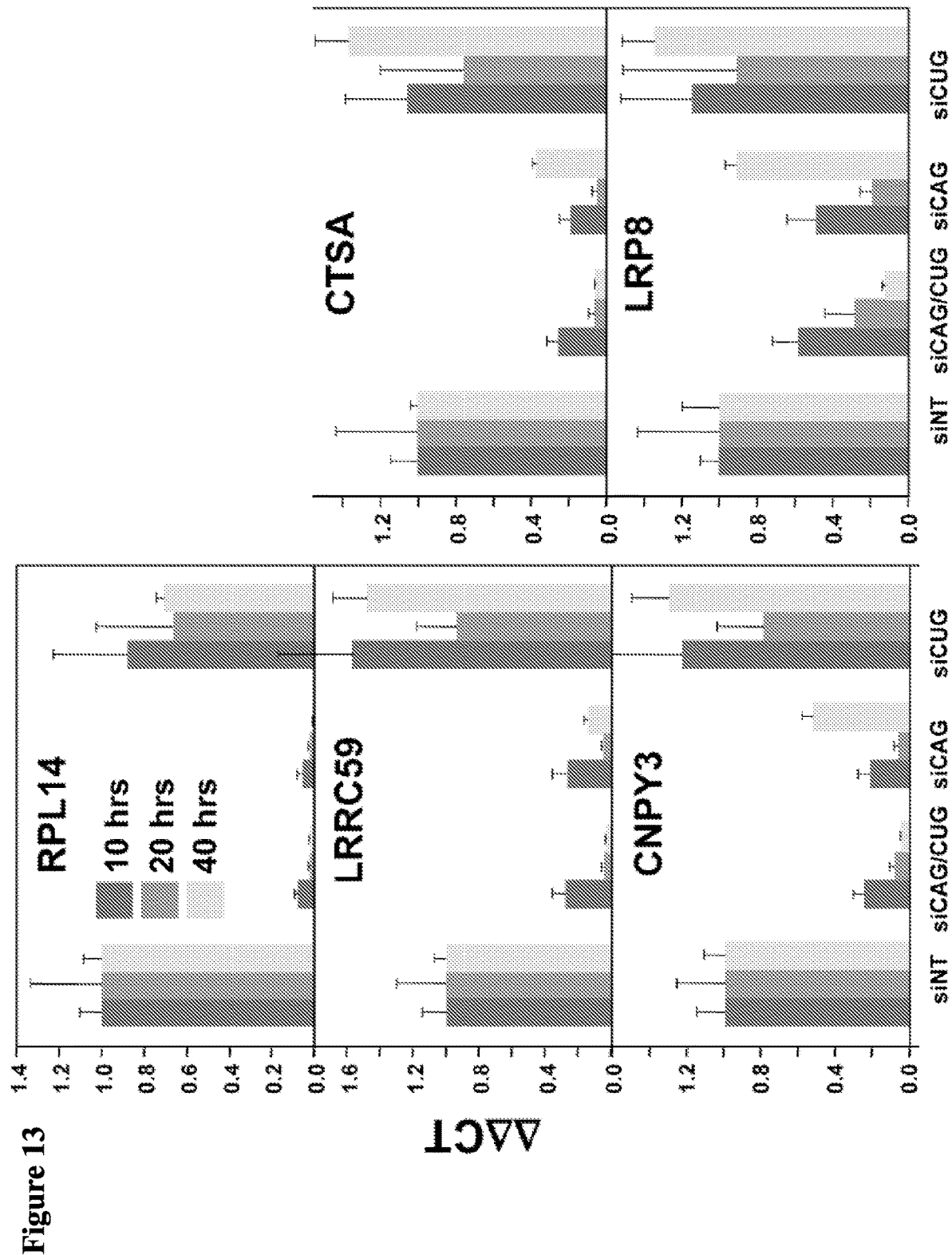
FIG. 13. Efficient knockdown of CUG repeat containing genes in cells transfected with siCAG. HeyA8 cells were transfected with 1 nM of either siNT, siCAG/CUG, siCAG (with the CUG containing passenger strand modified by 2'O-methylation), or siCUG (with the CAG containing passenger strand modified by 2'O-methylation). RNA was quantified by real-time PCR. The genes are ranked according to their highest fold downregulation in the RNA Seq experiment. Values are mean−/+SD. n=2 biological replicates (for siNT and siCAG/CUG), 3 technical replicates each.
Figure 14A:
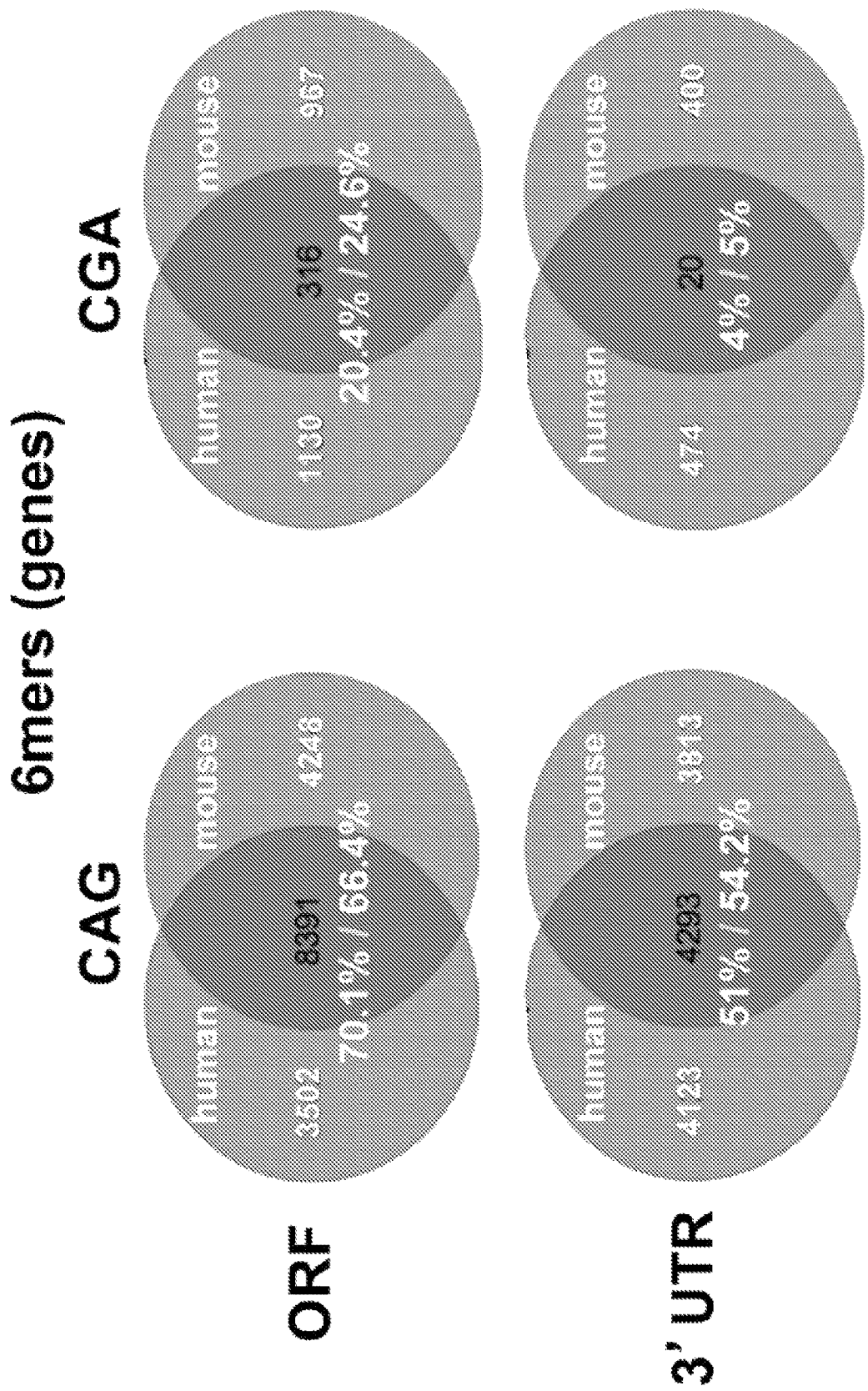
FIGS. 14A and 14B. Genes containing the 19 mer targeted by siCAG are poorly conserved between human and mouse.
Figure 14B:
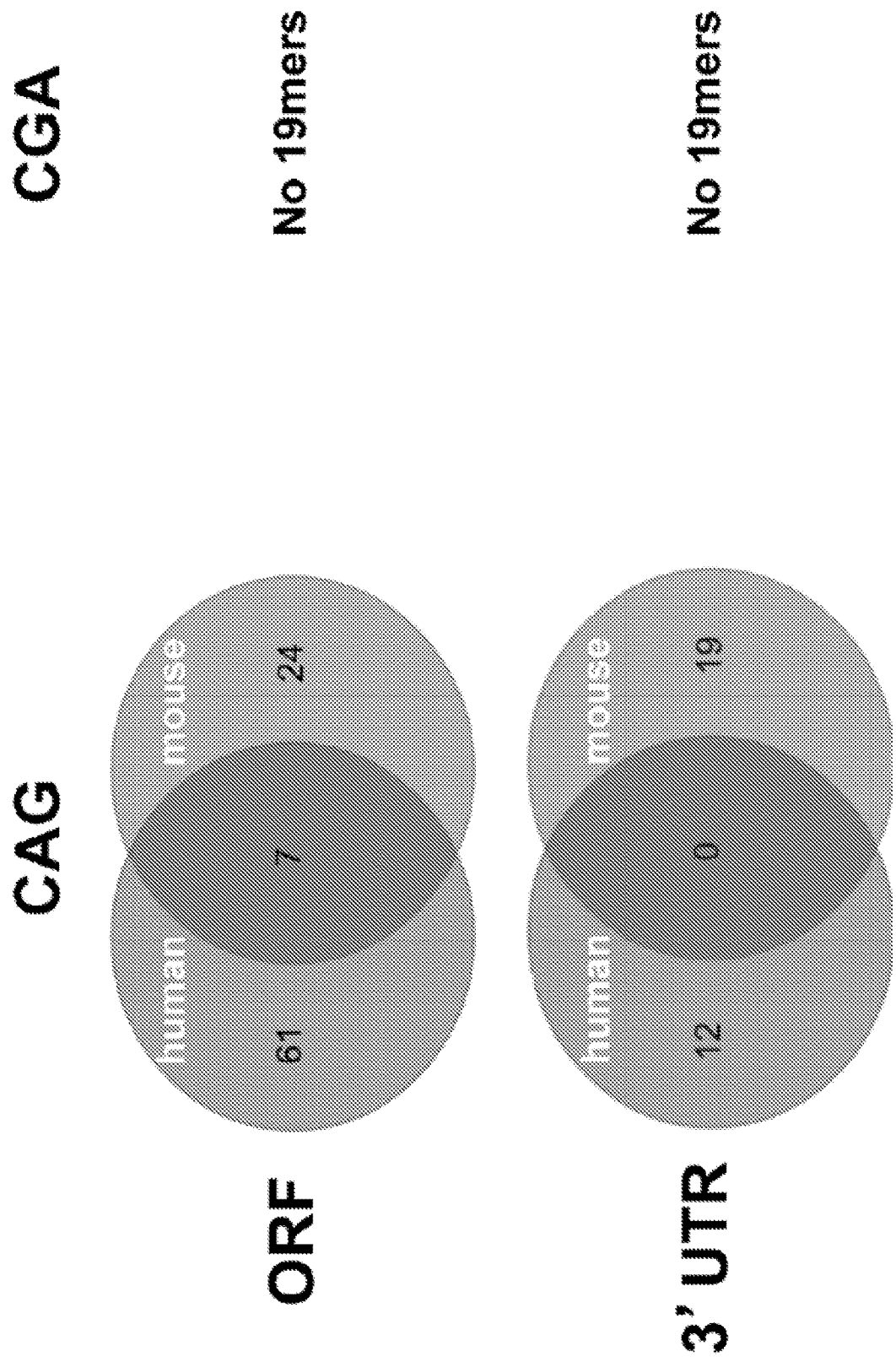

Now knowing that the toxicity of the siCAG/CUG correlated with the presence of targeted trinucleotide repeats found in the ORFs of genes, we wondered whether the toxicity across all 60 TNR derived siRNAs correlated with the presence of higher ordered reverse complementary TNRs in ORFs that could be targeted by the TNR siRNAs and whether this was conserved between human and mouse cells. We analyzed the frequencies of all triplets combined in mouse and human ORFs and 3'UTRs and counted the number of genes containing 6 mers, 10 mers, or 19 mers targeted by the 60 TNRs. We also performed a set enrichment analysis for genes containing a GCTGCTGCTGCTGCTGCTG (SEQ ID NO:21) 19 mer (targeted by the siCAG 19 mer) in their ORFs and 3'UTRs in cells transfected with siCAG/CUG when compared to cells transfected with siNT. When counting all 60 single triplets in both the ORFs and 3'UTRs of all human and mouse genes they were found to be slightly more abundant in the ORF of genes. When separating into individual triplets of the 10 families most triplets are found at similar frequencies in both the ORFs and 3'UTRs in humans and in mice. This situation changed when we focused on targeted (reverse complements of the targeting TNRs) repeats. We plotted the results for 6 mers (as this is the minimum sequence required for RNAi-based targeting), 10 mers (the maximum seed length allowed by Sylamer), and 19 mers (the length of the siRNAs used). In all cases, with longer sequences, the preference for certain triplets became clearer. When analyzing the 19 mers, in both human and mouse, the most abundant TNRs are members of the super toxic family 7 and barely any 19 mers were found in the related family 5. Genes containing the 19 mer TNR (or longer) in their ORF targeted by siCAG were enriched in the most down-regulated genes in cells transfected with siCAG/CUG. We selected 5 of the 6 most highly expressed and downregulated genes from the RNA-Seq analysis for validation (FIG. 13). HeyA8 cells were transfected with siRNAs at 1 nM, and the mRNAs levels were quantified by real time PCR 10, 20 or 40 hrs after transfection. When transfecting siCAG/CUG all 5 CUG repeat-containing mRNAs were downregulated as early as 10 hrs with maximal downregulation at 40 hrs. Specificity of the targeting was established by transfecting the cells with either siCAG or siCUG (in which the passenger strand was disabled by adding the 2'-O-methylation). Only the siCAG-based siRNAs were active in silencing the CUG TNR containing genes. These data strongly suggested that the toxicity of TNR-based siRNAs in general might be explained by the presence of extended reverse complementary repeat sequences present preferentially in the ORF of targeted genes. This was confirmed by plotting the viability of cells treated with any of the 60 TNR siRNAs and the number of targeted TNR sequences of 6 nts or longer (FIG. 4A). The highest and most significant correlation was found for both human and mouse ORFs. Remarkably, while 80-90% of triplets targeted by the 6 members of the CGA containing family 5 are present as singular events (blue dots), between 50 and 70% of the triplets targeted by members of the CAG containing family 7 are found to be part of 6 mers or higher ordered TNRs (red dots). Interestingly, the TNRs targeted by the 6 toxic members of family 7 code for 5 different amino acids (FIG. 4B). As all the 6 members of family 7 are equally toxic to cancer cells, this suggests that this involves targeting long repeat elements (i.e. TNRs), rather than a requirement for poly-homo amino acid coding stretches. This view is supported by an analysis of species conservation (FIG. 14). Of the genes that contain targeted 19 mers, only 7 of the 99 genes found in either the mouse and the human genome overlapped and the genes that are targeted do not have shared functions (FIG. 14B). In summary, our data provide evidence that TNR-based siRNAs are toxic to cells by targeting a number of genes that contain high order trinucleotide repeats that are reverse complementary to the targeting TNR. The resulting cell death has features of what we recently described as DISE, with the main difference that DISE is the result of a miRNA-like targeting of short seed matches in the 3'UTRs of survival genes, whereas the TNR-induced cell death is an on-target effect affecting a larger number of genes that contain targeted sequences in their ORF. This now provides an explanation for why the most toxic TNR-based siRNAs are much more toxic than DISE-inducing siRNAs. Intriguingly, the CAG repeats found in HD are part of the most toxic family of TNRs and their reverse complementary 19 mers that can serve as targets are the most abundant TNR sequences in the ORFs of both human and mouse genomes.

Figure 5A:
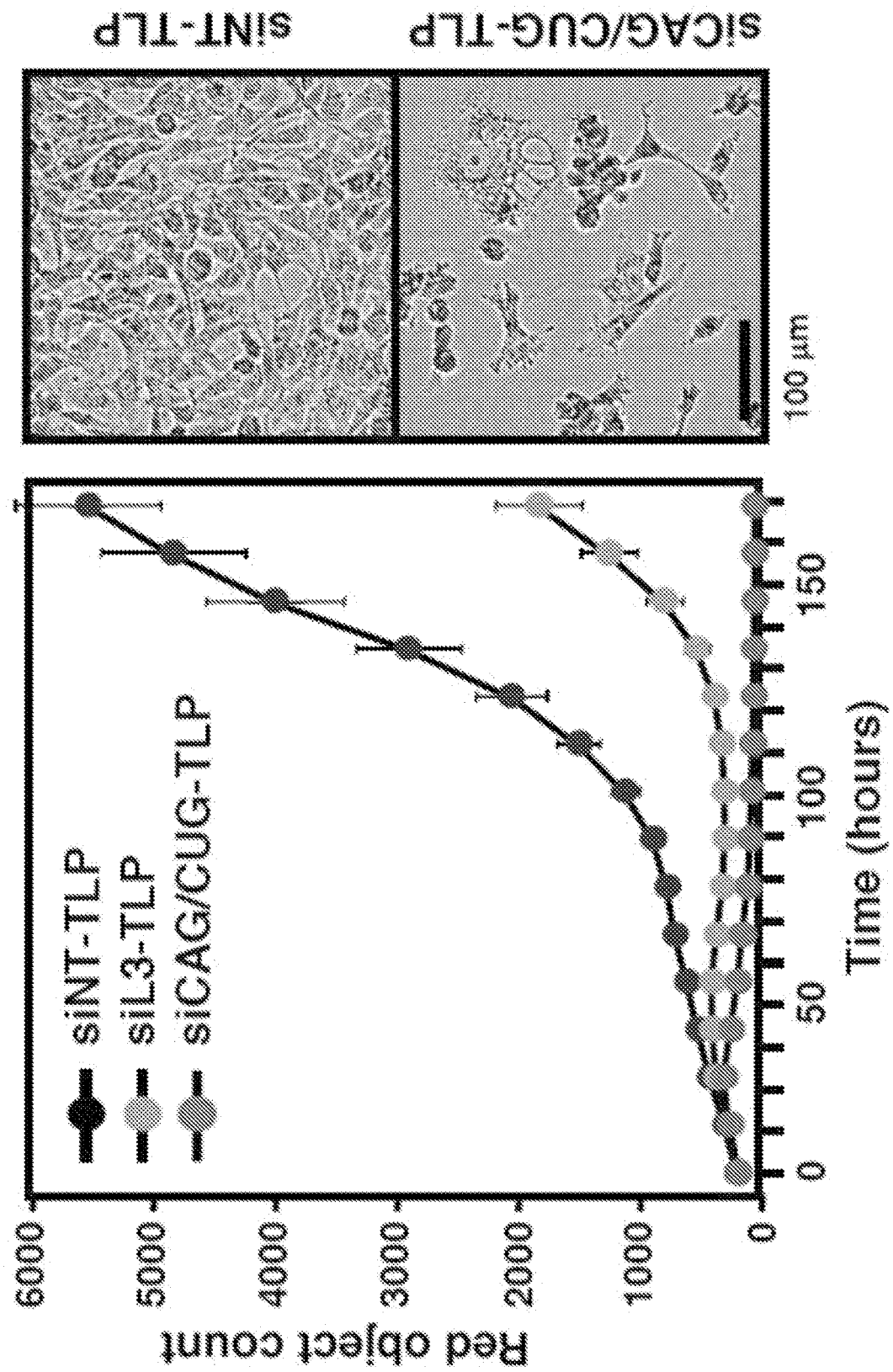
FIGS. 5A-G. Killing cancer cells using siCAG/CUG coupled to TLP nanoparticles both in vitro and in vivo.
Figure 5B:
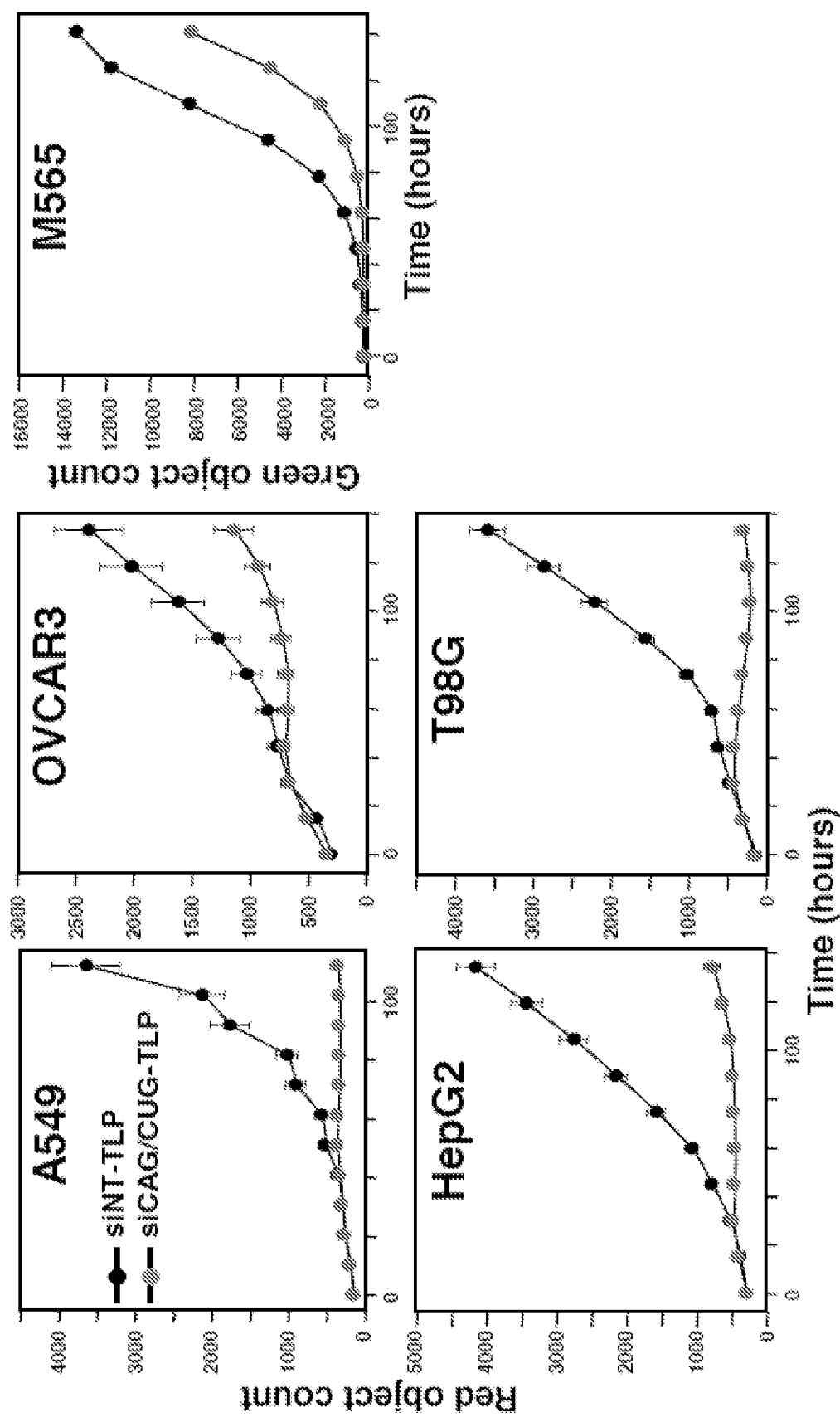
Figure 5C:
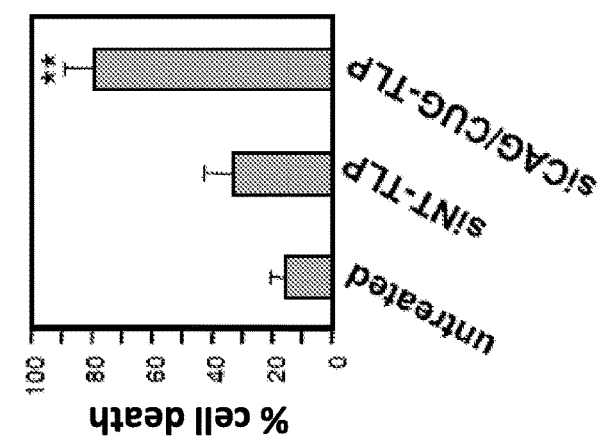
Figure 5D:
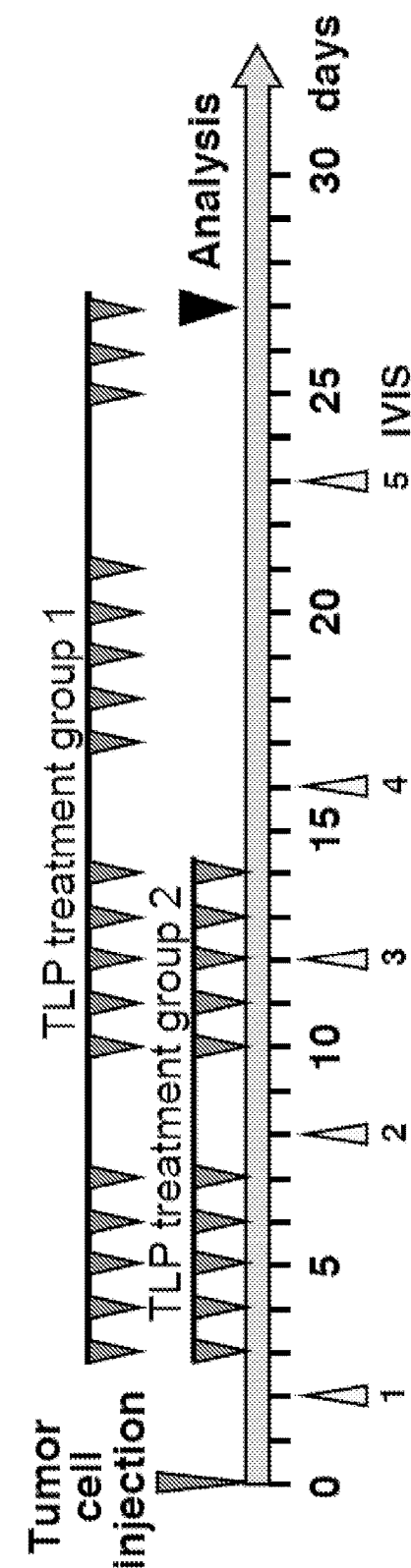
Figure 5E:
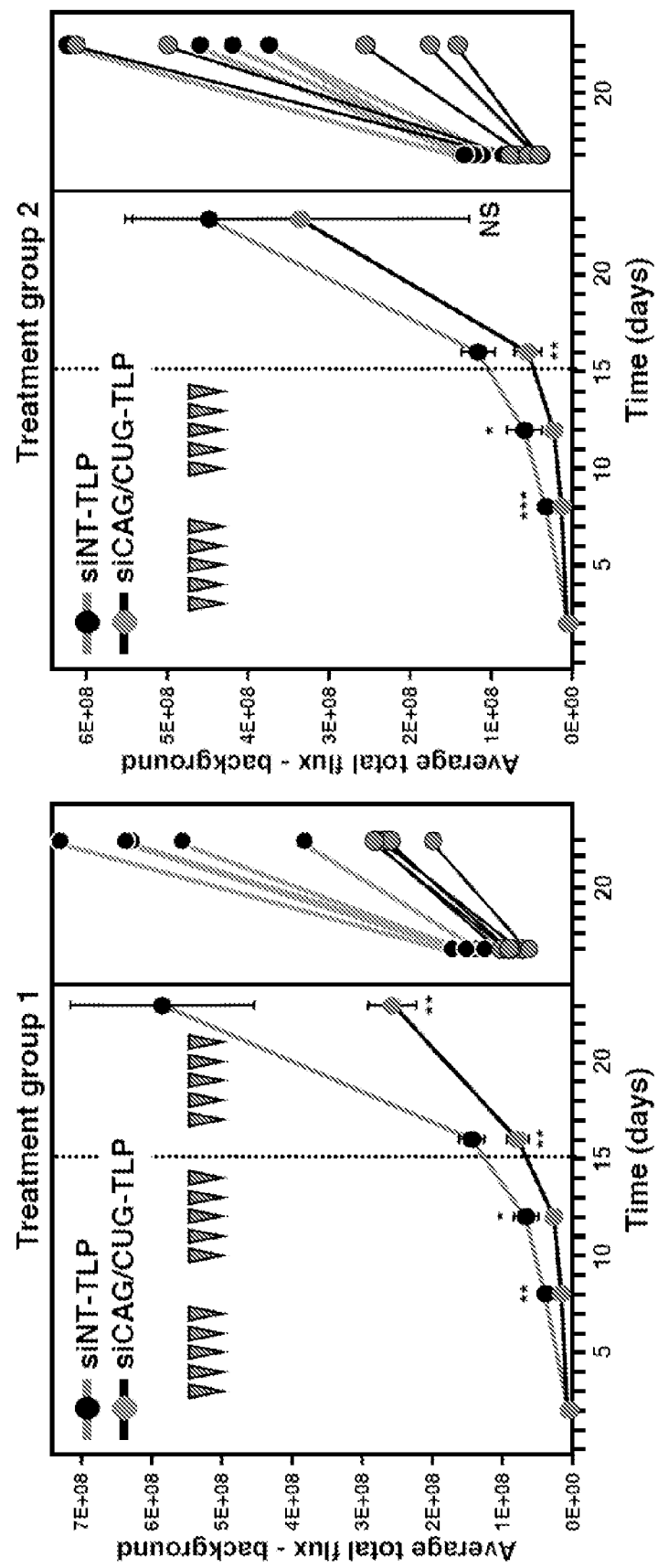

Super toxic CAG/CUG TNR based siRNAs slow down tumor growth in vivo with no toxicity to normal tissues. We were wondering whether the super toxic TNR-based siRNAs could be used for cancer therapy. We decided to deliver the siRNAs to cancer cells in vivo using templated lipoprotein (TLP) nanoparticles [26]. Before using the TLP particles loaded with the siCAG/CUG duplex (siCAG/CUG-TLP) in vivo, we tested their effects on tumor cells in vitro. They killed HeyA8 cells more efficiently than siL3-TLPs (FIG. 5A) and also slowed down growth of the tested human or mouse cancer cell lines (FIG. 5B and data not shown). They also killed neurospheres derived from patients with glioblastoma (FIG. 5C). To test the activity of the siCAG/CUG-TLPs in vivo we treated orthotopically xenografted HeyA8 ovarian cancer cells in mice. Mice injected with 100,000 tumor cells were i.p. injected with nano particles 5 times a week for two weeks (FIG. 5D). After the tenth treatment mice were split into two groups, one group continued to receive treatment in the third week and the second group did not. This was done to determine whether large established tumors would still respond to the treatment. The large tumors in treatment group 1 still benefited from the effect of siCAG/CUG in the third week of treatment (FIG. 5E, left panel). In contrast, some tumors in the mice in treatment group 2 grew out rapidly, while others showed persisting growth reduction (FIG. 5E, right panel). These results suggest that established tumors respond to the siCAG/CUG treatment. This was confirmed in another experiment in which $10^6$ HeyA8 cells were injected and mice were first treated 3 times a week and then switched to daily treatment 19 days after tumor cell injection (data not shown).

Figure 15B:
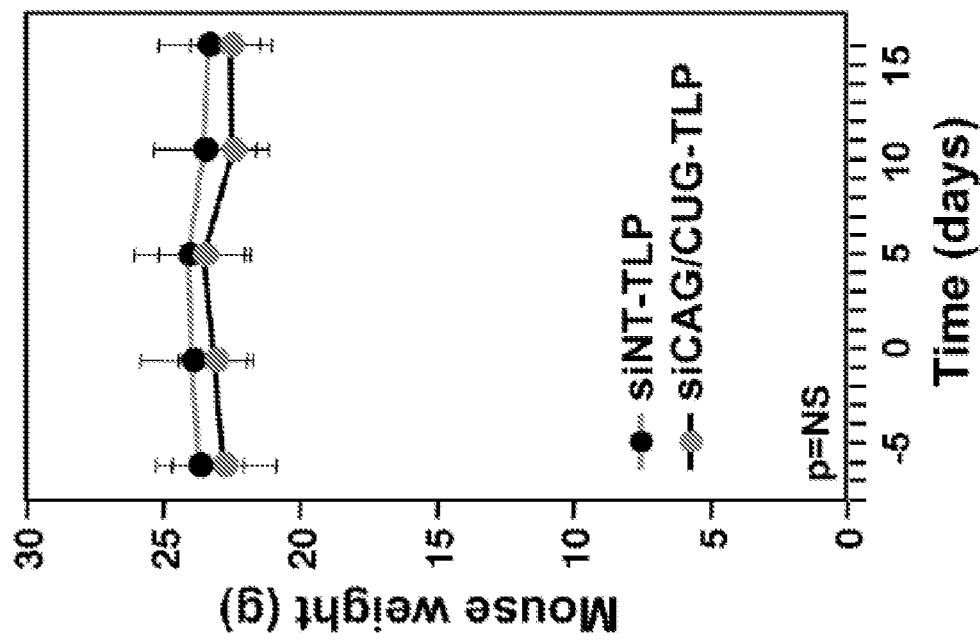
Figure 15A:
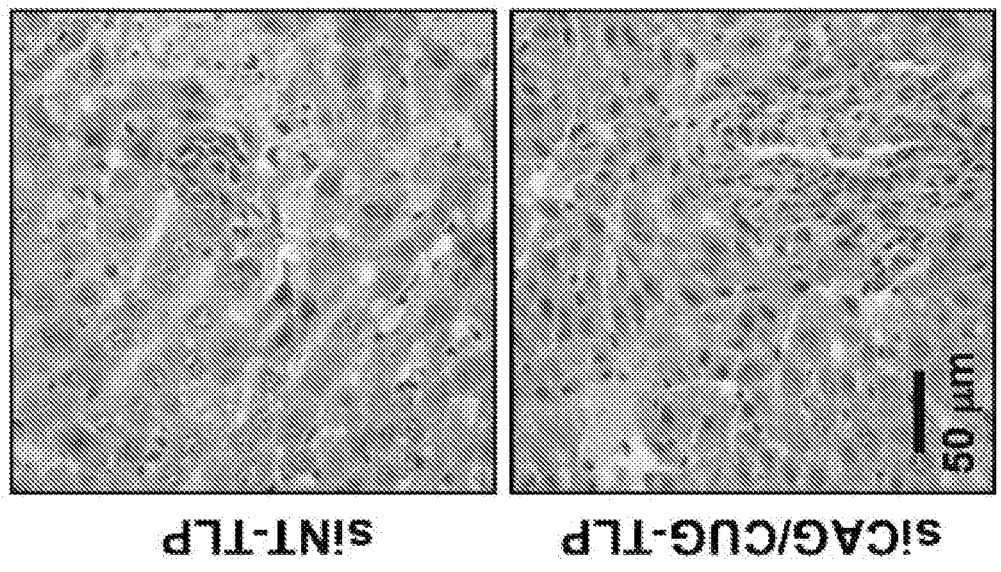

To determine whether siCAG/CUG was detrimental to mice, mice in treatment group 1 were treated a few more times with the siRNA and were analyzed just when the control treated mice were moribund at around day 27. We did not see any signs of toxicity in any of the mice. They were feeding well (not shown), did not lose weight (FIG. 15A), had normal liver histology (FIG. 15B), and showed no increase in liver enzymes in the serum (FIG. 15C). These data demonstrated that super toxic CAG/CUG TNR-based siRNAs delayed tumor growth in vivo 5-6 days with no gross toxicity to normal cells and that they could be safely administered using TLP nanoparticles.

Figures 5F, 5G:
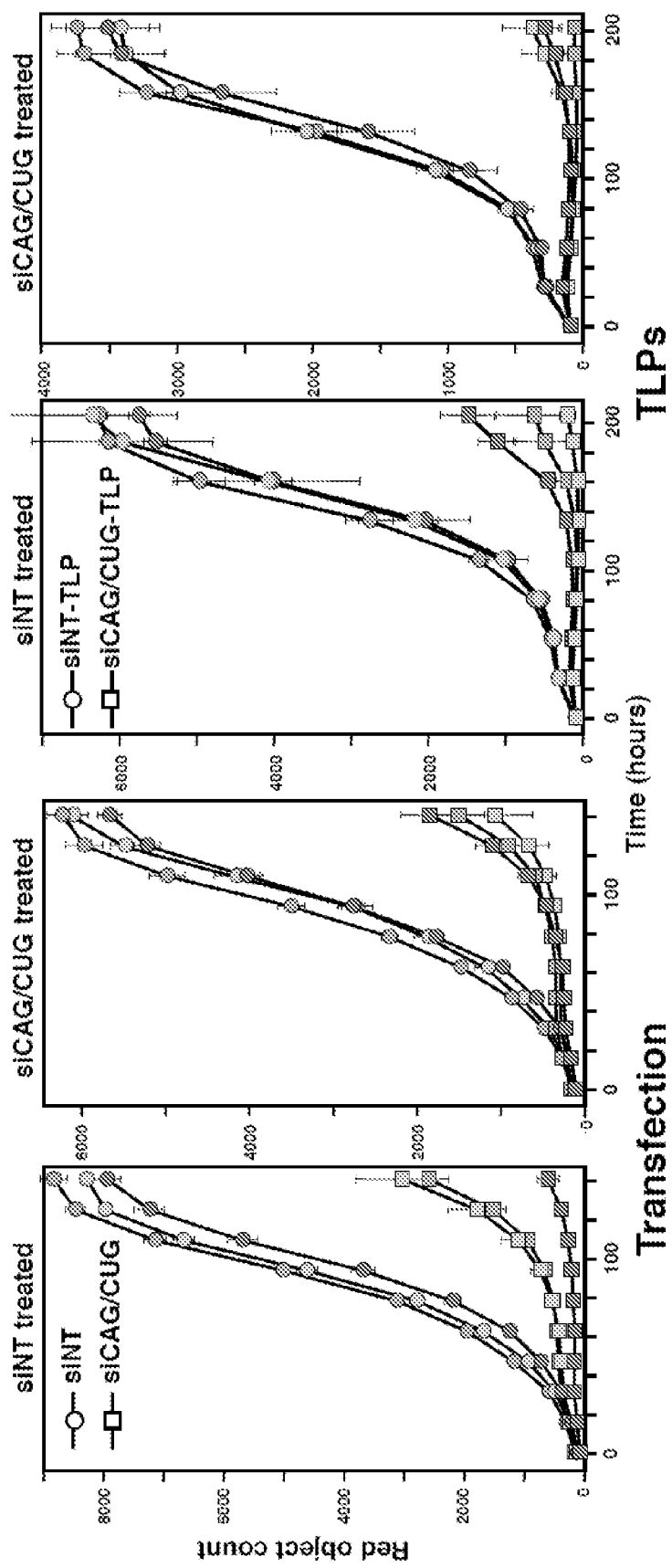

To determine whether tumor cells acquired resistance to the treatment, we tested tumors from three mice in treatment group 1 ex vivo. Three tumors of mice treated with siNT-TLP and three tumors of mice treated with siCAG/CUG-TLP were transfected with the same siRNAs in vitro a day after tumor isolation (FIG. 5F). In parallel, these tumor cells were also treated with the nanoparticles again (FIG. 5G). In all cases, the tumors from the mice that had received the toxic siRNA were as sensitive to the toxic effects of siCAG/CUG in vitro as the tumors from mice treated with siNT suggesting that cancer cells cannot become resistant to cell death induced by the toxic TNR-based siRNAs, at least not in the classical sense observed after targeted therapy, and that preferentially tumor cells were responding as there were no signs of toxicity in the mice.

Discussion

The siRNA we used for cancer treatment was a duplex between the basic TNR module found in HD (CAG) and the fully complementary strand CUG found in Myotonic Dystrophy (DM1). In a screen of all TNR-derived siRNAs both CAG and CUG were part of a family that contains 6 members all of which were highly toxic to cancer cells of both human and mouse origin. This hybrid duplex between the two disease molecules was also recently tested in a well-established *Drosophila* model of DM1 [27]. Expression of the two transcripts led to the generation of Dicer-2 (dcr-2) and ago2-dependent 21-nt TNR-derived siRNAs resulting in high toxicity to the cells. In a separate study, it was shown that expression of these complementary repeat RNAs leads to dcr-2-dependent neurodegeneration [28]. These results suggest that co-expression of CAG and CUG repeat-derived sequences may dramatically enhance toxicity in human repeat expansion diseases in which anti-sense transcription occurs. Antisense transcription was reported to occur in SCA8 in two genes encompassing the repeats are expressed: ATXN8 (CAG repeat), on the sense strand and ATXN8OS (CTG repeat) on the antisense strand [29].

One could argue that a cancer therapy based on delivering siCAG/CUG could be detrimental to patients as TNR expansion patients suffer from various pathologies. However, similar to many other genes with amplified CAG repeats, HTT is ubiquitously expressed throughout the body with somewhat higher expression in the brain and in testis [30]. The disease is characterized by neurodegeneration affecting the cerebral cortex and neuropathology in the striatum, but it also affects other tissues [31]. So, if sCAGs are produced in multiple tissues the effects on most normal tissues seems to be moderate. Even in the brain, while detrimental to HD patients long term, most patients do not have major symptoms before the age of 40 [4, 31]. Short-term exposure to toxic sCAGs for cancer therapy, as suggested by our mouse experiments, may not have a dramatic effect on normal tissues but may be enough to kill cancer cells. If a CAG based siRNA were to produce side effects particularly in the brain it may be possible to protect the brain through local administration of neuroprotecting LNA-CTGs as described [14].

What could be the mechanism of the relative resistance of normal versus tumor cells to the toxic siRNAs? Our recent data suggested that miRNAs inhibit DISE and in fact may protect normal cells from it [15]. Both Drosha and Dicer k.o. HCT116 cells were found to be hypersensitive to a DISE inducing siRNA. This is entirely consistent with reported activities of CAG repeats which may also act though RNAi. Pathogenic Ataxin-3 with amplified CAG repeats showed strongly enhanced toxicity in HeLa cells after knockdown of Dicer [32]. In addition, it was previously shown in *Drosophila* that impairing miRNA processing dramatically enhanced neurodegeneration caused by the CAG repeat gene Ataxin-3. Two fly mutants were tested, one with a deficiency in dcr-1, the *Drosophila* Dicer ortholog that is required for miRNA biogenesis, and another with a deficiency in R3D1, a gene required for dcr-1 to function [33]. The authors concluded that "miRNA pathways normally play a protective role in polyQ-induced neurodegeneration". In the light of our data it is possible that miRNAs might actually protect cells from the toxic effects of TNR based siRNAs.

While HD is the best known disease caused by CAG repeats, one of the two diseases first discovered to be caused by TNR repeat expansions is the neurodegenerative disorder SBMA/Kennedy disease [34] wherein the pathogenic CAG repeat is found in exon 1b of the androgen receptor (AR). If patients with amplified CAG repeats produce sCAGs, which according to our work may be detrimental to cancer cells, one would have to expect that such patients have a reduced cancer incidence due to toxic siRNA expression in many tissues. Indeed reduced cancer incidence was reported for HD and SBMA patient populations in Sweden [18], and HD patients in France [19], Denmark [20], and England [21].

Possibly the clearest connection to cancer has been reported for the CAG repeats in the AR gene and prostate cancer (PCa). The CAG repeat length in the AR has been inversely linked to PCa. While longer repeats (>20 CAGs) confer a protective effect among the PCa patients 45 years or older [35], shorter CAG repeats have been shown to result in a two-fold increased cancer risk [36], a more aggressive disease, and a high risk of distant metastases [37-39]. Shortening of CAG repeat length was found in in situ lesions of PCa and its possible precursors [40], suggesting that PCa avoids longer CAG repeats. This is consistent with our finding of super toxicity of CAG based siRNAs.

There are two observations that suggest the targeted TNRs present in the ORFs of certain genes are not there because these proteins require stretches of the same amino acid for their function which would presumably be conserved between human and mouse: first, all six members of the TNR family 7 were super toxic targeting 6 different reverse complementary TNRs that code for 5 different amino acids (FIG. 4B), and second, the genes with the longest repeats with complete complementarity to the most toxic siCAG/CUG of 19 nts showed little overlap between human and mouse (FIG. 14B) and the different targeted genes do not share similar functions based on a Metascape analysis (data not shown). Interestingly, both the AR and the HTT genes contain some of the longest CAG repeats in the human genome, however, those are not found in the mouse orthologs at the same positions in the ORF.

So, if there was no pressure to maintain these TNRs in specific genes but rather anywhere in the genome, could there be an evolutionary link between TNRs and cancer? A hint may come from the way the repeat expansion are generated. It is believed that among other mechanisms DNA replication slippage and/or defective base excision repair causes expansion of TNRs [41]. Therefore CAG repeats could be part of a mechanism used during evolution to maintain genome integrity and, in the context of multicellular organisms, to prevent cancer formation by producing toxic siRNAs. This would occur whenever too many mutations start accumulating in cells, one property all cancers have in common.

While the treatment with siCAG/CUG requires optimization, our data on the toxicity of CAG TNR based siRNAs for cancer cells but not normal cells when administered in vivo and the reported decreased incidence rate for different types of cancer in patients with CAG expansions suggest that TNR-based siRNAs may be useful for cancer therapy.

Materials and Methods

Cell lines and tissue culture. All cells were grown in an atmosphere of 5% carbon dioxide ($CO_2$) at 37° C. Unless indicated otherwise base media were supplemented with 10% heat-inactivated fetal bovine serum (FBS; Sigma-Aldrich) and 1% penicillin/streptomycin and L-Glutamine (Mediatech Inc.). Cells were dissociated with 0.25% (w/v) Trypsin-0.53 mM EDTA solution (Mediatech Inc.). The following cell lines were cultured in supplemented RPMI1640 Medium (Mediatech Inc.): Ovarian cancer cell lines HeyA8 (RRID:CVCL_8878), OVCAR3 and OVCAR4 (both from Tumor Biology Core, Northwestern University), and lung cancer cells A549 (ATCC CRM-CCL-185) and H460 (ATCC HTB-177). The GBM cell line T98G (ATCC CRL1690) was cultured in Eagle's Minimum Essential Medium (EMEM) (ATCC). Melanoma B16F10 cells (ATCC CRL-6475) and 293T cells (RRID:CVCL_0063) were cultured in DMEM (Cellgro). HepG2 (ATCC HB-80645) was cultured in EMEM (ATCC). IDB, a mouse ovarian cancer cell line, was cultured in DMEM supplemented with 4% FBS, and 10 mg/l Insulin, 5.5 mg/l Transferrin, 6.7 µg/ml Selenium (ITS, Mediatech, Inc., 1:10 diluted). and 3LL Lewis lung cancer cells (ATCC CRL-1642) were cultured in DMEM. FOSE2 cells are spontaneously immortalized ovarian surface epithelial cells, and M565 cells are from a spontaneously formed liver cancer in a female and male mouse, respectively, both isolated from mice carrying a floxed Fas allele [17]. Both were cultured in DMEM/F12 (Gibco #11330), 1% ITS (Insulin-Transferrin-Selenium Gibco 51300-044). M565 cells were dissociated with Accutase detachment reagent (Fisher Sci.). HCT116 Drosha$^{-/-}$ were generated by Narry Kim [42]. HCT116 parental (cat #HC19023, RRID:CVCL_0291) and the Drosha$^{-/-}$ clone (clone #40, cat #HC19020) were purchased from Korean Collection for Type Cultures (KCTC). All HCT116 cells were cultured in McCoy's medium (ATCC, cat #30-2007). Mouse Ago1-4 k.o. embryonic stem cells inducibly expressing human FLAG-HA-AGO2 were described in [43]. CELLSTAR tissue culture dishes (Greiner Bio-One, cat #664160, cat #639160) were coated with 0.1% Gelatin solution (Sigma, cat #ES-006-B) for 10 to 30 minutes before use. Cells were cultured in DMEM media (Gibco, cat #12430054) supplemented with 15% Fetal Bovine Serum (Sigma, cat #F2442), 1% NEAA solution (HyClone, cat #SH3023801), 1% GlutaMAX 100× (Gibco, cat #35050061),-0.0007% 2-Mercaptoethanol (Fisher, cat #BP176100), and $10^6$ units/L LIF (Sigma, #ESG1107). The cell culture media was refreshed daily. FLAG-HA-AGO2 is under the control of a TRE-Tight (TT) doxycycline (Dox)-inducible promoter. 100 ng/ml doxycycline (Sigma, cat #D9891) was added to the media in order to induce moderate level of Ago2 expression to maintain normal cell growth. To deplete Ago2 expression in cells, doxycycline was withdrawn from media for 4 days. To induce wild type level of hAgo2 expression, 2.5 µg/ml doxycycline was added to the media. The human GBM derived neurosphere cell line GIC-20 (infected with pLV-Tomato-IRES-Luciferase) was obtained from Dr. Alexander Stegh. Cells were grown as neurospheres in DMEM/F12 50:50 with L-glutamine (Corning), supplemented with 1% PenStrep, B27 (Invitrogen), N2 (Invitrogen), human-Epidermal Growth Factor (hEGF; Shenandoah Biotech), Fibroblast Growth Factor (FGF; Shenandoah Biotech), Leukemia Inhibitory Factor (LIF; Shenandoah Biotech), and GlutaMAX (Life Technologies). HeyA8 xenografted tumors nodules were dissected from mice, cut, washed in sterile PBS, and dissociated with dissociated with 0.25% (w/v) Trypsin-0.53 mM EDTA solution for 20 minutes at 37° C. The digestions was stopped by adding full RPMI-1640 medium. After centrifugation, the trypsin solution mix was removed, and the tumor cells were resuspended in fresh full medium, and strained through 70 micron cell strainer. The tumor cell suspension was plated over night on 10 cm tissue culture dishes. The following day, cells were harvested, counted, and plated on 96-well plates for further experiments. Cells were transfected with siRNAs after cells had adhered or incubated with siRNA TLPs and then plated.

Western blot analysis. Primary antibodies for Western blot: anti-β-actin antibody (Santa Cruz #sc-47778, RRID: AB_626632), anti-human AGO2 (Abcam #AB186733, RRID:AB_2713978). Secondary antibodies for Western blot: Goat anti-rabbit; IgG-HRP (Southern Biotech #SB-4030-05, RRID:AB_2687483). Reagents used: propidium iodide (Sigma-Aldrich #P4864), puromycin (Sigma-Aldrich #P9620) and Lipofectamine RNAiMAX (ThermoFisher Scientific #13778150). Western blot analysis was performed as recently described [15]

Transfection with short oligonucleotides. For transfection of cancer cells with siRNAs, RNAiMAX was used at a concentration optimized for each cell line, following the instructions of the vendor. Cell lines were either transfected after cells had adhered (forward transfection), or during plating (reverse transfection). For an IncuCyte experiment cells were typically plated in 200 µl antibiotic free medium, and 50 µl transfection mix with RNAiMAX and siRNAs were added. During growth curve acquisitions the medium was not exchanged to avoid perturbations. All individual siRNA oligonucleotides were ordered from Integrated DNA Technologies (IDT). Individual RNA oligos were ordered for the sense and antisense oligo; the sense strand had 2 Ts added to the 3' end; antisense strand had 2 deoxy As at the 3' end. When indicated the first two positions at the 5'-end were 2'-O-methylated. Sense and antisense oligos were mixed with nuclease free Duplex buffer (IDT, Cat. No #11-01-03-01; 100 mM Potassium Acetate, 30 mM HEPES, pH 7.5) to 20 µM (working solution), heated up for 2 minutes at 94° C., and then the oligos were allowed to cool down to room temperature for 30 minutes. siRNA solutions were aliquoted and stored at −80° C. The cells were transfected with siRNAs at a final concentration of 0.01 nM-10 nM. The following siRNA sequences were used: siNT (siNT #2): UGGUUUACAUGUUGUGUGA (SEQ ID NO:1) (non targeting in mammalian cells), siNT1: UGGUUUACAUGUCGACUAA (SEQ ID NO:2) (non targeting in mammalian cells), siL3: GCCCUUCAAUUACCCAUAU (SEQ ID NO:3) (human CD95L exon 1), siNT/siL3: UGGUUUA-CAUGUCCCAUAA (SEQ ID NO:4). siNT seed: UGGUAAACUAGUUGUCUGA (SEQ ID NO:5), siL3 seed: UGGUAAACUAGUCCCAUAA (SEQ ID NO:6). All TNR based 19 mer siRNAs were designed as follows: The TNR based siRNA was named according to its antisense/guide strand: 2 nt 3' overhangs were added as described above. All TNR based siRNAs were fully complementary 19 mers. For instance, the siCAG/CUG sequences are: S: CAGCAGCAGCAGCAGCAGCdAdA (SEQ ID NO:7), AS: GCUGCUGCUGCUGCUGCUGTT (SEQ ID NO:8). In all siRNAs used in screens the sense/passenger strand was disabled by 2'-O-methylation in positions 1 and 2 of the sense strand.

For transfecting Ago1-4 k.o. mouse ESC, cells were cultured without doxycycline for three days. Half of the cells were then cultured for one more day without doxycycline before transfection. The other half was cultured in media containing 2.5 µg/ml of doxycycline for one day to induce WT level AGO2 expression before transfection. For IncuCyte experiments, The ESCs were transfected with either 5 nM siNT or siCAG/CUG using reverse transfection method in a 96 well plate coated with 0.1% gelatin. 5000 cells/well and 0.2 µl RNAiMAX/well were used. One day after transfection, 100 µl of media (with or without 2.5 µg/ml doxycycline) was added to each well. After that, media was refreshed every 2-3 days until the cells grew confluent. For flow cytometry experiments, cells were transfected with either 5 nM unlabeled siNT or siNT labeled with Cy5 on the 5' end of the antisense strand using reverse transfection method in a 12 well plate coated with gelatin in triplicates. 300,000 cells/well and 1 µl RNAiMAX/well were used. Flow cytometry measurements were conducted 24 hours after transfection. For AGO2 knockdown experiment, 100,000 cells/well HeyA8 or 200,000 cells/well A549 cells were reverse transfected in 6-well plate with either non-targeting (Dharmacon, cat #D-001810-10-05) or an AGO2 targeting siRNA SMARTpool (Dharmacon, cat #L004639-00-005) at 25 nM. 1 µl RNAiMAX per well was used for HeyA8 cells and 6 µl RNAiMAX per well was used for A549 cells. 24 hours after transfection with the SMARTpools, cells were reversed transfected in 96-well plate with either siNT or siCAG/CUG at 1 nM and monitored in the IncuCyte. 0.1 µl/well RNAiMAX was used for HeyA8 cells and 0.6 µl/well RNAiMAX was used for A549 cells.

Total RNA isolation and RNA-seq analysis. HeyA8 cells were transfected in 6-wells with siNT or either siCAG/CUG or siCGA/UCG oligonucleotides at 1 nM. The transfection mix was removed after 9 hours. Total RNA was isolated 48 hours after transfection using the miRNeasy Mini Kit (Qiagen, Cat.No. 74004) following the manufacturers instructions. An on-column digestion step using the RNAse-free DNAse Set (Qiagen, Cat.No.: 79254) was included. NGS RNA-SEQ library construction and sequencing was performed by the University of Chicago Genomics Facility. The quality and quantity of RNA samples was assessed using an Agilent bio-analyzer. RNA-SEQ libraries were generated using Illumina Stranded TotalRNA TruSeq kits according to the Illumina provided protocol and sequencing was performed using the Illumina HiSEQ4000 according to Illumina provided protocols and reagents. The resulting paired end reads were aligned to the hg38 assembly of the human genome with Tophat2. HTseq was used to associate the aligned reads with genes, and EdgeR was used to identify genes significantly differentially expressed between treatments, all as recently described [15]. The accession number for the RNA-Seq and expression data reported in this work are GSE104552.

Real-time PCR. Real-time PCR was performed a described recently [15] using the following primers: GAPDH (Hs00266705_g1), RPL14 (Hs03004339_g1), LRRC59 (Hs00372611_m1), CNPY3 (Hs01047697_m1), CTSA (Hs00264902_m1), and LRP8 (Hs00182998_m1).

Monitoring growth over time and quantification of cell death. To monitor cell growth over time, cells were seeded between 125 and 4000 per well in a 96-well plate in triplicates. The plate was then scanned using the IncuCyte ZOOM live cell imaging system (Essen BioScience). Images were captured at regular intervals, at the indicated time points, using a 10× objective. Cell confluence was calculated using the IncuCyte ZOOM software (version 2015A). IC50 values for siL3 and siCAG/CUG were determined using GraphPad Prism 6 software (by logarithm normalized sigmoidal dose curve fitting). Quantification of DNA fragmentation (subG1 DNA) was done as previously described [15].

siRNA screens and cell viability assay. HeyA8 or M565 cells were expanded and frozen down at the same passage. One week before transfection, cells were thawed and cultured in RPMI1640 medium, 10% FBS and 1% pen/strep. Cells were split three times during the week and each time seeded at $4\times10^6$ cells total in one T75 flask. On the day of the transfection, RNA duplexes were first diluted with Opti-MEM to make 30 µl solution of 10 nM (for the duplexes with the 6 mer seeds) or 1 nM (for the TNR-based duplexes) as final concentration in a 384-well plate by Multidrop Combi. Lipofectamine RNAiMAX (Invitrogen) was diluted in Opti-MEM (6 µl lipid+994 µl of Opti-MEM for HeyA8 and 15.2 µl lipid+984.8 µl of Opti-MEM for M565 cells). After incubating at room temperature for 5 to 10 minutes, 30 µl of the diluted lipid was dispensed into each well of the plate that contains RNA duplexes. The mixture was pipetted up and down three times by PerkinElmer EP3, incubated at room temperature for at least 20 minutes, and then the mixture was mixed again by PerkinElmer EP3. 15 µl of the mixture was then transferred into wells of three new plates (triplicates) using the PerkinElmer EP3. 50 µl with 320 HeyA8 or 820 M565 cells was then added to each well containing the duplex and lipid mix, which results in a final volume of 65 µl. Plates were left at room temperature for 30 minutes then moved to a 37° C. incubator. 96 hours post transfection, cell viability was assayed using CellTiter-Glo (Promega) quantifying cellular ATP content. 35 µl medium was removed from each well and 30 µl CellTiter-Glo cell viability reagent was added. The plates were shaken for 5 minutes and incubated at room temperature for 15 minutes. Luminescence was then read on the BioTek Synergy NEO2.

Treatment of xenografted ovarian cancer cells in vivo with templated lipoprotein particles (TLP) loaded with siRNAs. Synthesis of TLPs and production of siRNA-TLPs was done exactly as recently described [44]. $10^5$ HeyA8 cells (infected with a luciferase lentivirus and a NucRed lentivirus (Essen Bioscience)) were injected i.p. into 6-week-old female NSG mice [44] following the Northwestern University Institutional Animal Care and Use Committee (IACUC)-approved protocol. The growth of tumor cells in the mice over time was monitored non-invasively using the IVIS® Spectrum in vivo imaging system as recently described [44]. Each mouse of a treatment group was injected with 150 µl of either siNT-TLP or siCAG/CUG-TLP (1 µM stock).

Data analyses. To determine the number of triplets, 6 mer, 10 mer or 19 mer repeat sequences in the ORFs or 3'UTR of human or mouse genes, all ORF and 3'UTRs were extracted from the Homo sapiens (GRCh38.p7) or Mus musculus (GRCm38.p5) gene dataset of the Ensembl database using the Ensembl Biomart data mining tool. For each gene, only the longest deposited ORF or 3'UTR was considered. Custom perl scripts were used to identify whether each 3'UTR or ORF contained an identical match to a particular triplet, 6 mer, 10 mer or 19 mer.

GSEA was performed using the GSEA v2.2.4 software from the Broad Institute; 1000 permutations were used. Two list of 1846 survival and 418 nonsurvival genes were used as recently described [15, 45]. They were set as custom gene sets to determine enrichment of survival genes versus the nonsurvival control genes in downregulated genes from the RNA-seq data. Log (Fold Change) was used as the ranking metric. p-values below 0.05 were considered significantly enriched. The GO enrichment analysis shown was performed using all genes that after alignment and normalization were found to be at least 1.5 fold downregulated with an adjusted p values of <0.05, using the software available on Metascape.org and default running parameters. The data sets of HeyA8 cells with introduced siL3, shL1, shL3 or shR6 were recently described [15].

Sylamer analyses [25] were performed using the RNA-seq datasets from the HeyA8 cells transfected with siNT, siCAG/CUG or siCGA/UCG as recently described [15]. The analyses were performed using default settings. Enriched 6 or 10 mer motifs were analyzed using either ORFs or the 3'UTRs sequences. Sylamer (version 12-342) was run with the Markov correction parameter set to 4. DAVID gene ontology analysis was performed using the tool at https://david.ncifcrf.gov/home.jsp and default settings.

Statistical analyses. Two-way analysis of variances (ANOVA) were performed using the Stata 14 software to compare growth curves. One-tail student t-test was performed in the software package R to compare tumor load between treatment groups. Wilcoxon Rank Sum test was performed in R to compare IVIS signal between treatment groups. The effects of treatment on wild-type versus Drosha$^{-/-}$ cells were statistically assessed by fitting regression models that included linear and quadratic terms for value over time, main effects for treatment and cell type, and two- and three-way interactions for treatment, cell-type and time. The three-way interaction on the polynomial terms with treatment and cell type was evaluated for statistical significance since this represents the difference in treatment effects over the course of the experiment for the varying cell types. All statistical analyses were conducted in Stata 14 (RRID: SCR_012763) or R 3.3.1 in Rstudio (RRID:SCR_000432) except for Pearson correlation analyses, which were performed using StatPlus 6.2.2.

REFERENCES

1. Nalavade R, Griesche N, Ryan D P, Hildebrand S, Krauss S (2013) Mechanisms of RNA-induced toxicity in CAG repeat disorders. Cell Death Dis 4: e752
2. Gatchel J R, Zoghbi H Y (2005) Diseases of unstable repeat expansion: mechanisms and common principles. Nat Rev Genet 6: 743-55
3. Ross C A (2002) Polyglutamine pathogenesis: emergence of unifying mechanisms for Huntington's disease and related disorders. Neuron 35: 819-22
4. Orr H T, Zoghbi H Y (2007) Trinucleotide repeat disorders. Annu Rev Neurosci 30: 575-621
5. Cleary J D, Ranum L P (2017) New developments in RAN translation: insights from multiple diseases. Curr Opin Genet Dev 44: 125-134
6. Banez-Coronel M, Porta S, Kagerbauer B, Mateu-Huertas E, Pantano L, Ferrer I, Guzman M, Estivill X, Marti E (2012) A pathogenic mechanism in Huntington's disease involves small CAG-repeated RNAs with neurotoxic activity. PLoS Genet 8: e1002481
7. Napierala M, Krzyzosiak W J (1997) CUG repeats present in myotonin kinase RNA form metastable "slippery" hairpins. J Biol Chem 272: 31079-85
8. Wojciechowska M, Krzyzosiak W J (2011) Cellular toxicity of expanded RNA repeats: focus on RNA foci. Hum Mol Genet 20: 3811-21
9. Ho T H, Savkur R S, Poulos M G, Mancini M A, Swanson M S, Cooper T A (2005) Colocalization of muscleblind with RNA foci is separable from mis-regulation of alternative splicing in myotonic dystrophy. J Cell Sci 118: 2923-33
10. Lin L, Park J W, Ramachandran S, Zhang Y, Tseng YT, Shen S, Waldvogel H J, Curtis M A, Faull R L, Troncoso J C, et al. (2016) Transcriptome sequencing reveals aberrant alternative splicing in Huntington's disease. Hum Mol Genet 25: 3454-3466
11. Li L B, Yu Z, Teng X, Bonini N M (2008) RNA toxicity is a component of ataxin-3 degeneration in *Drosophila*. Nature 453: 1107-11

12. Hsu R J, Hsiao K M, Lin M J, Li C Y, Wang L C, Chen L K, Pan H (2011) Long tract of untranslated CAG repeats is deleterious in transgenic mice. PLoS One 6: e16417
13. Krol J, Fiszer A, Mykowska A, Sobczak K, de Mezer M, Krzyzosiak W J (2007) Ribonuclease dicer cleaves triplet repeat hairpins into shorter repeats that silence specific targets. Mol Cell 25: 575-86
14. Rue L, Banez-Coronel M, Creus-Muncunill J, Giralt A, Alcala-Vida R, Mentxaka G, Kagerbauer B, Zomeno-Abellan M T, Aranda Z, Venturi V, et al. (2016) Targeting CAG repeat RNAs reduces Huntington's disease phenotype independently of huntingtin levels. J Clin Invest 126: 4319-4330
15. Putzbach W, Gao Q Q, Patel M, van Dongen S, Haluck-Kangas A, Sarshad A A, Bartom E, Kim K Y, Scholtens D M, Hafner M, et al. (2017) Many si/shRNAs can kill cancer cells by targeting multiple survival genes through an off-target mechanism. eLife 6: e29702
16. Patel M, Peter M E (2017) Identification of DISE-inducing shRNAs by monitoring cellular responses. Cell Cycle: doi: 10.1080/15384101.2017.1383576
17. Hadji A, Ceppi P, Murmann A E, Brockway S, Pattanayak A, Bhinder B, Hau A, De Chant S, Parimi V, Kolesza P, et al. (2014) Death induced by CD95 or CD95 ligand elimination. Cell Reports 10: 208-222
18. Ji J, Sundquist K, Sundquist J (2012) Cancer incidence in patients with polyglutamine diseases: a population-based study in Sweden. Lancet Oncol 13: 642-8
19. Coarelli G, Diallo A, Thion M S, Rinaldi D, Calvas F, Boukbiza O L, Tataru A, Charles P, Tranchant C, Marelli C, et al. (2017) Low cancer prevalence in polyglutamine expansion diseases. Neurology 88: 1114-1119
20. Sorensen S A, Fenger K, Olsen J H (1999) Significantly lower incidence of cancer among patients with Huntington disease: An apoptotic effect of an expanded polyglutamine tract? Cancer 86: 1342-6
21. Turner M R, Goldacre R, Goldacre M J (2013) Reduced cancer incidence in Huntington's disease: record linkage study clue to an evolutionary trade-off? Clin Genet 83: 588-90
22. Clark R M, Dalgliesh G L, Endres D, Gomez M, Taylor J, Bidichandani S I (2004) Expansion of GAA triplet repeats in the human genome: unique origin of the FRDA mutation at the center of an Alu. Genomics 83: 373-83
23. Kozlowski P, de Mezer M, Krzyzosiak W J (2010) Trinucleotide repeats in human genome and exome. Nucleic Acids Res 38: 4027-39
24. Lee J M, Galkina E I, Levantovsky R M, Fossale E, Anne Anderson M, Gillis T, Srinidhi Mysore J, Coser K R, Shioda T, Zhang B, et al. (2013) Dominant effects of the Huntington's disease HTT CAG repeat length are captured in gene-expression data sets by a continuous analysis mathematical modeling strategy. Hum Mol Genet 22: 3227-38
25. van Dongen S, Abreu-Goodger C, Enright A J (2008) Detecting microRNA binding and siRNA off-target effects from expression data. Nat Methods 5: 1023-5
26. McMahon K M, Plebanek M P, Thaxton C S (2016) Properties of native high-density lipoproteins inspire synthesis of actively targeted in vivo siRNA delivery vehicles. Adv Funct Mater 26: 7824-7835
27. Yu Z, Teng X, Bonini N M (2011) Triplet repeat-derived siRNAs enhance RNA-mediated toxicity in a *Drosophila* model for myotonic dystrophy. PLoS Genet 7: e1001340
28. Lawlor K T, O'Keefe L V, Samaraweera S E, van Eyk C L, McLeod C J, Maloney C A, Dang T H, Suter C M, Richards R I (2011) Double-stranded RNA is pathogenic in *Drosophila* models of expanded repeat neurodegenerative diseases. Hum Mol Genet 20: 3757-68
29. Moseley M L, Zu T, Ikeda Y, Gao W, Mosemiller A K, Daughters R S, Chen G, Weatherspoon M R, Clark H B, Ebner T J, et al. (2006) Bidirectional expression of CUG and CAG expansion transcripts and intranuclear polyglutamine inclusions in spinocerebellar ataxia type 8. Nat Genet 38: 758-69
30. Sharp A H, Loev S J, Schilling G, Li S H, Li X J, Bao J, Wagster M V, Kotzuk J A, Steiner J P, Lo A, et al. (1995) Widespread expression of Huntington's disease gene (IT15) protein product. Neuron 14: 1065-74
31. Vonsattel J P, DiFiglia M (1998) Huntington disease. J Neuropathol Exp Neurol 57: 369-84
32. Bilen J, Liu N, Burnett B G, Pittman R N, Bonini N M (2006) MicroRNA pathways modulate polyglutamine-induced neurodegeneration. Mol Cell 24: 157-63
33. Jiang F, Ye X, Liu X, Fincher L, McKearin D, Liu Q (2005) Dicer-1 and R3D1-L catalyze microRNA maturation in *Drosophila*. Genes Dev 19: 1674-9
34. La Spada A R, Wilson E M, Lubahn D B, Harding A E, Fischbeck K H (1991) Androgen receptor gene mutations in X-linked spinal and bulbar muscular atrophy. Nature 352: 77-9
35. Gu M, Dong X, Zhang X, Niu W (2012) The CAG repeat polymorphism of androgen receptor gene and prostate cancer: a meta-analysis. Molecular biology reports 39: 2615-24
36. Ingles S A, Ross R K, Yu M C, Irvine R A, La Pera G, Haile R W, Coetzee G A (1997) Association of prostate cancer risk with genetic polymorphisms in vitamin D receptor and androgen receptor. J Natl Cancer Inst 89: 166-70
37. Giovannucci E, Stampfer M J, Krithivas K, Brown M, Dahl D, Brufsky A, Talcott J, Hennekens C H, Kantoff P W (1997) The CAG repeat within the androgen receptor gene and its relationship to prostate cancer. Proc Natl Acad Sci USA 94: 3320-3
38. Irvine R A, Yu M C, Ross R K, Coetzee G A (1995) The CAG and GGC microsatellites of the androgen receptor gene are in linkage disequilibrium in men with prostate cancer. Cancer Res 55: 1937-40
39. Hakimi J M, Schoenberg M P, Rondinelli R H, Piantadosi S, Barrack E R (1997) Androgen receptor variants with short glutamine or glycine repeats may identify unique subpopulations of men with prostate cancer. Clin Cancer Res 3: 1599-608
40. Tsujimoto Y, Takakuwa T, Takayama H, Nishimura K, Okuyama A, Aozasa K, Nonomura N (2004) In situ shortening of CAG repeat length within the androgen receptor gene in prostatic cancer and its possible precursors. Prostate 58: 283-90
41. Liu Y, Wilson S H (2012) DNA base excision repair: a mechanism of trinucleotide repeat expansion. Trends Biochem Sci 37: 162-72
42. Kim Y K, Kim B, Kim V N (2016) Re-evaluation of the roles of DROSHA, Export in 5, and DICER in microRNA biogenesis. Proc Natl Acad Sci USA 113: E1881-9
43. Zamudio J R, Kelly T J, Sharp P A (2014) Argonaute-bound small RNAs from promoter-proximal RNA polymerase II. Cell 156: 920-34
44. Murmann A E, McMahon K M, Halluck-Kangas A, Ravindran N, Patel M, Law C, Brockway S, Wei J J, Thaxton C S, Peter M E (2017) Induction of DISE in ovarian cancer cells in vivo. Oncotarget 8: 84643-84658
45. Wang T, Birsoy K, Hughes N W, Krupczak K M, Post Y, Wei J J, Lander E S, Sabatini D M (2015) Identification and characterization of essential genes in the human genome. Science 350: 1096-101
46. Blomen V A, Majek P, Jae L T, Bigenzahn J W, Nieuwenhuis J, Staring J, Sacco R, van Diemen F R, Olk N, Stukalov A, et al. (2015) Gene essentiality and synthetic lethality in haploid human cells. Science 350: 1092-6
47. Ceppi P, Hadji A, Kohlhapp F, Pattanayak A, Hau A, Xia L, Liu H, Murmann A E, Peter M E. (2014). CD95 and CD95L promote and protect cancer stem cells. Nature Commun. 5:5238.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

The invention claimed is:

1. A method of inhibiting the growth of a cancer cell or killing a cancer cell, the method comprising introducing into the cancer cell a double-stranded RNA comprising a passenger strand and a guide strand that form a duplex having a length of 15-30 nucleotides, wherein: (i) the passenger strand comprises a trinucleotide repeat sequence $(CAG)_n$, wherein n is an integer from 3-10; (ii) the guide strand comprises a trinucleotide repeat sequence $(CUG)_n$, wherein n is an integer from 3-10; and (iii) the $(CUG)_n$ and $(CAG)_n$ trinucleotide repeat sequences hybridize to each other to form at least part of the duplex, and (iv) the passenger strand comprises one or more modified nucleotides at the 5'-terminus that prevents loading of the passenger strand into an RNA-induced silencing complex (RISC), wherein the cancer cell is derived from an adenocarcinoma, leukemia, lymphoma, melanoma, myeloma, sarcoma, or teratocarcinoma or is derived from a cell of the adrenal gland, bladder, bone, bone marrow, brain, cervix, gall bladder, ganglia, gastrointestinal tract, heart, kidney, liver, lung, muscle, ovary, pancreas, parathyroid, skin, testis, thymus, or uterus.

2. The method of claim 1, wherein the RNA is an siRNA.

3. The method of claim 1, wherein the passenger strand comprises at least two modified nucleotides at its 5'-terminus.

4. The method of claim 1, wherein the one or more modified nucleotides at the 5'-terminus of the passenger strand are selected from the group consisting of 2'-O-methyl (2'OMe) nucleotides, 2'-deoxy-2'-fluoro (2'F) nucleotides, 2'-deoxy nucleotides, and 2'-O-(2-methoxyethyl) (MOE) nucleotides.

5. The method of claim 1, wherein the double-stranded polynucleotide comprises a 3' overhang of one or more nucleotides at the passenger strand, the guide strand, or both strands of the double-stranded polynucleotide.

6. The method of claim 1, wherein the cancer cell is an ovarian cancer cell, a hepatoma cell, a lung cancer cell, or a melanoma cell.

7. The method of claim 1, wherein the cancer cell is not a prostate cancer cell.

8. The method of claim 1, wherein n is an integer from 6-10.

9. The method of claim 8, wherein n is 6.

10. A method of inhibiting the growth of a cancer cell or killing a cancer cell, the method comprising introducing into the cancer cell a double-stranded RNA comprising a passenger strand and a guide strand that form a duplex having a length of 15-30 nucleotides, wherein: (i) the passenger strand comprises a trinucleotide repeat sequence $(CAG)_n$, wherein n is an integer from 3-10; (ii) the guide strand comprises a trinucleotide repeat sequence $(CUG)_n$, wherein n is an integer from 3-10; and (iii) the $(CUG)_n$ and $(CAG)_n$ trinucleotide repeat sequences hybridize to each other to form at least part of the duplex, wherein the passenger strand comprises one or more modified nucleotides at the 5'-terminus that prevents loading of the passenger strand into an RNA-induced silencing complex (RISC), wherein the cancer cell does not express androgen receptor.

11. The method of claim 10, wherein the RNA is an siRNA.

12. The method of claim 10, wherein the passenger strand comprises at least two modified nucleotides at its 5'-terminus.

13. The method of claim 10, wherein the one or more modified nucleotides at the 5'-terminus of the passenger strand are selected from the group consisting of 2'-O-methyl (2'OMe) nucleotides, 2'-deoxy-2'-fluoro (2'F) nucleotides, 2'-deoxy nucleotides, and 2'-O-(2-methoxyethyl) (MOE) nucleotides.

14. The method of claim 10, wherein the double-stranded polynucleotide comprises a 3' overhang of one or more nucleotides at the passenger strand, the guide strand, or both strands of the double-stranded polynucleotide.

15. The method of claim 10, wherein n is an integer from 6-10.

16. The method of claim 15, wherein n is 6.

17. A method of inhibiting the growth of a cancer cell or killing a cancer cell, the method comprising introducing into the cancer cell a double-stranded RNA comprising a passenger strand and a guide strand that form a duplex having a length of 15-30 nucleotides, wherein: (i) the passenger strand comprises a trinucleotide repeat sequence $(CAG)_n$, wherein n is 6; (ii) the guide strand comprises a trinucleotide repeat sequence $(CUG)_n$, wherein n is 6; and (iii) the $(CUG)_n$ and $(CAG)_n$ trinucleotide repeat sequences hybridize to each other to form at least part of the duplex, wherein the passenger strand comprises one or more modified nucleotides at the 5'-terminus that prevents loading of the passenger strand into an RNA-induced silencing complex (RISC), and wherein the cancer cell is not a prostate cancer cell or a breast cancer cell.

18. The method of claim 17, wherein the RNA is an siRNA.

* * * * *